(12) United States Patent
Altieri et al.

(10) Patent No.: US 9,987,294 B2
(45) Date of Patent: *Jun. 5, 2018

(54) MITOCHONDRIA-TARGETED ANTI-TUMOR AGENTS

(71) Applicant: University of Massachusetts, Boston, MA (US)

(72) Inventors: Dario C. Altieri, Worcester, MA (US); Byoung Heon Kang, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/070,657

(22) Filed: Mar. 15, 2016

(65) Prior Publication Data

US 2016/0184333 A1   Jun. 30, 2016

Related U.S. Application Data

(63) Continuation of application No. 13/905,008, filed on May 29, 2013, now abandoned, which is a continuation of application No. 12/208,207, filed on Sep. 10, 2008, now Pat. No. 8,466,140.

(60) Provisional application No. 60/993,195, filed on Sep. 10, 2007.

(51) Int. Cl.
| *A61K 31/675* | (2006.01) |
| *A61K 47/06* | (2006.01) |
| *A61K 47/22* | (2006.01) |
| *A61K 47/48* | (2006.01) |
| *C07D 225/06* | (2006.01) |

(52) U.S. Cl.
CPC ...... *A61K 31/675* (2013.01); *A61K 47/48023* (2013.01); *A61K 47/48092* (2013.01); *A61K 47/48192* (2013.01); *A61K 47/48315* (2013.01); *C07D 225/06* (2013.01)

(58) Field of Classification Search
None
See application file for complete search history.

(56) References Cited

U.S. PATENT DOCUMENTS

| 4,261,989 | A | 4/1981 | Sasaki et al. |
| 4,421,688 | A | 12/1983 | Muroi et al. |
| 4,939,239 | A | 7/1990 | Matsuhashi et al. |
| 5,051,448 | A | 9/1991 | Shashoua |
| 5,169,862 | A | 12/1992 | Burke, Jr. et al. |
| 5,192,746 | A | 3/1993 | Lobl et al. |
| 5,387,584 | A | 2/1995 | Schnur |
| 5,539,085 | A | 7/1996 | Bischoff et al. |
| 5,559,103 | A | 9/1996 | Gaeta et al. |
| 5,569,754 | A | 10/1996 | Williams et al. |
| 5,576,423 | A | 11/1996 | Aversa et al. |
| 5,804,604 | A | 9/1998 | Frankel et al. |
| 5,932,566 | A | 8/1999 | Schnur et al. |
| 6,015,659 | A | 1/2000 | Welch et al. |
| 6,855,705 | B1 | 2/2005 | Tian et al. |
| 6,870,049 | B1 | 3/2005 | Tian et al. |
| 6,887,993 | B1 | 5/2005 | Tian et al. |
| 6,953,680 | B2 | 10/2005 | Fuller et al. |
| 7,105,341 | B2 | 9/2006 | Kinsella |
| 7,115,651 | B2 | 10/2006 | Danishefsky et al. |
| 7,138,401 | B2 | 11/2006 | Kasibhatla et al. |
| 7,138,402 | B2 | 11/2006 | Kasibhatla et al. |
| 7,148,228 | B2 | 12/2006 | Kasibhatla et al. |
| 7,247,734 | B2 | 7/2007 | Drysdale et al. |
| 7,342,093 | B2 | 3/2008 | Altieri et al. |
| 7,553,821 | B2 | 6/2009 | Altieri |
| 7,888,334 | B2 | 2/2011 | Murphy et al. |
| 2003/0114450 | A1 | 6/2003 | Santi et al. |
| 2004/0072774 | A1 | 4/2004 | Manfredi et al. |
| 2006/0068453 | A1 | 3/2006 | Altieri |
| 2006/0204980 | A1 | 9/2006 | Altieri et al. |
| 2008/0171693 | A1 | 7/2008 | Altieri et al. |
| 2010/0119529 | A1 | 5/2010 | Furgson et al. |

FOREIGN PATENT DOCUMENTS

| JP | 63-218620 | 9/1988 |
| WO | WO 94/08578 | 4/1994 |
| WO | WO 00/03737 | 1/2000 |
| WO | WO 02/36574 | 5/2002 |
| WO | WO 02/079167 | 10/2002 |
| WO | WO 03/013430 | 2/2003 |
| WO | WO 03/066005 | 8/2003 |
| WO | WO 04/054624 | 7/2004 |
| WO | WO 06/014744 | 2/2006 |
| WO | WO 06/117669 | 11/2006 |
| WO | WO 07/134245 | 11/2007 |

OTHER PUBLICATIONS

Yang et al., Cancer Research, 2001, 61(10):4010-4016.*
Korean Intellectual Property Office, English Translation of the first preliminary Office Action issued in Korean Patent Application No. 10-2010-7007823 dated Dec. 19, 2014 (4 pages).
The Patent Office of the People's Republic of China, English Translation of the first Office Action issued in Chinese Patent Application No. 200880115423.0 dated Jun. 20, 2011 (3 pages).
Communication from Canadian Intellectual Property Office issued in Canadian Patent Application No. 2,699,794 dated Oct. 20, 2014 (4 pages).
Notification Concerning Transmittal of International Preliminary Report on Patentability issued for PCT/US2008/075895 dated Mar. 16, 2010, dated Mar. 25, 2010 (11 pages).
European Patent Office, Communication under Rule 164(2)(a) EPC, issued in EP Patent Application No. 08799427.3 dated Feb. 6, 2015 (7 pages).
European Patent Office, Communication pursuant to Rule 164(2)(b) and Article 94(3) EPC issued in EP Appl. No. 08 799427.3 dated Aug. 3, 2015, 18 pages.

(Continued)

*Primary Examiner* — Hong Sang
(74) *Attorney, Agent, or Firm* — Fish & Richardson P.C.

(57) ABSTRACT

Described are mitochondria-targeted anti-tumor agents, and methods of making and using the same for the treatment of disorders associated with unwanted cell proliferation.

22 Claims, 40 Drawing Sheets

(56) References Cited

OTHER PUBLICATIONS

Altieri, "Coupling apoptosis resistance to the cellular stress response: the IAP-Hsp90 connection in cancer," Cell Cycle, 3:255-256 (2004).
Altieri, "Validating survivin as a cancer therapeutic target," Nat. Rev. Cancer, 3:46-54 (2003).
Armstrong, J. S., "Mitochondrial Medicine: Pharmacological targeting of mitochondria in disease," British Journal of Pharmacology, 2007, vol. 151, pp. 1154-1163.
Armstrong, Jeffrey, S., "Mitochondria: a target for cancer therapy," British Journal of Pharmacology, 2006, vol. 147, No. 3, pp. 239-248.
Astriab-Fisher et al., "Conjugates of antisense oligonucleotides with the Tat and Antennapedia cell-penetrating peptides: Effects on cellular uptake, binding to target sequences, and biologic actions," Pharm. Res., 19:744-754 (2002).
Baines et al., "Loss of cyclophilin D reveals a critical role for mitochondrial permeability transition in cell death," Nature, 434:658-662 (2005).
Barril et al., "Structure-based discovery of a new class of Hsp90 inhibitors," Bioorg. Med. Chem. Lett., 15:5187-91 (2005).
Beere "The stress of dying: the role of heat shock proteins in the regulation of apoptosis," J. Cell Sci., 117:2641-51 (2004).
Bhattacharyya et al., "Cloning and subcellular localization of human mitochondrial hsp70," J. Biol. Chem., 270:1705-10 (1995).
Blagg et al., "Hsp90 inhibitors: small molecules that transform the Hsp90 protein folding machinery into a catalyst for protein degradation," Med. Res. Rev., 26:310-338 (2006).
Blanc-Brude et al., "Therapeutic targeting of the survivin pathway in cancer: initiation of mitochondrial apoptosis and suppression of tumor-associated angiogenesis," Clin. Cancer Res., 9:2683-92 (2003).
Briand et al., "Retro-inverso peptidomimetics as new immunological probes. Validation and application to the detection of antibodies in rheumatic diseases," J. Biol. Chem., 270:20686-91 (1995).
Bross et al., "Single-nucleotide variations in the genes encoding the mitochondrial Hsp60/Hsp10 chaperone system and their disease-causing potential," J. Hum. Genet., 52:56-65 (2007).
Brough et al., "4,5-diarylisoxazole Hsp90 chaperone inhibitors: potential therapeutic agents for the treatment of cancer," J. Med. Chem., 51:196-218 (2007).
Butcher, "Can cell systems biology rescue drug discovery?" Nat. Rev. Drug Discov., 4:461-467 (2005).
Camarero et al., "Biosynthesis of a head-to-tail cyclized protein with improved biological activity," J. Am. Chem. Soc., 121:5597-98 (1999).
Camarero et al., "Chemical synthesis of a circular protein domain: evidence for folding-assisted cyclization," Ang. Chem. Int. Ed., 37:347-349 (1998).
Camarero et al., "Chemoselective backbone cyclization of unprotected peptides," Chem. Commun, 1997:1369-70 (1997).
Cappello et al., "HSP60 and HSP10 down-regulation predicts bronchial epithelial carcinogenesis in smokers with chronic obstructive pulmonary disease," Cancer, 107:2417-24 (2006).
Cappello et al., "The expression of HSP60 and HSP10 in large bowel carcinomas with lymph node metastases," BMC Cancer, 5:139-148 (2005).
Cechetto et al., "Immunoelectron microscopy provides evidence that tumor necrosis factor receptor-associated protein 1 (TRAP-1) is a mitochondrial protein which also localizes at specific extramitochondrial sites," Exp. Cell Res., 260:30-39 (2000).
Cheng et al., "Synthesis and Enzyme-Specific Activation of Carbohydrate-Geldanamycin Conjugates with Potent Anticancer Activity", J. Med. Chem., vol. 48:645-652 (2005).
Deocaris et al., "On the brotherhood of the mitochondrial chaperones mortalin and heat shock protein 60," Cell Stress Chaperones, 11:116-128 (2006).
Deveraux et al., "IAP family proteins—suppressors of apoptosis," Genes Dev., 13:239-252 (1999).
Dohi et al., "Mitochondrial survivin inhibits apoptosis and promotes tumorigenesis," J. Clin. Invest., 114:1117-27 (2004).
Domanico et al., "Cloning of the gene encoding peptide-binding protein 74 shows that it is a new member of the heat shock protein 70 Family," Mol. Cell. Biol., 13:3598-3610 (1993).
Drysdale et al., "Targeting Hsp90 for the treatment of cancer," Curr. Opin. Drug Discov. Devel., 9:483-495 (2006).
Eccles et al., "NVP-AUY922: a novel heat shock protein 90 inhibitor active against xenograft tumor growth, angiogenesis, and metastasis," Cancer Res., 68:2850-60 (2008).
Eldred et al., "Orally active non-peptide fibrinogen receptor (GpIIb/IIIa) antagonists: identification of 4[4-[4-(aminoiminomethyl)phenyl]-1-piperazinyl]-1-piperidineacetic acid as a long-acting, broad-spectrum antithrombotic agent," J. Med. Chem., 37:3882-85 (1994).
EPO Authorized Officer Jens Ambrosch, International Search Report and Written Opinion for International Application No. PCT/US2008/075895, dated Nov. 11, 2009, 20 pages.
EPO Authorized Officer Jens Ambrosch, International Search Report and Written Opinion for International Application No. PCT/US2008/075895, dated Dec. 21, 2009, 20 pages.
Felts et al., "The hsp90-related protein TRAP1 is a mitochondrial protein with distinct functional properties," J. Biol. Chem., 275:3305-12 (2000).
Fernandez-Carneado et al., "Highly efficient, nonpeptidic oligoguanidinium vectors that selectively internalize into mitochondria," J. Am. Chem. Soc., 127:869-874 (2005).
Fortugno et al., "Regulation of survivin function by Hsp90," Proc. Natl. Acad. Sci. USA, 100:13791-96 (2003).
Goldenberg et al., "Circular and circularly permuted forms of bovine pancreatic trypsin inhibitor," J. Mol. Biol., 165:407-413 (1983).
Green et al., "The pathophysiology of mitochondrial cell death," Science, 305:626-629 (2004).
Guillemard and Saragovi, "Novel approaches for targeted cancer therapy," Curr. Cancer Drug Targets, 4:313-326 (2004).
Guo et al., "Formation of 17-Allylamino-Demethoxygeldanamycin (17-AGG) Hyroquinono by NAD(P)H:Quinone Oxidoreductase 1: Role of 17-AAG Hydroquinone in Heat Shock Protein 90 Inhibition," Cancer Research, 65:10006-10015 (2005).
Gyurkocza et al., "Antileukemic activity of shepherdin and molecular diversity of hsp90 inhibitors," J. Natl. Cancer Inst., 98:1068-77 (2006).
Hartl et al., "Molecular chaperones in the cytosol: from nascent chain to folded protein," Science, 295:1852-58 (2002).
Isaacs et al., "Heat shock protein 90 as a molecular target for cancer therapeutics," Cancer Cell, 3:213-217 (2003).
Jackson et al., "Enzymatic cyclization of linear peptide esters using subtiligase," J. Am. Chem. Soc., 117:819-820 (1995).
Kabouridis, "Biological applications of protein transduction technology," Trends Biotechnol., 21:498-503 (2003).
Kamal et al., "A high-affinity conformation of Hsp90 confers tumour selectivity on Hsp90 inhibitors," Nature, 425:407-410 (2003).
Kang et al., "Combinatorial drug design targeting multiple cancer signaling networks controlled by mitochondrial Hsp90," J. Clin. Invest., 119:454-464 (2009).
Kang et al., "Compartmentalized cancer drug discovery targeting mitochondrial Hsp90 chaperones," Oncogene, 28:3681-88 (2009).
Kang et al., "Regulation of tumor cell mitochondrial homeostasis by an organelle-specific Hsp90 chaperone network," Cell, 131:257-270 (2007).
Kaul et al., "Mouse and human chromosomal assignments of mortalin, a novel member of the murine hsp70 family of proteins," FEBS Lett., 361:269-272 (1995).
Kokoszka et al., "The ADP/ATP translocator is not essential for the mitochondrial permeability transition pore," Nature, 427:461-465 (2004).
Krauskopf et al., "Properties of the permeability transition in VDAC1(−/−) mitochondria," Biochim. Biophys. Acta, 1757:590-595 (2006).

(56) References Cited

OTHER PUBLICATIONS

Ku et al., "Potent non-peptide fibrinogen receptor antagonists which present an alternative pharmacophore," J. Med. Chem., 38:9-12 (1995).
Kuduk et al., "Synthesis and Evaluation of Geldanamycin-Estradiol Hybrids", Bioorganic & Medicinal Chemistry Letters, vol. 9:1233-1238 (1999).
Le Brazidec et al., "Synthesis and Biological Evaluation of a New Class of Geldanamycin Derivatives as Potent Inhibitors of Hsp90", J. Med. Chem., vol. 47:3865-3873 (2004).
Leav et al., "Cytoprotective mitochondrial chaperone TRAP-1 as a novel molecular target in localized and metastatic prostate cancer," Am. J. Pathol., 176:393-401 (2009).
Lindquist et al., "The heat-shock proteins," Annu. Rev. Genet., 22:631-677 (1988).
Lindsay, "Peptide-mediated cell delivery: Application in protein target validation," Curr. Opin. Pharmacol., 2:587-594 (2002).
Llauger-Bufi et al., "Synthesis of Novel Fluorescent Probes for the Molecular Chaperone Hsp90", Bioorganic & Medicinal Chemistry Letters, vol. 13:3975-3978 (2003).
Mandler et al., "Synthesis and Evaluation of Antiproliferative Activity of a Geldanamycin-Herceptin™ Immunoconjugate," Bioorganic & Medicinal Chemistry Letters, 10:1025-1028 (2000).
Marsh, "Preparation and Properties of 'Allergoids' Derived from Native Pollen Allergens by Mild Formalin Treatment," Int. Arch. Allergy, 41:199-215 (1971).
Mayo et al., "Design of a partial peptide mimetic of anginex with antiangiogenic and anticancer activity," J. Biol. Chem., 278:45746-52 (2003).
Meli et al., "Small-molecule targeting of heat shock protein 90 chaperone function: rational identification of a new anticancer lead," J. Med. Chem., 49:7721-30 (2006).
Moulick et al., "Synthesis of a red-shifted fluorescence polarization probe for Hsp90", Bioorganic & Medicinal Chemistry Letters, vol. 16:4515-4518 (2006).
Muchmore et al., "Crystal structure and mutagenic analysis of the inhibitor-of-apoptosis protein survivin," Mol. Cell, 6:173-182 (2000).
Nakagawa et al., "Cyclophilin D-dependent mitochondrial permeability transition regulates some necrotic but not apoptotic cell death.," Nature, 434:652-658 (2005).
Neckers et al., "Heat shock protein 90," Curr. Opin. Oncol., 15:419-424 (2003).
Office Action, Japanese Patent Application No. 2010-524247, dated Mar. 14, 2013, 4 pages in English.
Okada and Mak, "Pathways of apoptotic and non-apoptotic death in tumour cells," Nat. Rev. Cancer, 4:592-603 (2004).
Pandey et al., "Negative regulation of cytochrome C-mediated oligomerization of Apaf-1 and activation of procaspase-9 by heat shock protein 90," EMBO J., 19:4310-22 (2000).
Paul et al., "Hsp27 as a negative regulator of cytochrome C release," Mol. Cell. Biol., 22:816-834 (2002).
Phillips, "Compartmentalized signalling of Ras," Biochem. Soc. Trans. 33:657-661 (2005).
Plescia et al., "Rational design of shepherdin, a novel anticancer agent," Cancer Cell, 7:457-468 (2005).
Ren et al., "MUC1 oncoprotein is targeted to mitochondria by heregulin-induced activation of c-Src and the molecular chaperon HSP90," Oncogene, 2006, vol. 25, pp. 20-31.
Reynolds et al., eds., Martindale, The Extra Pharmacopoeia, 31st Edition, Royal Pharmaceutical Society, London GB, pp. 267-268 (1996).
Roe et al., "Structural basis for inhibition of the Hsp90 molecular chaperone by the antitumor antibiotics radicicol and geldanamycin," J. Med. Chem., 42:260-266 (1999).
Samali et al., "Presence of a pre-apoptotic complex of pro-caspase-3, Hsp60 and Hsp10 in the mitochondrial fraction of Jurkat cells," EMBO J., 18:2040-48 (1999).
Sato et al., "Modulation of Akt kinase activity by binding to Hsp90," Proc. Natl. Acad. Sci. USA, 97:10832-37 (2000).
Sawada et al., "Cytoprotective membrane-permeable peptides designed from the Bax-binding domain of Ku70," Nat. Cell Biol., 5:352-357 (2003).
Schimmer, "Inhibitor of apoptosis proteins: translating basic knowledge into clinical practice," Cancer Res., 64:7183-90 (2004).
Schnur et al., "erbB-2 oncogene inhibition by geldanamycin derivatives: synthesis, mechanism of action, and structure-activity relationships," J. Med. Chem., 38:3813-20 (1995).
Schnur et al., "Inhibition of the oncogene product p185erbB-2 in vitro and in vivo by geldanamycin and dihydrogeldanamycin derivatives," J. Med. Chem., 38:3806-312 (1995).
Shan et al., "Hsp10 and Hsp60 modulate Bcl-2 family and mitochondria apoptosis signaling induced by doxorubicin in cardiac muscle cells," J. Mol. Cell. Biol., 35:1135-43 (2003).
Sharp et al., "In vitro biological characterization of a novel, synthetic diaryl pyrazole resorcinol class of heat shock protein 90 inhibitors," Cancer Res., 67:2206-16 (2007).
Sharp et al., "Inhibition of the heat shock protein 90 molecular chaperone in vitro and in vivo by novel, synthetic, potent resorcinylic pyrazole/isoxazole amide analogues," Mol. Cancer Ther., 6:1198-1211 (2007).
Singh et al., "Anticonvulsant activity and selective inhibition of nicotinamide adenine dinucleotide-dependent oxidations by 10-(2-arylimino-3-acetylamino-4-thiazolidonyl) phenothiazines," J. Pharm. Sci., 65:391-396 (1976).
Singh et al., "Mitochondrial import of the human chaperonin (HSP60) protein," Biochem. Biophys. Res. Commun., 169:391-396 (1990).
Soga et al., "Development of radicicol analogues," Curr. Cancer Drug Targets, 3:359-369 (2003).
Soltys et al., "Mitochondrial proteins at unexpected cellular locations: export of proteins from mitochondria from an evolutionary, perspective," Int. Rev. Cytol., 194:133-196 (2000).
Song et al., "Identification of a protein with homology to hsp90 that binds the type 1 tumor necrosis factor receptor," J. Biol. Chem., 270:3574-81 (1995).
Stebbins et al., "Crystal structure of an Hsp90-geldanamycin complex: targeting of a protein chaperone by an antitumor agent," Cell, 89:239-250 (1997).
Strausberg et al., "Oncogenomics and the development of new cancer therapies," Nature, 429:469-474 (2004).
Sugita et al., "Improved cytosolic translocation and tumor-killing activity of Tat-shepherdin conjugates mediated by co-treatment with Tat-fused endosome-disruptive HA2 peptide," Biochem. Biophys. Res. Commun., 363:1027-32 (2007).
Tam et al., "A biomimetic strategy in the synthesis and fragmentation of cyclic protein," Protein Sci., 7:1583-92 (1998).
Tang et al., "Expression of heat shock proteins and heat shock protein messenger ribonucleic acid in human prostate carcinoma in vitro and in vivo," Cell Stress Chaperones, 10:46-58 (2005).
Thomas et al., "Expression of heat-shock proteins is associated with major adverse prognostic factors in acute myeloid leukemia," Leuk. Res., 29:1049-58 (2005).
Wadhwa et al., "Inactivation of tumor suppressor p53 by Mot-2, a hsp70 family member," J. Biol. Chem., 273:2586-91 (1998).
Wadhwa et al., "Reduction in mortalin level by its antisense expression causes senescence-like growth arrest in human immortalized cells," J. Gene Med., 6:439-444 (2004).
Wadhwa et al., "Upregulation of mortalin/mthsp70/Grp75 contributes to human carcinogenesis," Int. J. Cancer, 118:2973-80 (2006).
Whitesell et al., "Hsp90 and the chaperoning of cancer," Nat. Rev. Cancer, 5:761-772 (2005).
Xanthoudakis et al., "Hsp60 accelerates the maturation of pro-caspase-3 by upstream activator proteases during apoptosis," EMBO J., 18:2049-56 (1999).
Young et al., Molecular chaperones Hsp90 and Hsp70 deliver preproteins to the mitochondrial import receptor Tom70, Cell, 112:41-50 (2003).
Zhang et al., "Synthesis and application of unprotected cyclic peptides as building blocks for peptide dendrimers," J. Am. Chem. Soc., 119:2363-70 (1997).

(56) References Cited

OTHER PUBLICATIONS

Zhao et al., "A mitochondrial specific stress response in mammalian cells," EMBO J., 21:4411-19 (2002).

* cited by examiner

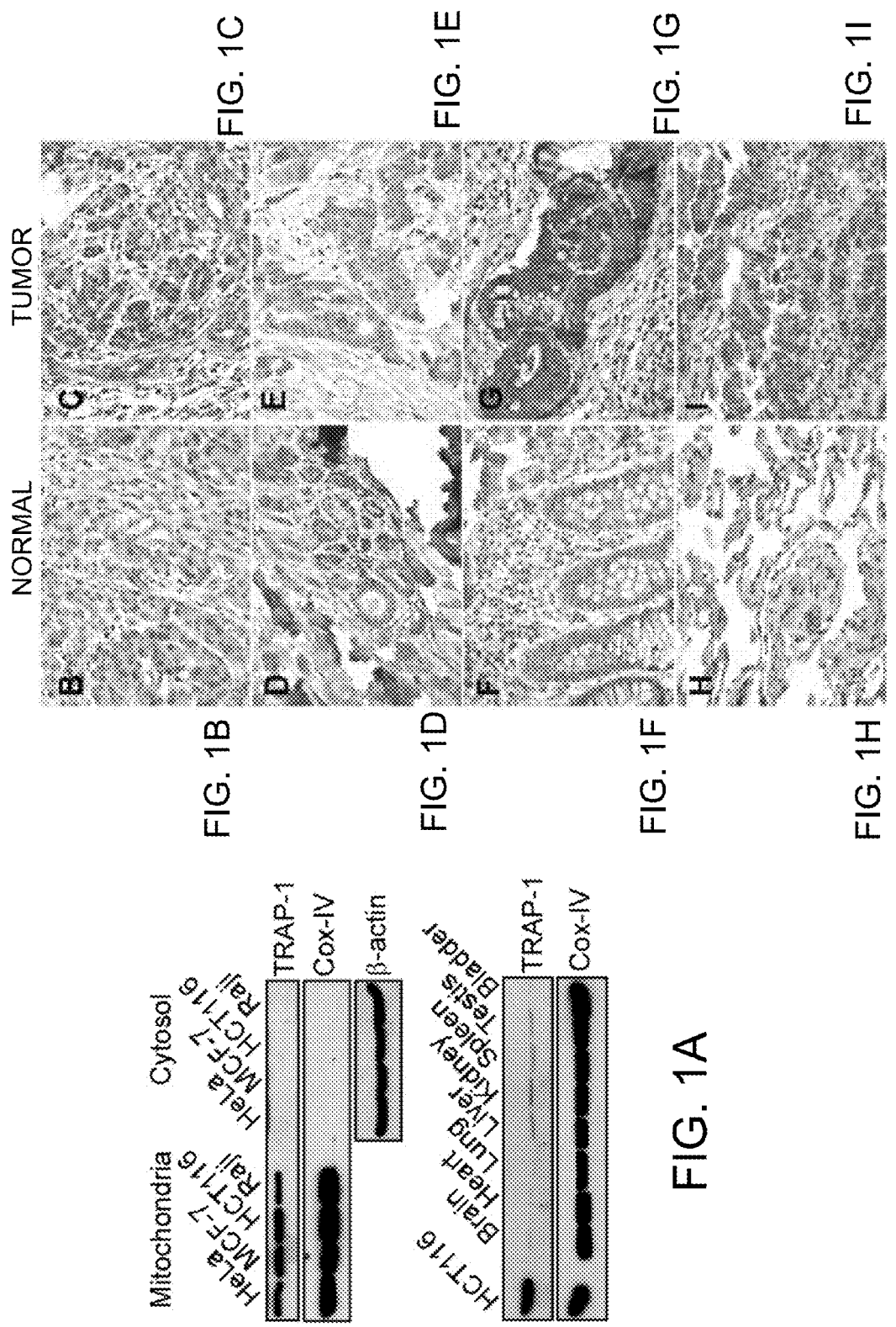

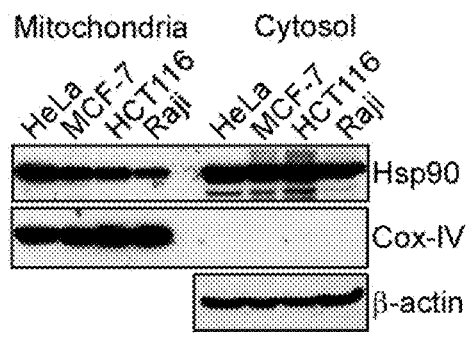
FIG. 1J
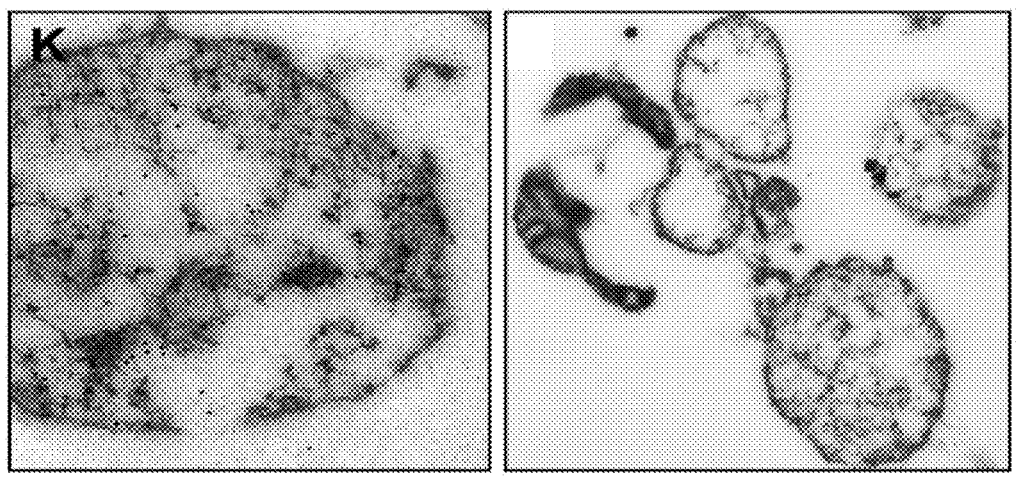
FIG. 1K
FIG. 1L
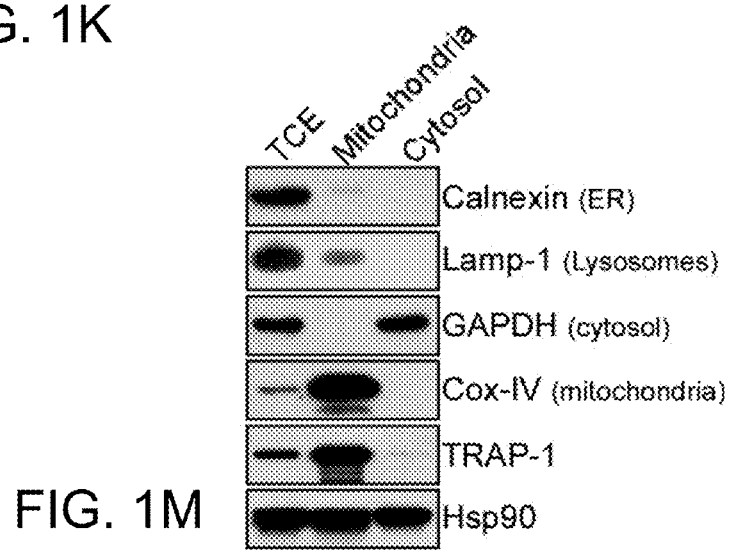
FIG. 1M

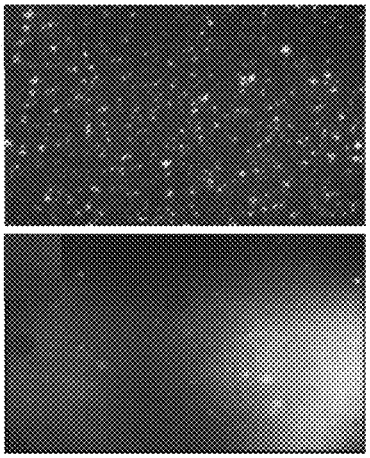
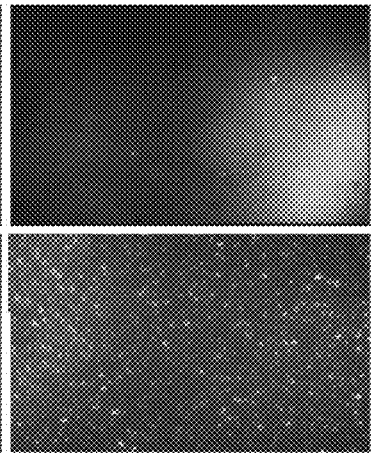
FIG. 3A  FIG. 3B
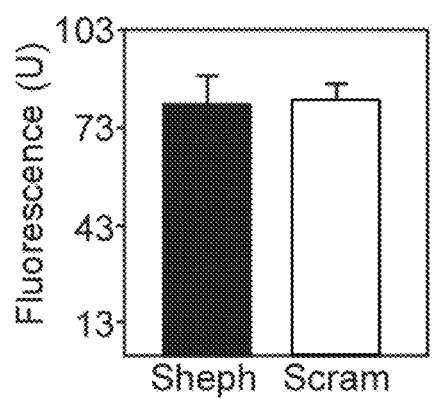
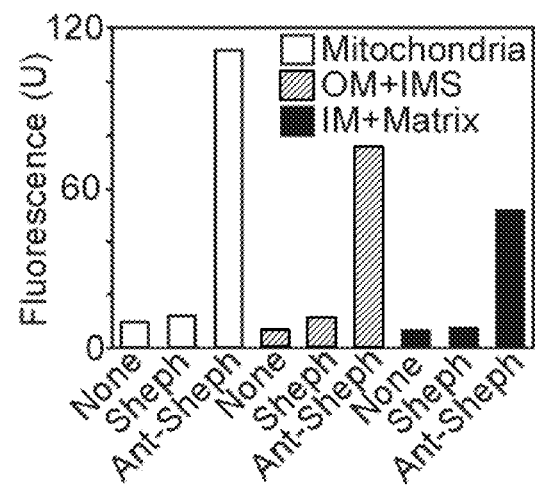
FIG. 3C  FIG. 3D
FIG. 3E
FIG. 3F

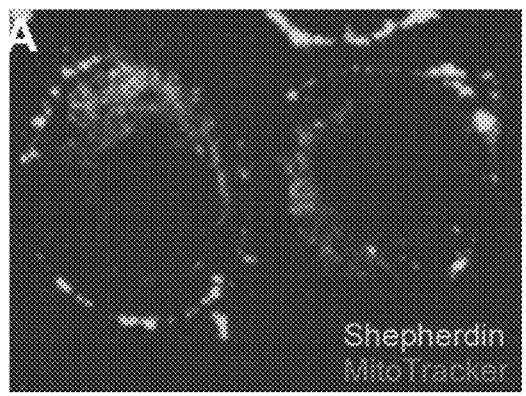
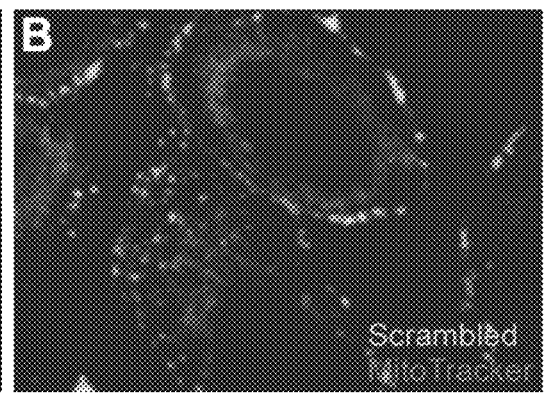
FIG. 5A    FIG. 5B
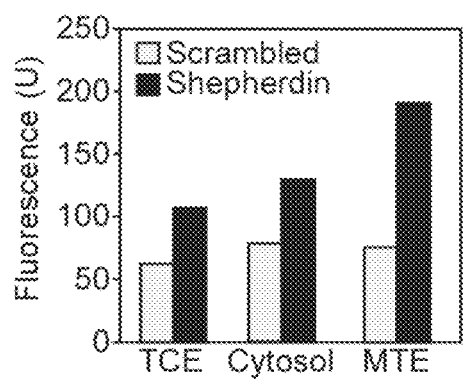
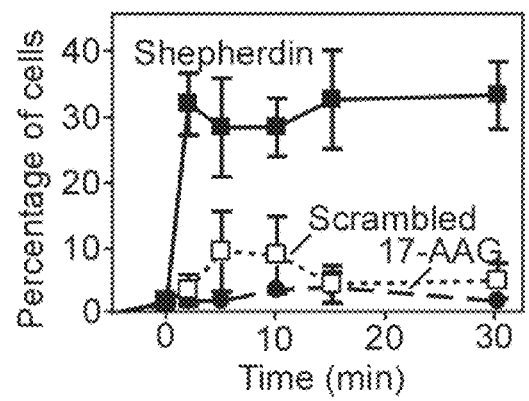
FIG. 5C    FIG. 5D
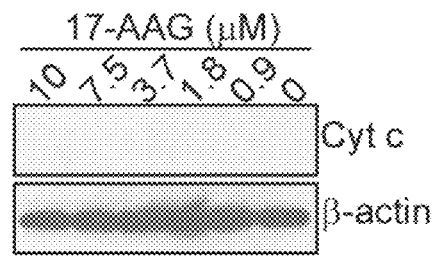
FIG. 5E

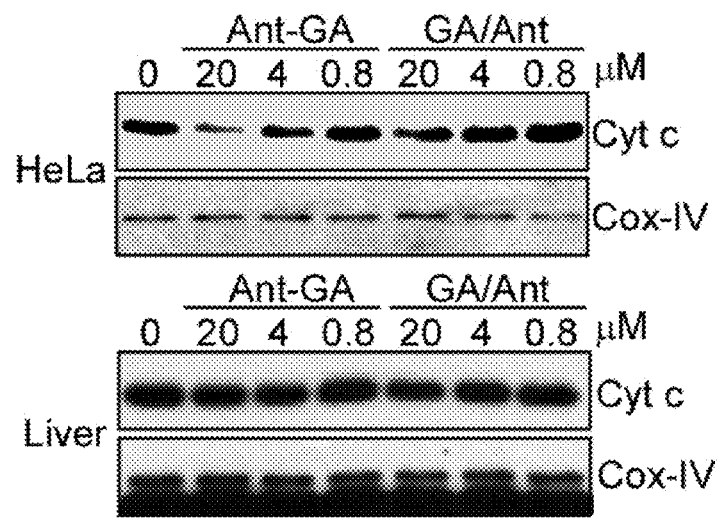
FIG. 7C
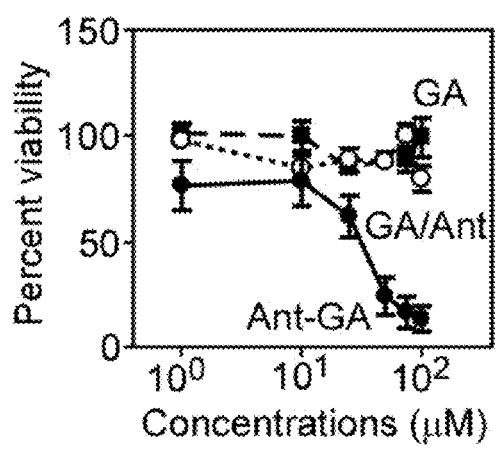 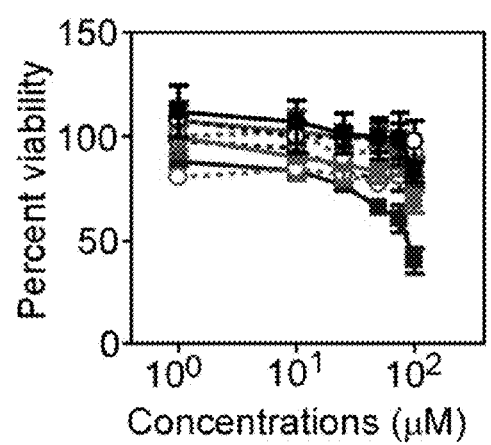
FIG. 7D            FIG. 7E

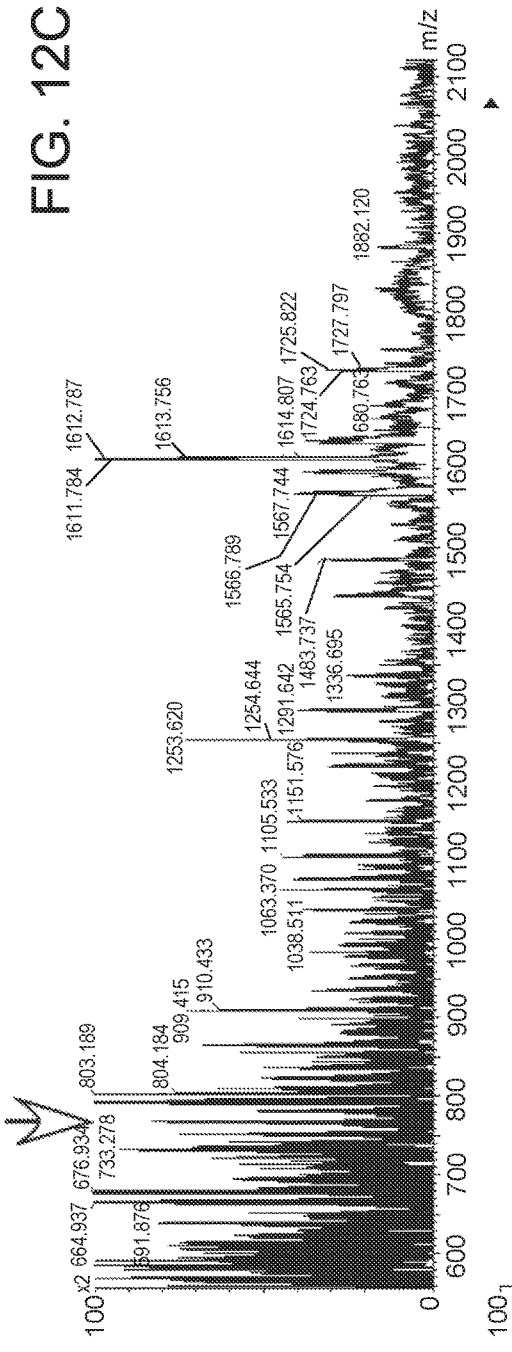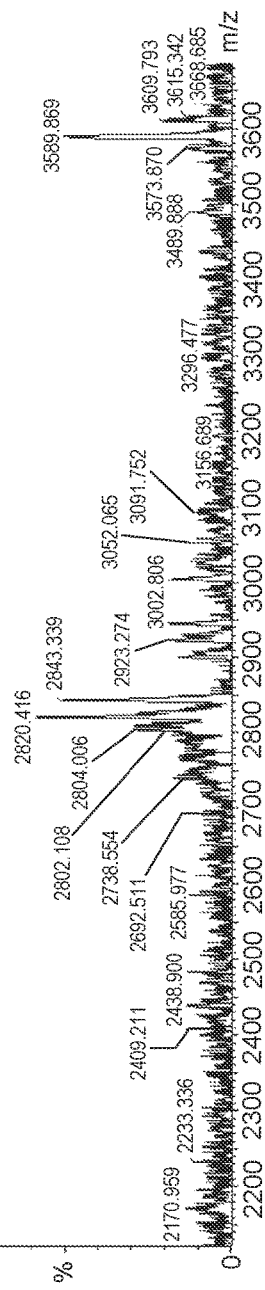
FIG. 12C
FIG. 12C (cont'd)

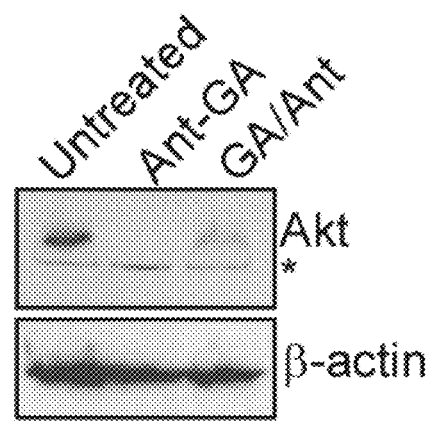
FIG. 12D
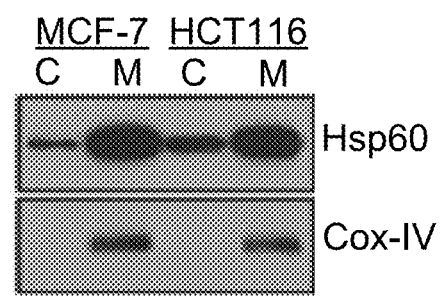
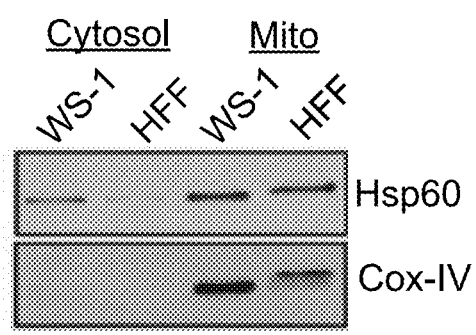
FIG. 13A

| SEQ ID NO: | SEQUENCE | NOTES |
|---|---|---|
| 1. | MGAPTLPPAWQPFLKDHRISTFKNWPFLEGCACTPERMAEA GFIHCPTENEPDLAQCFFCFKELEGWEPDDDPIEEHKKHSSGC AFLSVKKQFEELTLGEFLKLDRERAKNKIAKETNNKKKEFEE TAKKVRRAIEQLAAMD | human shepherdin |
| 2. | His-Ser-Ser-Gly-Cys s | human |
| 3. | Lys His Ser Ser Gly Cys Ala Phe Leu Ser Val Lys | human |
| 4. | Ile Asp Asp His Lys Lys His Ser Ser Gly Cys Ala Phe Leu | human |
| 5. | Lys Lys His Ser Ser Gly Cys Ala Phe Leu | human |
| 6. | Lys His Ser Ser Gly Cys | human |
| 7. | His Ser Ser Gly Cys Ala | human |
| 8. | Lys His Ser Ser Gly Cys Ala | human |
| 9. | Lys Lys His Ser Ser Gly Cys | human |
| 10. | His Ser Ser Gly Cys Ala Phe | human |
| 11. | His Lys Lys His Ser Ser Gly Cys Ala Phe Leu Ser Val Lys Lys | human |
| 12. | Lys His Ser Ser Gly Cys Ala Phe Leu | human |
| 13. | Thr-Ser-His-His-His-His-His-His-Cys | Artificial sequence |
| 14. | RLKTFANFPSGSPVSASTLARAGFLYTGEGDTVRCFSCHAAV DRWQYGDSAVGRHRKVSPNCRFIN (SEQ ID NO:14) | first BIR domain of human XIAP |
| 15. | RMSTYSTFPAGVPVSERSLARAGFYYTGVNDKVKCFCCGLM LDNWKRGDSPTEKHKKLYPSCRFVQ (SEQ ID NO:15) | first BIR domain of human cIAP1 |
| 16. | RMSTYSTFPAGVPVSERSLARAGFYYTGVNDKVKCFCCGLM LDNWKLGDSPIQKHKQLYPSCSFIQ (SEQ ID NO:16) | first BIR domain of human cIAP2 |

FIG. 14

| | | |
|---|---|---|
| 17. | MSLLFSRCNSIVTVKKNKRHMAEVNASPLKHFVTAKKKING IFEQLGAYIQESATFLEDTYRNAELDPVTTEEQVLDVKGYLS KVRGISEVLARRHMKVAFFGRTSNGKSTVINAMLWDKVLPS GIGHTTNCFLRVEGTDGHEAFLLTEGSEEKRSAKTVNQLAH ALHQDKQLHAGSLVSVMWPNSKCPLLKDDLVLMDSPGIDV TTELDSWIDKFCLDADVFVLVANSESTLMQTEKHFFHKVSE RLSRPNIFILNNRWDASASEPEYMEEVRRQHMERCTSFLVDE LGVVDRSQAGDRIFFVSAKEVLNARIQKAQGMPEGGGALAE GFQVRMFEFQNFERRFEECISQSAVKTKFEQHTVRAKQIAEA VRLIMDSLHMAAREQQVYCEEMREERQDRLKFIDKQLELL AQDYKLRIKQITEEVERQVSTAMAEEIRRLSVLVDDYQMDF HPSPVVLKVYKNELHRHIEEGLGRNMSDRCSTAITNSLQTM QQDMIDGLKPLLPVSVRSQIDMLVPRQCFSLNYDLNCDKLC ADFQEDIEFHFSLGWTMLVNRFLGPKNSRRALMGYNDQVQ RPIPLTPANPSMPPLPQGSLTQEEFMVSMVTGLASLTSRTSM GILVVGGVVWKAVGWRLIALSFGLYGLLYVYERLTWTTKA KERAFKRQFVEHASEKLQLVISYTGSNCSHQVQQELSGTFA HLCQQVDVTRENLEQEIAAMNKKIEVLDSLQSKAKLLRNKA GWLDSELNMFTHQYLQPSR | Human mitofusin 2 |
| 18. | RQIKIWFQNRRMKWKK | drosophila |
| 19. | RKKRRQRRR | HIV-1 Tat basic domain |
| 20. | RKKRRORRRGC; | Modified HIV-1 Tat basic domain |
| 21. | CCGCCAAGAAGCG | Nucleic acid! Human RNA mito-chondrial penetrating signal |
| 22. | GCGTGCACACGCGCGTAGACTTCCCCCGCAAGTCACTCGT TAGCCCGCCAAGAAGCGACCCCTCCGGGGCGAGCTGAGC GGCGTGGCGCGGGGGCGTCAT | Nucleic acid! Human RNA mito-chondrial penetrating signal |

FIG. 14
(Cont'd)

| 23. | ACGTGCATACGCACGTAGACATTCCCCGCTTCCCACTCC AAAGTCCGCCAAGAAGCGTATCCCGCTGAGCGGCGTGGC GCGGGGGCGTCATCCGTCAGCTC | Nucleic acid! Human RNA mito-chondrial penetrating signal |
|---|---|---|
| 24. | ACTTCCCCCGCAAGTCACTCGTTAGCCC GCCAAGAAGCGACCCCTCCGGGGCGAGCTG | Nucleic acid! Human RNA mito-chondrial penetrating signal |
| 25. | LFACGSSHK | Synthetic |
| 26. | CGSSH | Synthetic |
| 27. | GSSHK | Synthetic |
| 28. | KKWKMRRNQFWVKVQRLFACGSSHK | Synthetic |
| 29. | KKWKMRRNQFWVKVQRCGSSH | Synthetic |
| 30. | KKWKMRRNQFWVKVQRGSSHK | Synthetic |
| 31. | AAAAAGAATTCCTGGCGCTGCGCTGCGGCTC | primer |
| 32. | AAAAACTCGAGCAGATTAGCTCAACTGGCCACAGTC | primer |
| 33. | AAAAAGAATTCGGCGGCATGTGCAGCAAGGGCTCCGGCG | primer |
| 34. | AAAAACTCGAGCAGATTAGCTCAACTGGCCACAGTC | primer |
| 35. | AAAAAGGATCCGTACGACATGGCGCGCGA | primer |
| 36. | AAAAAGGATCCAGCACGCAGACCGCCGAGG | primer |
| 37. | AAAAACTCGAGCTAGTGTCGCTCCAGGGCCTT | primer |
| 38. | AAAAAGGATCCAGGAGGATGTTCTCGTCCGTAGC | primer |
| 39. | AAAAACTCGAGCTACTCAGTTAACCCAAGCTTCTTCTTC | primer |
| 40. | RQIKIWFQNRRMKWKKC | Synthetic |
| 41. | RRIVVLHGYGAVKEVLLNHK | synthetic |
| 42. | MLSLRQDIRFFKPATRTLCSSR | synthetic |

FIG. 14
(Cont'd)

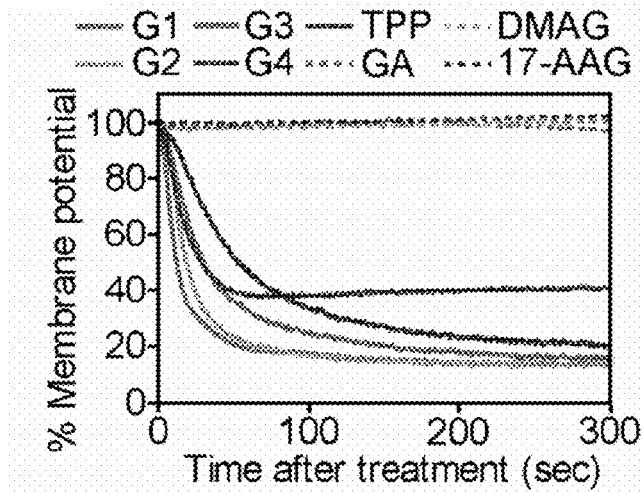
FIG. 16A
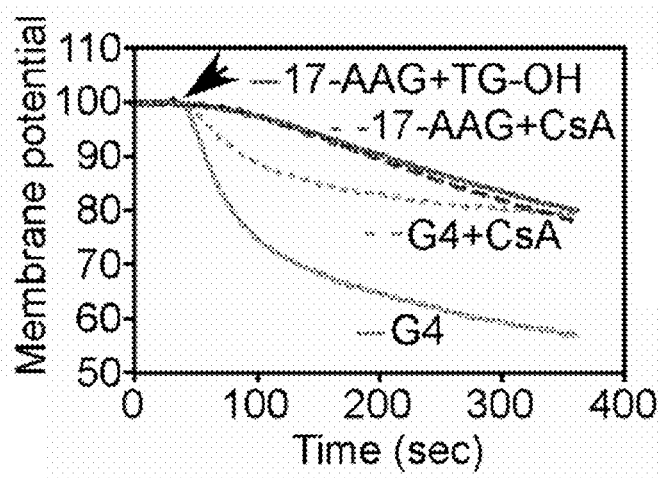
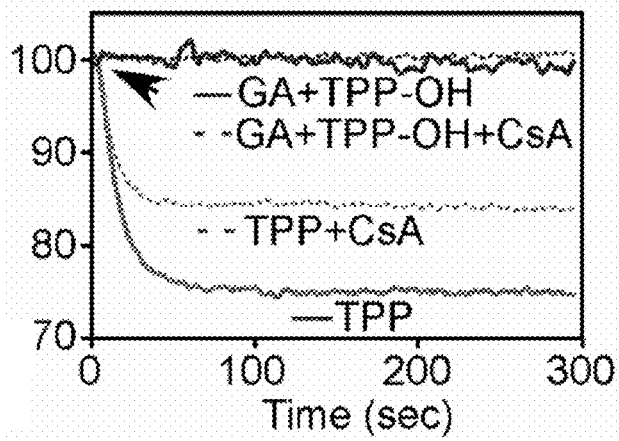
FIG. 16B

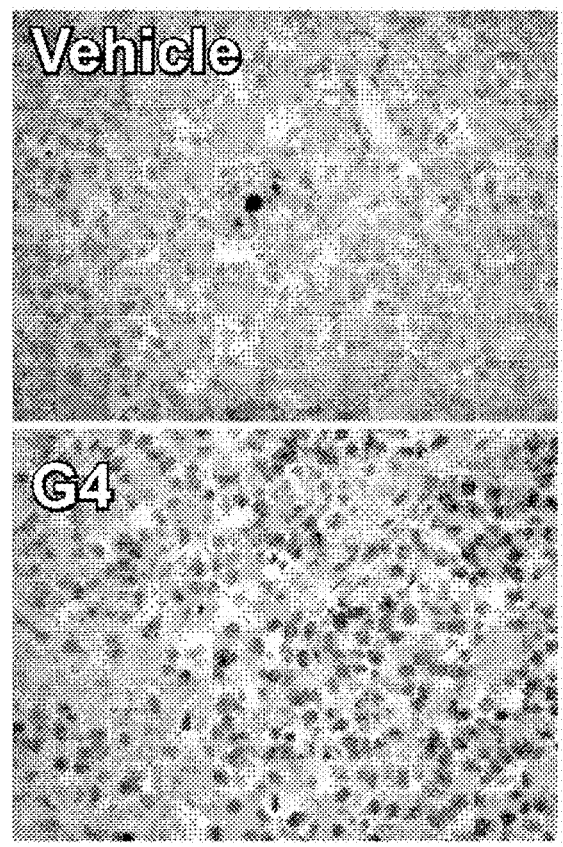
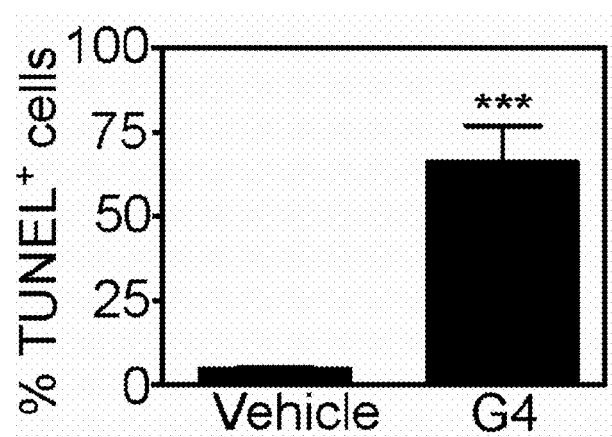
FIG. 18B

SEQUENCE LISTING

<160> NUMBER OF SEQ ID NOS: 42

<210> SEQ ID NO 1
<211> LENGTH: 142
<212> TYPE: PRT
<213> ORGANISM: Homo sapiens

<400> SEQUENCE: 1

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

<210> SEQ ID NO 2
<211> LENGTH: 6
<212> TYPE: PRT
<213> ORGANISM: Homo sapiens

<400> SEQUENCE: 2

His Ser Ser Gly Cys Ser
1               5

<210> SEQ ID NO 3
<211> LENGTH: 12
<212> TYPE: PRT
<213> ORGANISM: Homo sapiens

<400> SEQUENCE: 3

Lys His Ser Ser Gly Cys Ala Phe Leu Ser Val Lys
1               5                   10

<210> SEQ ID NO 4
<211> LENGTH: 14
<212> TYPE: PRT
<213> ORGANISM: Homo sapiens

<400> SEQUENCE: 4

Ile Asp Asp His Lys Lys His Ser Ser Gly Cys Ala Phe Leu
1               5                   10

<210> SEQ ID NO 5
<211> LENGTH: 10
<212> TYPE: PRT
<213> ORGANISM: Homo sapiens

<400> SEQUENCE: 5

Lys Lys His Ser Ser Gly Cys Ala Phe Leu

```
                1               5                    10
```

<210> SEQ ID NO 6
<211> LENGTH: 6
<212> TYPE: PRT
<213> ORGANISM: Homo sapiens

<400> SEQUENCE: 6

```
Lys His Ser Ser Gly Cys
1               5
```

<210> SEQ ID NO 7
<211> LENGTH: 6
<212> TYPE: PRT
<213> ORGANISM: Homo sapiens

<400> SEQUENCE: 7

```
His Ser Ser Gly Cys Ala
1               5
```

<210> SEQ ID NO 8
<211> LENGTH: 7
<212> TYPE: PRT
<213> ORGANISM: Homo sapiens

<400> SEQUENCE: 8

```
Lys His Ser Ser Gly Cys Ala
1               5
```

<210> SEQ ID NO 9
<211> LENGTH: 7
<212> TYPE: PRT
<213> ORGANISM: Homo sapiens

<400> SEQUENCE: 9

```
Lys Lys His Ser Ser Gly Cys
1               5
```

<210> SEQ ID NO 10
<211> LENGTH: 7
<212> TYPE: PRT
<213> ORGANISM: Homo sapiens

<400> SEQUENCE: 10

```
His Ser Ser Gly Cys Ala Phe
1               5
```

<210> SEQ ID NO 11
<211> LENGTH: 15
<212> TYPE: PRT
<213> ORGANISM: Homo sapiens

<400> SEQUENCE: 11

```
His Lys Lys His Ser Ser Gly Cys Ala Phe Leu Ser Val Lys Lys
1               5                   10                  15
```

<210> SEQ ID NO 12
<211> LENGTH: 9
<212> TYPE: PRT
<213> ORGANISM: Homo sapiens

<400> SEQUENCE: 12

```
Lys His Ser Ser Gly Cys Ala Phe Leu
1               5
```

<210> SEQ ID NO 13
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 13

Thr Ser His His His His His His Cys
1               5

<210> SEQ ID NO 14
<211> LENGTH: 66
<212> TYPE: PRT
<213> ORGANISM: Homo sapiens

<400> SEQUENCE: 14

Arg Leu Lys Thr Phe Ala Asn Phe Pro Ser Gly Ser Pro Val Ser Ala
1               5                   10                  15

Ser Thr Leu Ala Arg Ala Gly Phe Leu Tyr Thr Gly Glu Gly Asp Thr
            20                  25                  30

Val Arg Cys Phe Ser Cys His Ala Ala Val Asp Arg Trp Gln Tyr Gly
        35                  40                  45

Asp Ser Ala Val Gly Arg His Arg Lys Val Ser Pro Asn Cys Arg Phe
    50                  55                  60

Ile Asn
65

<210> SEQ ID NO 15
<211> LENGTH: 64
<212> TYPE: PRT
<213> ORGANISM: Homo sapiens

<400> SEQUENCE: 15

Arg Met Ser Thr Tyr Ser Thr Phe Pro Ala Gly Val Pro Val Ser Ser
1               5                   10                  15

Leu Ala Arg Ala Gly Phe Tyr Tyr Thr Gly Val Asn Asp Lys Val Lys
            20                  25                  30

Cys Phe Cys Cys Gly Leu Met Leu Asp Asn Trp Lys Arg Gly Asp Ser
        35                  40                  45

Pro Thr Glu Lys His Lys Lys Leu Tyr Pro Ser Cys Arg Phe Val Gln
    50                  55                  60

<210> SEQ ID NO 16
<211> LENGTH: 64
<212> TYPE: PRT
<213> ORGANISM: Homo sapiens

<400> SEQUENCE: 16

Arg Met Ser Thr Tyr Ser Thr Phe Pro Ala Gly Val Pro Val Ser Ser
1               5                   10                  15

Leu Ala Arg Ala Gly Phe Tyr Tyr Thr Gly Val Asn Asp Lys Val Lys
            20                  25                  30

Cys Phe Cys Cys Gly Leu Met Leu Asp Asn Trp Lys Leu Gly Asp Ser
        35                  40                  45

Pro Ile Gln Lys His Lys Gln Leu Tyr Pro Ser Cys Ser Phe Ile Gln
    50                  55                  60

<210> SEQ ID NO 17
<211> LENGTH: 747

<212> TYPE: PRT
<213> ORGANISM: Homo sapiens

<400> SEQUENCE: 17

```
Met Ser Leu Leu Phe Ser Arg Cys Asn Ser Ile Val Thr Val Lys Lys
1               5                   10                  15

Asn Lys Arg His Met Ala Glu Val Asn Asp Leu Lys His Phe Val Thr
            20                  25                  30

Ala Lys Lys Lys Ile Asn Gly Ile Phe Glu Gln Leu Gly Ala Tyr Ile
        35                  40                  45

Gln Glu Ser Ala Thr Phe Leu Glu Asp Tyr Asn Ala Glu Leu Asp Pro
    50                  55                  60

Val Thr Thr Glu Glu Gln Val Leu Asp Val Lys Gly Tyr Leu Ser Lys
65                  70                  75                  80

Val Arg Gly Ile Ser Glu Val Leu Ala Arg Arg His Met Lys Val Ala
                85                  90                  95

Phe Phe Gly Arg Thr Ser Asn Gly Lys Ser Thr Val Ile Asn Ala Met
            100                 105                 110

Leu Trp Asp Lys Val Leu Pro Ser Gly Ile Gly His Thr Thr Asn Cys
        115                 120                 125

Phe Leu Arg Val Glu Gly Thr Asp Gly His Glu Ala Phe Leu Leu Thr
    130                 135                 140

Glu Gly Ser Glu Glu Lys Arg Ser Ala Lys Thr Val Asn Gln Leu Ala
145                 150                 155                 160

His Ala Leu His Gln Asp Lys Gln Leu His Ala Gly Ser Leu Val Ser
                165                 170                 175

Val Met Trp Pro Asn Ser Lys Cys Pro Leu Leu Lys Asp Asp Leu Val
            180                 185                 190

Leu Met Asp Ser Pro Gly Ile Asp Val Thr Thr Glu Leu Asp Ser Trp
        195                 200                 205

Ile Asp Lys Phe Cys Leu Asp Ala Asp Val Phe Val Leu Val Ala Asn
    210                 215                 220

Ser Glu Ser Thr Leu Met Gln Thr Glu Lys His Phe Phe His Lys Val
225                 230                 235                 240

Ser Leu Ser Arg Pro Asn Ile Phe Ile Leu Asn Asn Arg Trp Asp Ala
                245                 250                 255

Ser Ala Ser Glu Pro Glu Tyr Met Glu Glu Val Arg Arg Gln His Met
            260                 265                 270

Glu Arg Cys Thr Ser Phe Leu Val Asp Glu Leu Gly Val Val Asp Arg
        275                 280                 285

Ser Gln Ala Gly Asp Arg Ile Phe Phe Val Ser Ala Lys Glu Val Leu
    290                 295                 300

Asn Ala Arg Ile Gln Lys Ala Gln Gly Met Pro Glu Gly Gly Gly Ala
305                 310                 315                 320

Glu Gly Phe Gln Val Arg Met Phe Glu Phe Gln Asn Phe Glu Arg Arg
                325                 330                 335

Phe Glu Glu Cys Ile Ser Gln Ser Ala Val Lys Thr Lys Phe Glu Gln
            340                 345                 350

His Thr Val Arg Ala Lys Gln Ile Ala Glu Ala Val Arg Leu Ile Met
        355                 360                 365

Asp Ser Leu His Met Ala Ala Arg Glu Gln Val Tyr Cys Glu Glu
    370                 375                 380

Met Arg Glu Glu Arg Gln Asp Arg Leu Lys Phe Ile Asp Lys Gln Leu
385                 390                 395                 400
```

```
Glu Leu Leu Ala Gln Asp Tyr Lys Leu Arg Ile Lys Gln Ile Thr Glu
            405                 410                 415

Glu Val Glu Arg Gln Val Ser Thr Ala Met Ala Glu Ile Arg Arg
        420                 425                 430

Leu Ser Val Leu Val Asp Asp Tyr Gln Met Asp Phe His Pro Ser Pro
        435                 440                 445

Val Val Leu Lys Val Tyr Lys Asn Glu Leu His Arg His Ile Glu Glu
450                 455                 460

Gly Leu Gly Arg Asn Met Ser Asp Arg Cys Ser Thr Ala Ile Thr Asn
465                 470                 475                 480

Ser Leu Gln Thr Met Gln Gln Asp Met Ile Asp Gly Leu Lys Pro Leu
                485                 490                 495

Leu Pro Val Ser Val Arg Ser Gln Ile Asp Met Leu Val Pro Arg Gln
                500                 505                 510

Cys Phe Ser Leu Asn Tyr Asp Leu Asn Cys Asp Lys Leu Cys Ala Asp
            515                 520                 525

Phe Gln Glu Asp Ile Glu Phe His Phe Ser Leu Gly Trp Thr Met Leu
        530                 535                 540

Val Asn Arg Phe Leu Gly Pro Lys Asn Ser Arg Arg Ala Leu Met Gly
545                 550                 555                 560

Tyr Asn Asp Gln Val Gln Arg Pro Ile Pro Leu Thr Pro Ala Asn Pro
                565                 570                 575

Ser Met Pro Pro Leu Pro Gln Gly Ser Leu Thr Gln Glu Glu Phe Met
            580                 585                 590

Val Ser Met Val Thr Gly Leu Ala Ser Leu Thr Ser Arg Thr Ser Met
        595                 600                 605

Gly Ile Leu Val Val Gly Val Val Trp Lys Ala Val Gly Trp Arg
610                 615                 620

Leu Ile Ala Leu Ser Phe Gly Gly Leu Leu Tyr Val Tyr Glu Arg Leu
625                 630                 635                 640

Thr Trp Thr Thr Lys Ala Lys Glu Arg Ala Phe Lys Arg Gln Phe Val
                645                 650                 655

Glu His Ala Ser Glu Lys Leu Gln Leu Val Ile Ser Tyr Thr Gly Ser
            660                 665                 670

Asn Cys Ser His Gln Val Gln Gln Glu Leu Ser Gly Thr Phe Ala His
            675                 680                 685

Leu Cys Gln Gln Val Asp Val Thr Arg Glu Asn Leu Glu Gln Glu Ile
        690                 695                 700

Ala Ala Met Asn Lys Lys Ile Glu Val Leu Asp Ser Leu Gln Ser Lys
705                 710                 715                 720

Ala Lys Leu Leu Arg Asn Lys Ala Gly Trp Leu Asp Ser Glu Leu Asn
                725                 730                 735

Met Phe Thr His Gln Tyr Leu Gln Pro Ser Arg
            740                 745

<210> SEQ ID NO 18
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 18

Arg Gln Ile Lys Ile Trp Phe Gln Asn Arg Arg Met Lys Trp Lys Lys
1               5                   10                  15
```

```
<210> SEQ ID NO 19
<211> LENGTH: 9
<212> TYPE: PRT
<213> ORGANISM: Human immunodeficiency virus 1

<400> SEQUENCE: 19

Arg Lys Lys Arg Arg Gln Arg Arg Arg
 1               5

<210> SEQ ID NO 20
<211> LENGTH: 11
<212> TYPE: PRT
<213> ORGANISM: Artificial Sequence
<220> FEATURE:
<223> OTHER INFORMATION: Modified HIV-1 Tat basic domain
<220> FEATURE:
<221> NAME/KEY: misc-feature
<222> LOCATION: 6
<223> OTHER INFORMATION: Xaa = Pyrrolysine (Pyl/O)

<400> SEQUENCE: 20

Arg Lys Lys Arg Arg Xaa Arg Arg Arg Gly Cys
 1               5                  10

<210> SEQ ID NO 21
<211> LENGTH: 13
<212> TYPE: DNA
<213> ORGANISM: Homo sapiens

<400> SEQUENCE: 21
ccgccaagaa gcg                                                          13

<210> SEQ ID NO 22
<211> LENGTH: 100
<212> TYPE: DNA
<213> ORGANISM: Homo sapiens

<400> SEQUENCE: 22
gcgtgcacac gcgcgtagac ttcccccgca agtcactcgt tagcccgcca agaagcgacc      60
cctccggggc gagctgagcg gcgtggcgcg ggggcgtcat                            100

<210> SEQ ID NO 23
<211> LENGTH: 101
<212> TYPE: DNA
<213> ORGANISM: Homo sapiens

<400> SEQUENCE: 23
acgtgcatac gcacgtagac attccccgct tcccactcca aagtccgcca agaagcgtat     60
cccgctgagc ggcgtggcgc gggggcgtca tccgtcagct c                         101

<210> SEQ ID NO 24
<211> LENGTH: 58
<212> TYPE: DNA
<213> ORGANISM: Homo sapiens

<400> SEQUENCE: 24
acttcccccg caagtcactc gttagcccgc caagaagcga cccctccggg gcgagctg       58

<210> SEQ ID NO 25
<211> LENGTH: 9
<212> TYPE: PRT
<213> ORGANISM: Artificial Sequence
<220> FEATURE:
```

```
<223> OTHER INFORMATION: Synthetically generated peptide

<400> SEQUENCE: 25

Leu Phe Ala Cys Gly Ser Ser His Lys
 1               5

<210> SEQ ID NO 26
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 26

Cys Gly Ser Ser His
 1               5

<210> SEQ ID NO 27
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 27

Gly Ser Ser His Lys
 1               5

<210> SEQ ID NO 28
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 28

Lys Lys Trp Lys Met Arg Arg Asn Gln Phe Trp Val Lys Val Gln Arg
 1               5                  10                  15

Leu Phe Ala Cys Gly Ser Ser His Lys
            20                  25

<210> SEQ ID NO 29
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 29

Lys Lys Trp Lys Met Arg Arg Asn Gln Phe Trp Val Lys Val Gln Arg
 1               5                  10                  15

Cys Gly Ser Ser His
            20

<210> SEQ ID NO 30
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 30

Lys Lys Trp Lys Met Arg Arg Asn Gln Phe Trp Val Lys Val Gln Arg
 1               5                  10                  15

Gly Ser Ser His Lys
```

```
<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
aaaaagaatt cctggcgctg cgctgcggct c                          31

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
aaaaactcga gcagattagc tcaactggcc acagtc                     36

<210> SEQ ID NO 33
<211> LENGTH: 39
<212> TYPE: DNA
<213> ORGANISM: Artificial Sequence
<220> FEATURE:
<223> OTHER INFORMATION: Primer

<400> SEQUENCE: 33
aaaaagaatt cggcggcatg tgcagcaagg gctccggcg                  39

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
aaaaactcga gcagattagc tcaactggcc acagtc                     36

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
aaaaaggatc cgtacgacat ggcgcgcga                             29

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
aaaaaggatc cagcacgcag accgccgagg                            30

<210> SEQ ID NO 37
<211> LENGTH: 32
<212> TYPE: DNA
<213> ORGANISM: Artificial Sequence
```

-continued

```
<220> FEATURE:
<223> OTHER INFORMATION: Primer

<400> SEQUENCE: 37
aaaaactcga gctagtgtcg ctccagggcc tt                                32

<210> SEQ ID NO 38
<211> LENGTH: 34
<212> TYPE: DNA
<213> ORGANISM: Artificial Sequence
<220> FEATURE:
<223> OTHER INFORMATION: Primer

<400> SEQUENCE: 38
aaaaaggatc caggaggatg ttctcgtccg tagc                              34

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
aaaaactcga gctactcagt taacccaagc ttcttcttc                         39

<210> SEQ ID NO 40
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 40

Arg Gln Ile Lys Ile Trp Phe Gln Asn Arg Arg Met Lys Trp Lys Lys
 1               5                  10                  15

Cys

<210> SEQ ID NO 41
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 41

Arg Arg Ile Val Val Leu His Gly Tyr Gly Ala Val Lys Glu Val Leu
 1               5                  10                  15

Leu Asn His Lys
             20

<210> SEQ ID NO 42
<211> LENGTH: 22
<212> TYPE: PRT
<213> ORGANISM: Artificial Sequence
<220> FEATURE:
<223> OTHER INFORMATION: Synthetically generated peptide

<400> SEQUENCE: 42

Met Leu Ser Leu Arg Gln Asp Ile Arg Phe Phe Lys Pro Ala Thr Arg
 1               5                  10                  15

Thr Leu Cys Ser Ser Arg
             20
```

MITOCHONDRIA-TARGETED ANTI-TUMOR AGENTS

CLAIM OF PRIORITY

This application is a continuation application of U.S. patent application Ser. No. 13/905,008, filed on May 29, 2013 (now abandoned), which is a continuation of U.S. patent application Ser. No. 12/208,207, filed on Sep. 10, 2008 (issued as U.S. Pat. No. 8,466,140), which claims the benefit of U.S. Provisional Patent Application Ser. No. 60/993,195, filed on Sep. 10, 2007, the entire contents of each of these applications are hereby incorporated by reference.

SEQUENCE LISTING

The document includes a sequence listing in electronic format submitted to the United States Patent and Trademark Office via the electronic filing system. The ASCII text file, which is incorporated-by-reference herein, is titled "SequenceListing-0319003.txt," was created on Mar. 8, 2016, and has a size of 16.1 kilobytes.

FEDERALLY SPONSORED RESEARCH OR DEVELOPMENT

This invention was made with Government support under Grant Nos. HL54131, CA78810, and CA90917, awarded by the National Institutes of Health. The Government has certain rights in the invention.

TECHNICAL FIELD

This invention relates to mitochondria-targeted inhibitors of molecular chaperones, e.g., Heat Shock Protein 90 (Hsp90), Hsp60, Heat Shock 70 kDa Protein 9 (HSPA9/mortalin), or TNF Receptor-Associated Protein 1 (TRAP-1), used as anti-tumor agents, and methods of making and using the same for the treatment of disorders associated with unwanted cell proliferation.

BACKGROUND

Tumor cells exhibit an enhanced ability to survive and proliferate in highly unfavorable environments. They have been shown to down-regulate many of the cellular pathways that prevent normal (i.e., non-cancerous) cells from dividing in a hostile environment, and they also inactivate apoptotic pathways that bring about cell death in many normal tissues under adverse conditions. Tumor cells are also believed to up-regulate pathways required to maintain active proliferation. For example, many tumor cells activate the cellular stress-response pathway that allows tumor cells to synthesize and maintain the protein machinery they need to continue proliferating. The activated stress response in tumors includes up-regulation of heat-shock proteins (Hsps), which are ATPase-directed molecular chaperones. In particular, Hsp90 is upregulated in many cancerous tissues. Hsp90 controls the balance between folding/maturation and proteasomal destruction of a restricted number of client proteins, some of which are involved in signal transduction and cell proliferation.

SUMMARY

The present invention is based, at least in part, on the discovery that the molecular chaperones Hsp90, Hsp60, and TRAP-1 are found at increased levels in mitochondria of tumor cells as compared to normal cells, and that inhibition of molecular chaperones in tumor cell mitochondria using mitochondrial-targeted chaperone inhibitors results in tumor cell death.

In one aspect, the invention provides compositions having the formula:

A-B, wherein A is a molecular chaperone inhibitor and B is a mitochondria-penetrating moiety and A and B are linked, optionally by a linking moiety; or a pharmaceutically acceptable salt thereof. However, if A is Shepherdin or a fragment thereof, then B is not Antennapedia helix III homeodomain cell-penetrating peptide (ANT) or a fragment thereof.

In some embodiments, A is or includes a small molecule, e.g., an Ansamycin class Hsp90 inhibitor; a geldanamycin analogue; a purine-scaffold class Hsp90 inhibitor, a resorcinol; or a macrolactone-Hsp90 inhibitor; a peptide inhibitor of Hsp90, e.g., a Shepherdin peptide including SEQ ID NO:2 (His-Ser-Ser-Gly-Cys); or a peptide including a sequence that is at least 95% identical to SEQ ID NO:1, that binds to and inhibits Hsp90. In some preferred embodiments, A is or includes radicicol or an analog thereof; a purine inhibitor of Hsp90; 17-allylamino-demethoxygeldamycin (17-AAG); 17-dimethylaminogeldanamycin; 17-GMB-APA-GA (a maleimido derivative of geldanamycin that enables the conjugation of GA to a polypeptide); 17-(Dimethylaminoethylamino)-17-demethoxygeldanamycin (17-DMAG); 17-[2-(Pyrrolidin-1-yl)ethyl]aminno-17-demethoxygeldanamycin (17-AEP-GA); or 17-(Dimethylaminopropylamino)-17-demethoxygeldanamycin (17-DMAP-GA).

In some embodiments, the cationic mitochondrial-penetrating moiety, B, includes:

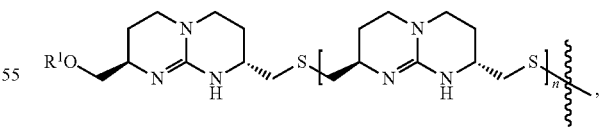

where $R^1$ is H, alkyl, alkenyl, alkynyl, haloalkyl, aryl, arylalkyl, or $R^a R^b R^c Si$; $R^a$, $R^b$, and $R^c$ are independently selected from alkyl or aryl; and n can be 0, 1, 2, 3, 4, 5, or 6.

In some embodiments, the cationic mitochondrial-penetrating moiety, B, includes

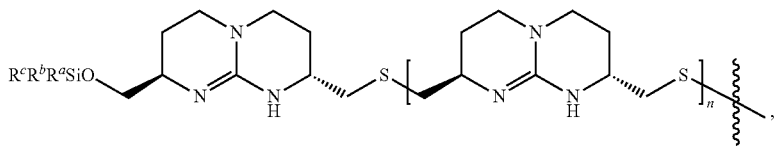

where, $R^a$, $R^b$, and $R^c$ are independently selected from alkyl or aryl; and n can be 1, 2, or 3.

In some embodiments, B is a mitochondria penetrating peptide, e.g., a mitofusin peptide, a mitochondrial targeting signal peptide, Antennapedia helix III homeodomain cell-penetrating peptide (ANT) (e.g., comprising SEQ ID NO:18), HIV-1 Tat basic domain (e.g., comprising SEQ ID NO:19 or 20); VP22 peptide, or Pep-1 peptide; an RNA mitochondrial penetrating signal (e.g., comprising SEQ ID NO:21, 22, 23, or 24); or selected from the group consisting of guanidine-rich peptoids, guanidine-rich polycarbamates, β-oligoarginines, and proline-rich dendrimers. In some embodiments, B is a tetraguanidinium, triiguanidinium, diguanidinium, or monoguanidinium compound, or a triphenylphosphonium compound.

In some embodiments, the cationic mitochondrial-penetrating moiety, B, includes $(aryl)_3P$—.

In some embodiments, the cationic mitochondrial-penetrating moiety, B, includes Rhodamine 123:

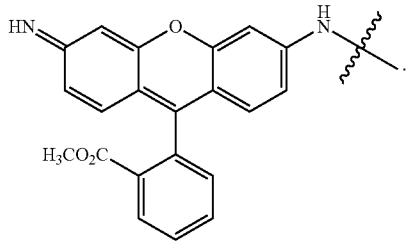 [SMILES: *Nc1ccc2c(-c3ccccc3C(=O)OC)c3ccc(=N)cc-3oc2c1]

In some embodiments of the composition, the molecular chaperone inhibitor, A, includes geldanamycin analogues:

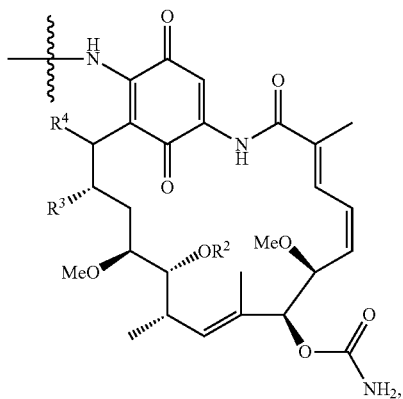

where, $R^2$ is H, alkyl, aryl, or arylalkyl; $R^3$ is H, alkyl; and $R^4$ is H, alkyl, alkenyl, aryl, arylalkyl, $OR^d$, wherein $R^d$ is H, alkyl, or arylalkyl.

In some embodiments of the composition, $R^2$ is H or alkyl; $R^3$ is H, alkyl; and $R^4$ is H, or $OR^d$, wherein $R^d$ is H, alkyl.

In some embodiments of the composition, $R^2$ is H; $R^3$ is methyl; and $R^4$ is H.

In some embodiments of the composition, B is a mitochondria penetrating peptide, e.g., a mitofusin peptide, a mitochondrial targeting signal peptide, Antennapedia helix III homeodomain cell-penetrating peptide (ANT) (e.g., comprising SEQ ID NO:18), HIV-1 Tat basic domain (e.g., comprising SEQ ID NO:19 or 20); VP22 peptide, or Pep-1 peptide; an RNA mitochondrial penetrating signal (e.g., comprising SEQ ID NO:21, 22, 23, or 24); or selected from the group consisting of guanidine-rich peptoids, guanidine-rich polycarbamates, β-oligoarginines, and proline-rich dendrimers. a phosphonium salt, e.g., methyltriphenylphosphonium and tetraphenylphosphonium. In some embodiments of the composition, B is or includes ANT or a mitochondrial-penetrating fragment thereof. In some embodiments of the composition, B is a tetraguanidinium, triiguanidinium, diguanidinium, or monoguanidinium compound, or a triphenylphosphonium compound.

In some embodiments, the compositions include a linking moiety between A and B, e.g., a peptide linker or a chemical linker.

In some embodiments, the linker moiety is divalent and can be selected from the group consisting of alkylene, alkenylene, alkynylene, cycloalkylene, arylene, heteroarylene, and peptide linker, wherein any two adjacent carbon-carbon bonds of said alkylene, alkenylene, or alkynylene, can be optionally replaced with one or more of O, NH, S, $PR^e$, $C(O)NR^f$, arylene, heterocycloalkylene, or heteroarylene; wherein $R^e$ and $R^f$ are independently selected from alkyl or aryl.

In some embodiments, the linker moiety is:

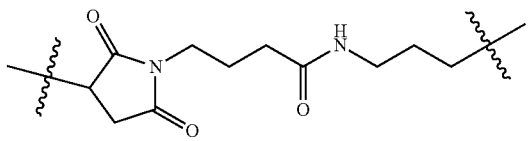

In some embodiments, the linker moiety is alkylene

In some embodiments, the linker moiety is alkylene with six carbon atoms.

In some embodiments, the compositions include compounds of the formula:

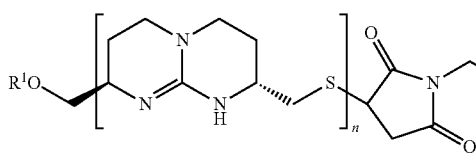

wherein, R¹ is H, alkyl, alkenyl, alkynyl, haloalkyl, aryl, arylalkyl, or $R^aR^bR^cSi$; R² is H, alkyl, aryl, or arylalkyl; R³ is H, alkyl; R⁴ is H, alkyl, alkenyl, aryl, arylalkyl, $OR^d$, wherein $R^d$ is H, alkyl, or arylalkyl; $R^a$, $R^b$, and $R^c$ are independently selected from alkyl or aryl; and n is an integer between 1 and 10, inclusive; or a pharmaceutically acceptable salt thereof.

In some embodiments, the salt is a hexafluorophosphate salt

In some embodiments, R¹ is $R^aR^bR^cSi$, $R^a$, $R^b$, and $R^c$ are independently selected from alkyl or aryl; R² is H; R³ is H, alkyl; R⁴ is H; and n is 1, 2, 3, or 4.

In some embodiments, the compounds can be of the formula:

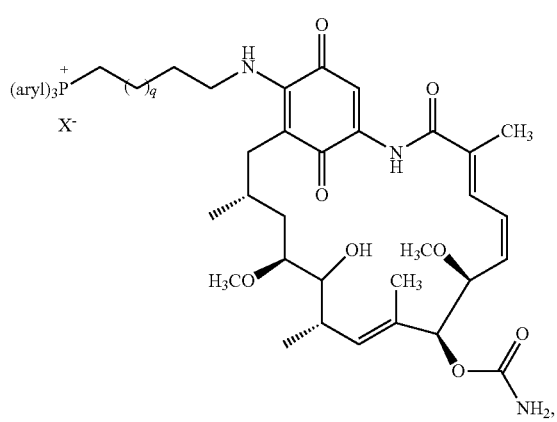

wherein, q is 1, 2, 3, 4, 5, or 6.

In some embodiments, q is 3.

In some embodiments, aryl is phenyl.

In some embodiments, aryl is phenyl and q is 3.

In some embodiments, X can be hexafluorophosphate.

In some embodiments, the compound can be:

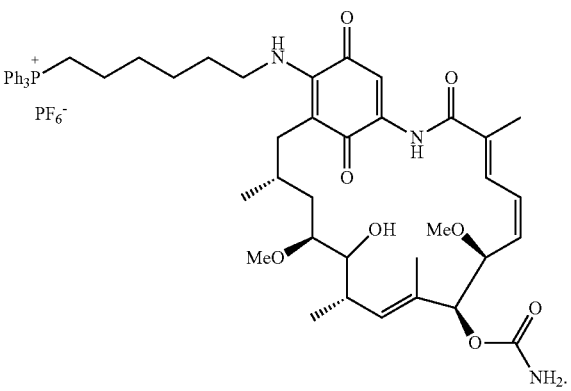

In a further aspect, the invention includes methods for inducing cancer cell death or tumor cell death, e.g., in a subject, e.g., a mammal, e.g., a human or non-human mammal, the method comprising administering to the subject a mitochondrial-targeted chaperone inhibitor described herein an amount sufficient to induce cancer cell death.

In another aspect, the invention provides methods for inducing cancer cell death or tumor cell death, e.g., in a subject, e.g., a mammal, e.g., a human or non-human mammal. The methods include identifying a subject having cancer or a tumor, e.g., cancer or a tumor comprising cancer cells or tumor cells; and determining whether cells of said cancer or tumor have increased mitochondrial concentrations of a chaperone, e.g., Hsp90 or Trap-1, e.g., as compared to a control, e.g., a normal, non-tumor, non-cancer cell. If the subject has increased mitochondrial levels of said chaperone, then the methods include administering to the mammal a mitochondrial-targeted chaperone inhibitor comprising the formula:

A-B, wherein A is a chaperone inhibitor and B is a mitochondria-penetrating moiety and A and B are linked, optionally by a linking moiety, e.g., as described herein.

In yet a further aspect, the invention provides methods for identifying a candidate agent for inhibiting chaperone activity. The methods include providing a sample comprising at least one chaperone and Cyclophilin D; contacting the sample with a test agent; and detecting binding of the Chaperone and Cyclophilin D in the sample in the presence and absence of the test agent. A test agent that inhibits binding is a candidate agent for inhibiting Chaperone activity. In some embodiments, the chaperone is Hsp60, HspA9, Hsp90, or TRAP-1.

"Cancer," as the term is used herein, refers to a disease characterized by uncontrolled, abnormal growth of cells. A "cancer cell" is cell that divides and reproduces abnormally with uncontrolled growth. This cell can break away from the site of its origin (e.g., a tumor) and travel to other parts of the body and set up another site (e.g., another tumor), in a process referred to as metastasis. A "tumor" is an abnormal mass of tissue that results from excessive cell division that is uncontrolled and progressive, and is also referred to as a neoplasm. Tumors can be either benign (not cancerous) or malignant. The methods described herein are useful for the treatment of cancer and tumor cells, i.e., both malignant and benign tumors as well as cancers with no solid tumors (such as hematopoietic cancers), so long as the cells to be treated have mitochondrial localization of the chaperones as described herein.

Molecular chaperones are any of a group of proteins that are involved in the correct intracellular folding and assembly of polypeptides without being components of the final structure. Molecular chaperones are found in bacteria, mitochondria, and the eukaryotic cytosol. Herein, "molecular chaperones" and "chaperones" are used interchangeably.

Herein, the term "mitochondriotropic" is used interchangeably with "mitochondrial targeting" and "mitochondrial-penetrating".

Herein, the term "mitochondriotropic agent" refers to compositions having the formula A-B as described herein, wherein the agent inhibits chaperone activity and localizes to mitochondria.

As used herein, "Gamitrinib" refers to a geldanamycin analogue, e.g., 17-AAG, conjugated via an amino group at the C17 position via a linker to a mitochondrial penetrating moiety, for example, a tetraguanidinium (G4), triguanidinium (G3), diguanidinium (G2), monoguanidinium (G1), or a triphenylphosphonium (TPP) moiety. Throughout this application, the mitochondrial penetrating moiety that is part of a particular Gamitrinib is sometimes indicated. For example, Gamitrinib-G4 refers to a Gamitrinib in which a tetraguanidinium moiety is present. For example, Gamitrinib-TPP refers to a Gamitrinib in which a triphnylphosphonium moiety is present. Also throughout this application, the use of the plural form "Gamitrinibs" indicates one or more of the following: Gamitrinib-G4, Gamitrinib-G3, Gamitrinib-G2, Gamitrinib-G1, and Gamitrinib-TPP.

Although the following description is, at times, directed to the molecular chaperone Hsp90, it should be understood that the description can be generalized to structurally related molecular chaperones that are overexpressed in the mitochondria of cancer cells, e.g., TRAP-1 (Song et al., J. Biol. Chem., 270:3574-3581 (1995); Cechetto and Gupta, Experimental Cell Research, 260:30-39 (2000)); Heat Shock 60 kDa Protein 1 (Hsp60/HspD1) (Singh et al., Biochem. Biophys. Res. Commun. 169 (2), 391-396 (1990)); Bross et al., J. Hum. Genet. 52 (1), 56-65 (2007)); and Heat shock 70 kDa protein 9 (HSPA9/mortalin) (Domanico et al., Mol. Cell. Biol. 13 (6), 3598-3610 (1993); Bhattacharyya et al., J. Biol. Chem. 270 (4), 1705-1710 (1995); Kaul et al., FEBS Lett. 361 (2-3), 269-272 (1995)).

In one aspect, the present invention provides molecular chaperone inhibitors that are targeted to the mitochondria, i.e., that penetrate the mitochondrial membrane and accumulate there. Chaperone inhibitors can be targeted to the mitochondria via association with a mitochondrial penetrating moiety. The molecular chaperone inhibitor may be, for example, a protein, or chaperone binding fragment thereof, that binds to a chaperone protein. For example, certain Inhibitors of Apoptosis Proteins (IAPB) can be used. IAPB are a family of antiapoptotic proteins (Schimmer, Can. Res. 64:7183-7190 (2004)); useful IAPB include those that bind to the molecular chaperone Hsp90. Fragments of these and other proteins that naturally bind to molecular chaperones are part of this invention. Peptidomimetics of these and other peptides or proteins that naturally bind to and inhibit molecular chaperones can also be used.

The chaperone inhibitor can also be a small molecule, the mitochondria targeted chaperone inhibitor described herein, e.g., a small molecule identified through screening methods described herein.

The molecular chaperone inhibitors are linked to a mitochondrial penetrating moiety. The mitochondrial penetrating moiety can be, for example, a basic or positively charged peptide sequence, e.g., from the third helix of the Antennapedia homeodomain (ANT). In some embodiments, the mitochondrial penetrating moiety can be a tetraguanidium compound as described in Fernandez-Carneado et al. (J. Am. Chem. Soc., 127:869-874 (2005)).

The link between the molecular chaperone inhibitor and the mitochondrial penetrating moiety can be a covalent bond, e.g., a peptide bond or a thioether bond. In some embodiments, e.g., one or both of the chaperone inhibitor or the mitochondrial penetrating moiety is non-peptidic, e.g., a small molecule, the molecular chaperone inhibitor and mitochondrial penetrating moiety are joined through a chemical linker. In some embodiments, the link between a molecular chaperone inhibitor and a mitochondrial penetrating moiety can be a non-covalent interaction, e.g., an ionic interaction. In another aspect, the present invention also features methods for identifying chaperone inhibitors. In particular, this invention features methods for identifying candidate compounds that disrupt the interaction between Hsp90 and Cyclophilin D (CypD), between Hsp60 and CypD, or between TRAP-1 and CypD.

The invention provides several advantages. For example, the increased expression of the chaperones in mitochondria, as compared to normal cells as described herein, provide a targeted approach that can be used to kill tumor cells without harming normal cells, thus minimizing side effects and increasing efficacy. In addition, a wide variety of tumor and cancer cell types show mitochondrial accumulation of chaperones, thus, numerous types of tumors and cancers that can be treated by the methods described herein.

This invention provides mitochondriotropic agents (e.g., mitochondrially targeted chaperone inhibitors) that are advantageous over the art. These agents are localized to mitochondria with increased efficiency and selectively induce mitochondrial collapse and cell death in cells that show mitochondrial accumulation of chaperones (e.g., cancer cells). These agents have maximal effect on the function of mitochondrially-localized chaperones present in transformed cells (e.g., cancer cells) while having minimal effect on normal chaperone function (e.g., Hsp90 function in normal or non-transformed cells). Thus, these agents are ideal candidates for cancer therapy as they are expected to have lower toxicity than presently known chaperone inhibitors, which do not specifically inhibit mitochondrially-localized chaperones.

For example, Gamitrinibs as described herein are novel, small molecule anticancer agents suitable for testing in humans. Although applicants do not wish to be bound by theory, the combinatorial design of Gamitrinibs efficiently targets them to mitochondria, thereby maximizing their cytotoxic effects on tumor cells while minimizing their effects on non-tumor or normal cells. This is because of the presence of a mitochondrial pool of chaperones (e.g., Hsp90 and TRAP1) in tumor cells that is vital to tumor cell survival but that is not present in normal cells or has negligible effect on normal cell survival. In addition, the combinatorial design of Gamitrinibs minimizes their effects on non-tumor or normal cells which express chaperones predominantly in the cytosol. Compared to current Hsp90 inhibitors (see, e.g., Drysdale et al., "Targeting Hsp90 for the treatment of cancer," Curr Opin Drug Discov Devel, 9:483-495 (2006)), Gamitrinibs have improved cytotoxic activity on tumor cells, supported by in vitro and in vivo results. Another key advantage is that these agents do not affect the general homeostatic functions of Hsp90 in the cytosol, and therefore do not elicit potentially compensatory survival signals seen with general Hsp90 antagonists, e.g. Hsp70 induction ((see, e.g., Drysdale et al., (2006) supra). Because mitochondrial Hsp90 chaperones are absent in most normal tissues (as demonstrated herein), Gamitrinibs are selective for tumor cells and have reduced toxicity for normal cells, making Gamitrinibs favored candidates for anti-cancer therapy. In addition, tumor-associated Hsp90 binds ATPase pocket antagonists with higher affinity compared to normal cells (see, e.g., Kamal et al., Nature, 425:407-410 (2003)), and this may further protect normal organs with low levels of mitochondrial Hsp90, i.e. brain, from Gamitrinib-based therapy. Following the paradigm of Gamitrinibs, other chaperone inhibitors, e.g., the purine inhibitors or resorcinol inhibitors (e.g., piperazinyl, morpholino and piperidyl derivatives of the pyrazole-based resorcinol Hsp90 inhibitor CCT018159), may be used to target cancer cells (see, e.g., Sharp et al., Cancer Res. 67 (5):2206-16 (2007); Sharp et al., Mol Cancer Ther. 6 (4):1198-1211 (2007); Eccles et al., Cancer Res. 68 (8):2850-60 (2008); Strausberg et al., Nature, 429:469-474 (2004); Butcher, Nat Rev Drug Discov 4, 461-467 (2005); Philips, Biochem Soc Trans, 33:657-661 (2005)).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a pair of immunoblots showing that the Hsp90-like chaperone TRAP-1 localizes to mitochondria at increased levels in tumor cells relative to normal cells. Immunoblots of TRAP-1 and the mitochondrial marker Cox-IV in cytosolic or mitochondrial extracts purified from the indicated tumor cell types (top panel), or mitochondria from normal mouse organs (bottom panel) are shown. β-Actin expression is shown as a control in the top panel.

FIGS. 1B-I are images of immunohistochemically stained primary tissue samples showing in vivo expression of TRAP-1 in specimens of normal pancreas (B), breast (D), colon (F) or lung (H), or cases of adenocarcinoma of pancreas (C), breast (E), colon (G), or lung (I).

FIG. 1J is a series of three related immunoblots of mitochondrial or cytosolic extracts showing that Hsp90 localizes to mitochondria in tumor cells. Cox-IV expression levels and β-actin expression levels are shown as controls.

FIGS. 1K-L are electron micrographs showing that an antibody to Hsp90 localizes to isolated HeLa cell mitochondria (FIG. 1K) but that a non-specific antibody does not localize to isolated HeLa cell mitochondria (FIG. 1L).

FIG. 1M is a series of six related immunoblots of total cytosol extracts (TCE) or isolated mitochondria (PK-treated) or cytosolic extracts from HeLa cells showing expression levels of Calnexin, Lamp-1, GAPDH, Cox-IV, TRAP-1, and Hsp90.

FIGS. 3A-D are fluorescence microscopy images of mitochondrial accumulation of FITC-conjugated Shepherdin with (A, C) or without (B) Antennapedia cell-penetrating sequence (ANT) or scrambled peptidomimetic with ANT (D) incubated in the presence (A, B, D) or absence (C) of HeLa cell mitochondria showing that both Shepherdin with ANT (Sheph-ANT) and cell permeable scrambled peptidomimetic with ANT (Scram-ANT) accumulate in mitochondria.

FIG. 3E is a bar graph of the fluorescence intensity quantified in isolated mitochondrial fractions following treatment of cells with FITC-conjugated Sheph-ANT or FITC-conjugated Scram-ANT, showing that Sheph-ANT and Scram-ANT accumulate to similar levels in mitochondria.

FIG. 3F is a bar graph of fluorescence intensity quantified in extracts of mitochondria and mitochondrial fractions isolated from HeLa cell mitochondria incubated with FITC-conjugated Shepherdin (Sheph), or FITC-conjugated Shepherdin with ANT (Sheph-ANT), showing that Sheph-ANT accumulates in the mitochondria, outer membrane/inner membrane space (OM+IMS), and inner membrane/matrix (IM+Matrix). Untreated sample (None) is a control.

FIG. 5A and FIG. 5B are confocal microscopy images of HeLa cells doubled-labeled with a mitochondrial stain (MitoTracker) and FITC-conjugated Sheph-ANT (FIG. 5A) or FITC-conjugated Scram-ANT (FIG. 5B) and analyzed by image merging.

FIG. 5C is a bar graph showing fluorescence intensity in total cell extracts (TCE), cytosolic extracts, or mitochondrial extracts of HeLa cells treated with FITC-conjugated Sheph-ANT or FITC-conjugated Scram-ANT.

FIG. 5D is a line graph showing mitochondrial membrane potential over time following the addition of Sheph-ANT (solid line), 17-AAG (dotted line), or Scram-ANT (broken line) in JC-1-loaded Raji cells.

FIG. 5E panels are immunoblots of cytosolic extracts from HeLa cells incubated with different concentration of 17-AAG, showing cytochrome c and β-actin as a control.

FIG. 7C is a pair of sets of two immunoblots of cytochrome c released from isolated HeLa cell mitochondria (top set of two panels) or isolated mouse-liver mitochondria (bottom set of two panels) treated with ANT-GA or the uncoupled mixture of GA/ANT.

FIG. 7D is a line graph showing percent viability, as determined by MTT, of HeLa cells incubated with GA, ANT-GA, or GA/ANT at varying concentrations.

FIG. 7E is a line graph showing percent viability, as determined by MTT, of primary human fibroblasts WS-1 (black), HGF (purple), or HFF (green), treated with ANT-GA (solid squares) or GA/ANT (open circles). Prostate cancer PC3 cells (blue) are a control.

FIG. 10B, bottom panel, is a Coomassie stain of the gel used in the experiment.

FIG. 10C, bottom panel, is a Coomassie stain of the gel used in the experiment.

FIG. 12C is a pair of mass spectrographs. The upper panel is a mass spectrum of the coupling reaction performed to produce ANT-GA showing the peak for 17-GMP-APA-GA at arrow. The lower panel is a mass spectrum of the coupling reaction of performed to produce ANT-GA showing the peaks for ANT and ANT-GA at arrows.

FIG. 12D is an immunoblot showing Akt expression (upper panel) in HeLa cells treated with ANT-GA (middle lane) or the uncoupled mixture GA/ANT (right lane). Untreated HeLa cells were used as a control (left lane). β-actin was used as a control (bottom panel, lanes as in the top panel).

FIG. 13A is a pair of Western blots showing Hsp60 and COX-IV expression in isolated cytosolic (C) or mitochondrial (M) fractions from MCF-7 or HCT116 cells (top panel), or primary WS-1 or HFF human fibroblasts (bottom panel).

FIG. 14 is an informal sequence listing of the sequences set forth herein.

FIG. 16A is a line graph showing mitochondrial inner membrane potential over time in TMRM-loaded mitochondria treated with Gamitrinib-G1 ("G1"), Gamitrinib-G2 ("G2"), Gamitrinib-G3 ("G3"), Gamitrinib-G4 ("G4"), Gamitrinib-TPP ("TPP"), GA, or 17-AAG (at a concentration of 1 µM) and analyzed for fluorescence emission.

FIG. 16B, left panel is a line graph showing mitochondrial inner membrane potential over time in TMRM-loaded mitochondria incubated with 17-AAG mixed with tetraguanidinium (17-AAG+TG-OH), 17-AAG and 1 µM Cyclosporin A ("17-AAG+CsA"), 1.5 µM Gamitrinib-G4 ("G4"), 1.5 µM Gamitrinib-G4 and 1 µM Cyclosporin A ("G4+CsA"). The right panel is a line graph showing mitochondrial inner membrane potential over time in TMRM-loaded mitochondria incubated with GA mixed with triphenylphosphonium ("GA+TPP-OH"), GA mixed with triphenylphosphonium and 1 µM Cyclosporin A ("GA+TPP-OH+CsA"), triphenylphosphonium by itself ("TPP") and triphenylphosphonium and 1 µM Cyclosporin A ("TPP+CsA"). Arrows indicate point of addition.

FIG. 18B shows two images labeled "Vehicle" and "G4" of internucleosomal DNA fragmentation in tumor specimens from vehicle ("Vehicle") or Gamitrinib-G4 ("G4") treated tumors as visualized in situ by TUNEL. The bar graph at bottom shows quantification of positive cells. Magnification, ×400. ***, $p<0.0001$.

treated with vehicle or Gamitrinib-G4 ("G4") at 2 mg/kg twice daily i.p. (HL-60) for the duration of treatment. Arrow, start of treatment.

Figure 20A:
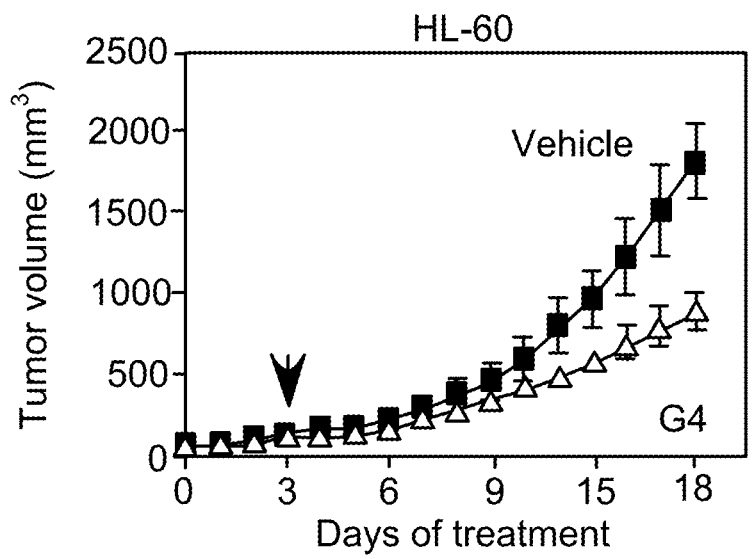
FIG. 20A is a line graph showing human acute leukemia HL-60 tumor volume over time (2/mouse, 6 tumors/group)
Figure 20B:
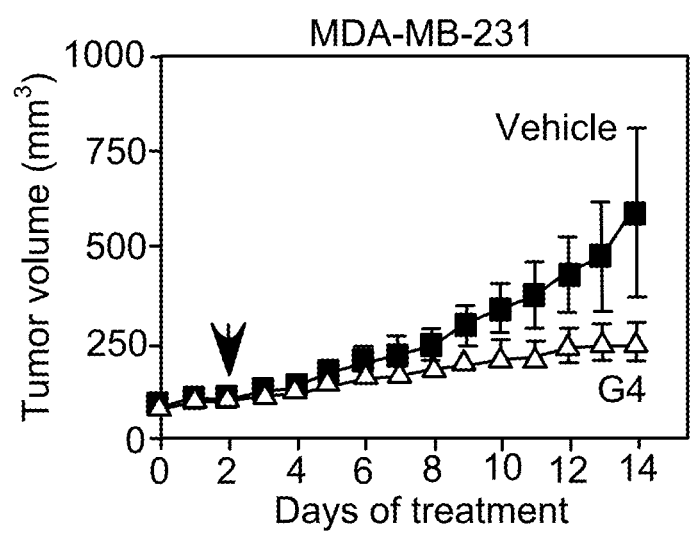

FIG. 20B is a line graph showing human breast adenocarcinoma MDA-MB-231 tumor volume over time (2/mouse, 6 tumors/group) treated with vehicle or Gamitrinib-G4 ("G4") with a dose escalation regimen (MDA-MB-231) starting at 2 mg/kg twice daily (day 0-2), 2.5 mg/kg twice daily (day 3-5), and 3 mg/kg twice daily for the duration of treatment. Arrow, start of treatment.

DETAILED DESCRIPTION

Mitochondria play a critical role in cell survival and cell death (Pandey et al., EMBO J., 19:4310-4322 (2000); Green and Kroemer, Science, 305:626-629, (2004)). Dysfunction and loss of integrity of these organelles are molecular prerequisites of multiple cell death pathways, characterized by increased permeability of the inner mitochondrial membrane, loss of membrane potential, swelling of the matrix, and ultimately rupture of the outer membrane with release of apoptogenic proteins, i.e., cytochrome c, in the cytosol (Green and Kroemer, Science, 305:626-629, (2004)). How this process, known as "mitochondrial permeability transition," is regulated is not completely understood (Green and Kroemer, Science, 305:626-629, (2004)); components of the permeability transition pore, including the voltage-dependent anion channel (VDAC-1), the adenine nucleotide translocator (ANT), or the immunophilin Cyclophilin D (CypD), were found to be either dispensable (Kokoszka et al., Nature, 427:461-1465, (2004); Krauskopf et al., Biochim. Biophys. Acta, 1757:590-595, (2006)), or implicated in some, but not all forms of mitochondrial cell death (Baines et al., Nature, 434:658-662, (2005); Nakagawa et al., Nature, 434:652-658, (2005)).

The present invention is based, at least in part, on the discovery that the molecular chaperones Hsp60, Hsp90 and TRAP-1 are found at increased levels in mitochondria of tumor cells, and that inhibition of molecular chaperones in tumor cell mitochondria using mitochondrial-targeted chaperone inhibitors results in cancer cell death. Without wishing to be bound by theory, the inhibition of these mitochondrial chaperones may result in the activation of mitochondrial permeability transition with collapse of mitochondrial function, including loss of mitochondrial membrane potential and release of cytochrome c, which leads to cell death.

Thus, described herein are mitochondriotropic agents that include a chaperone inhibitor, e.g., an HSPA9, Hsp60, Hsp90 or TRAP-1 inhibitor, and a mitochondrial penetrating moiety, optionally with an intervening linker, and methods of making and using these compositions to treat disorders associated with aberrant cellular proliferation, e.g., cancer and tumors, e.g., to kill cancer and tumor cells, e.g., in vivo and in vitro. Also described herein are compositions containing these mitochondriotropic agents.

I. Molecular Chaperones

Molecular chaperones, especially members of the Heat Shock Protein (Hsp) gene family (Lindquist and Craig, Annu. Rev. Genet. 1988; 22:631-77), assist in protein folding quality control, protein degradation, and protein trafficking among subcellular compartments (Hartl and Hayer-Hartl, Science 2002; 295:1852-8). This involves periodic cycles of ATPase activity, recruitment of additional chaperones, and compartmentalization in subcellular microdomains, including mitochondria (Young et al., Cell 2003; 112:41-50). Molecular chaperones have often been associated with enhanced cell survival (Beere, J Cell Sci 2004; 117:2641-51), via suppression of apoptosome-initiated mitochondrial cell death (Paul et al., Mol Cell Biol 2002; 22:816-34), increased stability of survival effectors (Sato et al., Proc Natl Acad Sci USA 2000; 97:10832-7), and inactivation of p53 (Wadhwa et al., J Biol Chem 1998; 273: 29586-91). As described herein, the chaperone anti-apoptotic function play a central role in tumor cell maintenance and can be selectively targeted to kill cancer cells. See also: Whitesell et al., Nat Rev Cancer 2005; 5:761-72; and Isaacs et al., Cancer Cell 2003; 3:213-7.

The following is a brief description of some of the molecular chaperones that can be targeted using the present methods. In some embodiments, a molecular chaperone polypeptide useful in the present methods (e.g., in screening methods) is at least about 90%, 95%, 99%, or 100% identical to an amino acid sequence described herein (e.g., to a human sequence). In some embodiments, a nucleic acid encoding a molecular chaperone useful in the present methods (e.g., in screening methods) is at least about 90%, 95%, 99%, or 100% identical to a nucleic acid sequence described herein (e.g., to a human sequence).

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

Hsp90 (Heat-Shock 90-kD Protein 1)

HSP90 is a molecular chaperone that plays a key role in the conformational maturation of a number of proteins, including oncogenic signaling proteins. As described herein, Hsp90 accumulates in the mitochondria of cancer cells, but not normal cells, and can be targeted using the compositions described herein including a mitochondrial-penetrating sequence.

GenBank Acc. Nos. for human Hsp90 include NM_001017963.2 (nucleic acid) and NP_001017963.2 (protin), for heat shock protein 90 kDa alpha (cytosolic), class A member 1 isoform 1, and NM_005348.3 (nucleic acid) NP_005339.3 (protein), for heat shock protein 90 kDa alpha (cytosolic), class A member 1 isoform 2. Variant 2 differs in the 5' UTR and coding sequence compared to variant 1. The resulting isoform 2 is shorter at the N-terminus compared to isoform 1.

Hsp90 is also known as HSPCA; HSPC1; HSP90A; HSP89-ALPHA (HSP89A); Lipopolysaccharide-Associated Protein 2 (LAP2); and LPS-associated protein 2.

TRAP-1 (TNF Receptor-Associated Protein 1)

TRAP-1 has high homology to hsp90, and binds the type 1 tumor necrosis factor receptor (see Song et al., J. Biol. Chem., 270:3574-3581 (1995)). The deduced 661-amino acid protein is 60% similar to HSP90 family members, although it lacks the highly charged domain found in HSP90 proteins. See, e.g., Felts et al., J Biol Chem. 2000; 275(5): 3305-12. As described herein, TRAP-1 accumulates in the mitochondria of cancer cells, but not normal cells, and can be targeted using the compositions described herein including a mitochondrial-penetrating sequence.

GenBank Acc. Nos. for human TRAP-1 include NM_016292.2 (nucleic acid) and NP_057376.2 (amino acid). TRAP-1 is also referred to as Heat-Shock Protein, 75-KD (HSP75); Tumor Necrosis Factor Receptor-Associated Protein 1; TRAP1; and TNFR-Associated Protein 1.

Hsp60 (Heat-Shock 60-kD Protein 1)

Hsp60, together with its associated chaperonin, Hsp10, has been recognized as an evolutionary conserved stress response chaperone (Zhao et al., Embo J 2002; 21:4411-9), largely, but not exclusively compartmentalized in mitochondria (Soltys and Gupta, Int Rev Cytol 2000; 194:133-96), and with critical roles in organelle biogenesis and folding/refolding of imported preproteins (Deocaris et al., Cell Stress Chaperones 2006; 11:116-28). However, whether Hsp60 also contributes to cell survival is controversial, with data suggesting a pro-apoptotic function via enhanced caspase activation (Samali et al., Embo J 1999; 18:2040-8; Xanthoudakis et al., Embo J 1999; 18:2049-56), or, conversely, an anti-apoptotic mechanism involving sequestration of Bax-containing complexes (Shan et al., J Mol Cell Cardiol 2003; 35:1135-43). A role of Hsp60 in cancer was equally uncertain, as up- (Thomas et al., Leuk Res 2005; 29:1049-58; Cappello et al., BMC Cancer 2005; 5:139), or down-regulation (Tang et al., Cell Stress Chaperones 2005; 10:46-58; Cappello et al., Cancer 2006; 107:2417-24) of this chaperone has been reported in various tumor series correlating with disease outcome. As described herein, Hsp60 is highly expressed in tumor cells, as compared to normal cells, and targeting of Hsp60 causes mitochondrial dysfunction and apoptosis, whereas loss of Hsp60 in normal cells is well tolerated, and does not result in cell death.

Hsp60 is also known as CPN60; GROEL; HSP60; HSP65; SPG13; and HuCHA60. Exemplary GenBank Acc. Nos. for human Hsp60 include NM_002156.4 (nucleic acid) and NP_002147.2 (protein) for transcript variant 1 (the longer variant), and NM_199440.1 (nucleic acid) and NP_955472.1 (protein) for transcript variant 2. Variant 2 differs in the 5' UTR compared to variant 1. Both variants 1 and 2 encode the same isoform.

HspA9 (Heat Shock 70 kDa Protein 9

HspA9 belongs to the heat shock protein 70 family, which contains both heat-inducible and constitutively expressed members. The latter are called heat-shock cognate proteins, of which HspA9 is one. HspA9 plays a role in the control of cell proliferation, and may also act as a chaperone. See, e.g., Wadhwa et al., Int J Cancer. 2006; 118(12):2973-80; Wadhwa et al., J Gene Med. 2004; 6(4):439-44.

HspA9 is also known as mortalin, mthsp70, and GRP75. Exemplary GenBank Acc. Nos. for human HspA9 include NM_004134.5 (nucleic acid) and NP_004125.3 (protein), the heat shock 70 kDa protein 9 precursor.

II. Inhibitors of Molecular Chaperones

The compositions and methods described herein include the use of inhibitors of molecular chaperones, e.g., inhibitors or Hsp60, HspA9, Hsp90 and/or TRAP-1. The inhibitors useful in the methods and compositions described herein act directly on the chaperone protein itself, i.e., they do not act upstream or downstream. A number of such inhibitors are known in the art, e.g., peptide inhibitors and small molecule inhibitors. In some embodiments, the molecular chaperone inhibitors useful in this invention inhibit the ATPase activity of the chaperone, e.g., of Hsp60, HspA9, Hsp90, and/or TRAP-1. In some embodiments, the molecular chaperone inhibitors useful in this invention inhibit the binding of Hsp60, HspA9, Hsp90, or TRAP-1 to Cyclophilin D. In some embodiments, the molecular chaperone inhibitors useful in this invention inhibit the binding of Hsp60, HspA9, Hsp90, or TRAP-1 to survivin. In some embodiments, molecular chaperone inhibitors bind to a chaperone, and induce the proteasomal degradation of the chaperone's client proteins.

In addition, there are numerous methods useful for identifying, designing, and assaying candidate chaperone inhibitors. For example, rational screening methods have been used to identify additional molecules that target Hsp90, using a computational approach using a shepherdin peptide (LFACGSSHK, all D-amino acids, as a scaffold to screen a database of nonpeptidic structures. See, e.g., Meli et al., J. Med. Chem., 49:7721-7730 (2006).

Peptide Inhibitors of Molecular Chaperones

A number of peptide inhibitors of molecular chaperones, e.g., of Hsp90 and/or TRAP-1, are known in the art. The inhibitors useful in the compositions and methods described herein can include the entire peptide or polypeptide (e.g., all of an apoptosis-inducing protein (AIP such as survivin), or an active (i.e., inhibitory) fragment thereof that retains the Hsp90 inhibitory activity of the parent, i.e., at least 40% of the activity of the parent; an active fragment preferably has at least 50%, 60%, 70%, 80%, 90%, 100% or more of the Hsp90-inhibitory activity of the parent polypeptide.

Survivin Peptides and Derivatives

Survivin peptides and peptide derivatives are disclosed in U.S. patent application Ser. No. 11/187,230 (herein incorporated by reference in its entirety). Active survivin peptides share a core Hsp90 binding sequence motif of SEQ ID NO:2 (His Ser Ser Gly Cys), which is located in the single Baculovirus Inhibitor of Apoptosis (IAP) Repeat (BIR) domain of the Survivin protein. This motif corresponds to amino acid residues at position 80-84 of full-length Survivin (SEQ ID NO:1). Peptides including this motif, and peptide derivatives thereof, can (a) bind to the N-terminal ATPase domain of Hsp90 (the "ATP pocket") and (b) inhibit Hsp90-Survivin protein-protein interactions in vitro and in vivo.

The terms Survivin peptide and Survivin peptide derivative, as used herein, refer to peptides that include less than the complete amino acid sequence of a functional Survivin protein that prevents cell death. Survivin peptides and peptide derivatives useful to this invention inhibit molecular chaperones and in particular, inhibit interaction between a molecular chaperone, e.g., Hsp90 or TRAP-1, and Cyclophilin D.

The full-length human, wild type Survivin polypeptide has the following amino acid sequence:

(SEQ ID NO: 1)
MGAPTLPPAWQPFLKDHRISTFKNWPFLEGCACTPERMAEAGFIHCPTE

NEPDLAQCFFCFKELEGWEPDDDPIEEHKKHSSGCAFLSVKKQFEELTL

GEFLKLDRERAKNKIAKETNNKKKEFEETAKKVRRAIEQLAAMD

The following table (Table 1) lists some exemplary Survivin peptides that can bind to Hsp90:

TABLE 1

Exemplary Survivin peptides

| | |
|---|---|
| SEQ ID NO: 2 | His Ser Ser Gly Cys |
| SEQ ID NO: 3 | Lys His Ser Ser Gly Cys Ala Phe Leu Ser Val Lys |
| SEQ ID NO: 4 | Ile Asp Asp His Lys Lys His Ser Ser Gly Cys Ala Phe Leu |

TABLE 1 -continued

Exemplary Survivin peptides

| SEQ ID NO: 5 | Lys Lys His Ser Ser Gly Cys Ala Phe Leu |
| --- | --- |
| SEQ ID NO: 6 | Lys His Ser Ser Gly Cys |
| SEQ ID NO: 7 | His Ser Ser Gly Cys Ala |
| SEQ ID NO: 8 | Lys His Ser Ser Gly Cys Ala |
| SEQ ID NO: 9 | Lys Lys His Ser Ser Gly Cys |
| SEQ ID NO: 10 | His Ser Ser Gly Cys Ala Phe |
| SEQ ID NO: 11 | His Lys Lys His Ser Ser Gly Cys Ala Phe Leu Ser Val Lys Lys |
| SEQ ID NO: 12 | Lys His Ser Ser Gly Cys Ala Phe Leu |

Variants of Survivin peptides can also be used in the methods and compositions described herein. Conservative and non-conservative amino acid substitutions may be made. In particular, conservative amino acid substitutions can be made for one or more, e.g., up to five, ten, twenty, or thirty, amino acids outside of the core pentamer sequence corresponding to His 80 to Cys 84 in SEQ ID NO:1 (i.e., SEQ ID NO:2 set forth above). Peptidomimetics of Survivin peptides are described by Plescia et al. (Rational design of Shepherdin, a novel anticancer agent. Cancer Cell. 7(5):457-68 (2005)) herein incorporated by reference in its entirety.

Other IAP Peptides and Derivatives

Other Inhibitors of Apoptosis Proteins (IAPB) interact with Hsp90, including cIAP1 (Entrez Accession No.: NP_001156), cIAP2 (Entrez Accession No.: NP_001157), and XIAP (Entrez Accession No.: NP_001158). See, e.g., Deveraux and Reed, Genes and Dev., 13:239-252 (1999). These IAP proteins contain at least one Baculovirus IAP repeat domain that mediates Hsp90 interactions, as disclosed herein. For example, the first BIR domain of XIAP (BIR1) mediates Hsp90-XIAP binding interactions.

IAP proteins, or Hsp90-binding and -inhibiting fragments thereof, can therefore be used in the present compositions and methods. For example, peptides corresponding to one or more BIR domains in these IAP proteins, or Hsp90-binding fragments thereof, can be used in the compositions and methods disclosed herein to induce cancer or tumor cell death. IAP proteins, or Hsp90-binding fragments thereof, can also be screened as test compounds, e.g., to identify candidate compounds that inhibit binding between molecular chaperones and Cyclophilin D. In some embodiments, IAP proteins, or Hsp90-binding fragments thereof, can be screened as test compounds to identify candidate compounds that induce cancer cell death.

An exemplary first BIR domain of XIAP includes the sequence:

```
                                       (SEQ ID NO: 14)
RLKTFANFPSGSPVSASTLARAGFLYTGEGDTVRCFSCHAAVDRWQYGD

SAVGRHRKVSPNCRFIN
```

An exemplary first BIR domain of cIAP1 includes the sequence:

```
                                       (SEQ ID NO: 15)
RMSTYSTFPAGVPVSERSLARAGFYYTGVNDKVKCFCCGLMLDNWKRGD

SPTEKHKKLYPSCRFVQ
```

An exemplary first BIR domain of cIAP2 includes the sequence:

```
                                       (SEQ ID NO: 16)
RMSTYSTFPAGVPVSERSLARAGFYYTGVNDKVKCFCCGLMLDNWKLGD

SPIQKHKQLYPSCSFIQ
```

Variants of Peptide Inhibitors

Variants of peptide inhibitors of molecular chaperones are also part of this invention. These include sequence variants. Where a conservative amino acid substitution is made, the substitution can be of one amino acid residue for another in any of the following groups: arginine, histidine, and lysine; aspartic acid and glutamic acid; alanine, leucine, isoleucine and valine; and phenylalanine, tryptophan and tyrosine. The amino acid residues listed here are naturally occurring. Non-naturally occurring amino acid residues of like kind may also be substituted. For example, a negatively charged non-naturally occurring amino acid residue may be substituted for a negatively charged naturally occurring amino acid residue; a hydrophobic aromatic non-naturally occurring amino acid residue may be substituted for a hydrophobic aromatic naturally occurring amino acid residue; and so forth.

The degree of identity can vary and can be determined by methods well established in the art. "Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. A biologically active variant of a polypeptide described herein can have at least or about 80%, 85%, 90%, 95%, 96%, 97%, 98%, or 99% identity or homology to a corresponding naturally occurring polypeptide (e.g., a survivin fragment or a TAP fragment, e.g., as described herein). The nucleic acids encoding the biologically active variant polypeptides can be similarly described as having at least or about 80%, 85%, 90%, 95%, 96%, 97%, 98%, or 99% identity to a corresponding naturally occurring nucleic acid sequence. Those of ordinary skill in the art will readily recognize degenerate variants of nucleic acid sequences, and such variants can be used for the purposes described herein.

When using a peptide inhibitor and/or mitochondrial penetrating moiety in a human subject, it will generally be desirable to use a human or humanized sequence. Thus, the methods described herein can include using standard molecular biology techniques to humanize a non-human sequence. Alternatively, human sequences can be used to make the construct.

Modifications of Peptide Inhibitors

Modified versions of the peptides described herein can also be used in the compositions and methods described herein. The peptides and biologically active variants thereof can be modified in numerous ways. For example, agents, including additional amino acid residues, other substituents, and protecting groups can be added to either the amino terminus, the carboxy terminus, or both. The modification can be made for the purpose of altering the peptides' form or altering the way the peptides bind to or interact with one another, with non-identical peptides, or with other polypeptides. For example, the peptides can be modified to include cysteine residues or other sulphur-containing residues or agents that can participate in disulphide bond formation. For example, one can add at least two cysteine residues, one or both of which are, optionally, at the C-terminal or N-terminal of the peptide.

The peptides can be cyclized by formation of a disulfide bond between cysteine residues (or, more generally, between two of the at least two cysteine residues present in the polypeptide (e.g., at the terminal regions)). While the peptides of the present invention may be linear or cyclic, cyclic peptides generally have an advantage over linear peptides in that their cyclic structure is more rigid and hence their biological activity may be higher than that of the corresponding linear peptide (see, generally, Camarero and Muir, J. Am. Chem. Soc., 121:5597-5598, (1999)).

Strategies for the preparation of circular polypeptides from linear precursors have been described and can be employed with the present peptides. For example, a chemical cross-linking approach can be used to prepare a backbone cyclized version of the peptide (Goldenburg and Creighton, J. Mol. Biol., 165:407-413, (1983)). Other approaches include chemical intramolecular ligation methods (see, e.g., Camarero et al., Angew Chem. Int. Ed., 37:347-349, (1998); Tam and Lu, Prot. Sci., 7:1583-1592, (1998); Camarero and Muir, Chem. Commun., 1369-1370, (1997); and Zhang and Tam, J. Am. Chem. Soc., 119:2363-2370, (1997) and enzymatic intramolecular ligation methods (Jackson et al., J. Am. Chem. Soc., 117:819-820, (1995), which allow linear synthetic peptides to be efficiently cyclized under aqueous conditions. See also U.S. Pat. No. 7,105,341.

Alternatively, or in addition, the peptide can further include a substituent at the amino-terminus or carboxy-terminus. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can include a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to aromatic monocyclic or multicyclic groups containing from 6 to 19 carbon atoms. Examples of aryl groups include, but are not limited to unsubstituted or substituted phenyl, unsubstituted or substituted fluorenyl, and unsubstituted or substituted naphthyl.

As used herein, "heterocycloalkyl" refers to a monocyclic or multicyclic, saturated or unsaturated ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In certain embodiments, one of the atoms of the ring can be replaced with a carbonyl or sulfonyl group.

As used herein, "alkylene," "alkenylene," "alkynylene," "cycloalkylene," "arylene," "heteroarylene," and "heterocycloalkylene" refer to divalent linking "alkyl," "alkenyl," "alkynyl," "cycloalkyl," "aryl," "heteroaryl," and "heterocycloalkyl" groups. The divalent linkers, in some embodiments, can be present in both directions, e.g., a C(O)NH can either be —C(O)NH— or —NHC(O)—.

As noted, the peptides can vary in length and can be or can include contiguous amino acid residues that naturally occur in chaperone binding proteins (CBP), e.g., Survivin or IAPB, or that vary to a certain degree from naturally occurring CBP sequences (but retain sufficient activity to be useful). Where the peptides include, at their N-terminus or C-terminus (or both), amino acid residues that are not naturally found in CBPs, the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 150, 160, 170, 180, 190, or 200 residues, and one terminus can include none (e.g., it can terminate in an amino acid sequence identical to a naturally occurring Survivin sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues.

The peptides, including the modified peptides described above, can be protease resistant and can include one or more types of protecting groups such as an acyl group, an amide group, a benzyl or benzoyl group, or a polyethylene glycol. More specifically, a peptide, including the modified peptides described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Peptides having non-naturally occurring amino acid residues may be referred to as synthetic peptides and constitute one type of variant as described herein. Other variants include peptides in which a naturally occurring side chain of an amino acid residue (in either the L- or D-form) is replaced with a non-naturally occurring side chain.

In one embodiment, the peptides can have three extra amino acids (Met-Gly-Ser) at either terminus (or both) (e.g., at the N-terminus) and seven to eight extra amino acids (Thr-Ser-His-His-His-His-His-His-Cys (SEQ ID NO:13)) at either terminus (or both) (e.g., at the C-terminus).

In another embodiment, the peptides can be PEGylated by methods known in the art.

For guidance on peptide modification by reduction/alkylation and/or acylation, one can consult Tarr, *Methods of Protein Microcharacterization*, J. E. Silver ed., Humana Press, Clifton N.J. (1986) 155-194; for guidance on chemical coupling to an appropriate carrier, one can consult Mishell and Shiigi, eds, *Selected Methods in Cellular Immunology*, WH Freeman, San Francisco, Calif. (1980) and U.S. Pat. No. 4,939,239; and for guidance on mild formalin treatment, one can consult Marsh, Int. Arch. Allergy Appl. Immunol., (1971) 41:199-215.

Peptidomimetics of the inhibitory peptides can also be used. Peptide inhibitors disclosed herein and known in the art can be modified according to methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., J. Biol. Chem., 278:45746, (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as ∀-amino phosphonic acids and ∀-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. Exemplary Survivin retro-inverso peptidomimetics include LFACGSSHK (SEQ ID NO:25), CGSSH (SEQ ID NO:26), GSSHK (SEQ ID NO:27), KKWKMRRNQF-WVKVQRLFACGSSHK (SEQ ID NO:28), KKWKMR-RNQFWVKVQRCGSSH (SEQ ID NO:29), and KKWKM-RRNQFWVKVQRGSSHK (SEQ ID NO:30), wherein the sequences include all D-amino acids. These sequences can be modified, e.g., by biotinylation of the amino terminus and amidation of the carboxy terminus.

Any of the peptides described herein, including the variant forms described herein, can further include a heterologous polypeptide (e.g., a polypeptide having a sequence that does not appear in a CBP). The heterologous polypeptide can be a polypeptide that increases the circulating half-life of the peptide to which it is attached (e.g., fused, as in a fusion protein). The heterologous polypeptide can be an albumin (e.g., a human serum albumin or a portion thereof) or a portion of an immunoglobulin (e.g., the Fc region of an IgG). The heterologous polypeptide can be a mitochondrial-penetrating moiety.

Compounds mimicking the necessary conformation of the peptides described herein are contemplated as within the scope of this invention. A variety of designs for such mimetics are possible. U.S. Pat. No. 5,192,746; U.S. Pat. No. 5,169,862; U.S. Pat. No. 5,539,085; U.S. Pat. No. 5,576,423; U.S. Pat. No. 5,051,448; and U.S. Pat. No. 5,559,103, all hereby incorporated by reference, describe multiple methods for creating such compounds.

Non-peptidic compounds that mimic peptide sequences are known in the art (Meli et al. J. Med. Chem., 49:7721-7730 (2006), describing methods of identifying nonpeptide small molecule mimics of shepherdin). Synthesis of non-peptide compounds that mimic peptide sequences is also known in the art (see, e.g., Eldred et al. J. Med. Chem., 37:3882, (1994); Ku et al. J. Med. Chem., 38:9, (1995); Meli et al. J. Med. Chem., 49:7721-7730 (2006)). Such nonpeptide compounds that mimic CBP peptides that bind chaperones are specifically contemplated by the present invention.

The present invention also contemplates synthetic mimicking compounds. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the herein-described chaperone inhibitor peptides. These mimetics include, but are not limited to, peptides in which L-amino acids are replaced by their D-isomers. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, Proc. Natl. Acad. Sci. (USA), 85:2444-2448, (1988); Lipman and Pearson, Science, 227:1435-1441, (1985). More generally, the CBP peptides described herein and the mimetics described above can be synthesized using any known methods, including tea-bag methodology or solid phase peptide synthesis procedures described by Merrifield et al., Biochemistry, 21:5020-5031, (1982); Houghten Wellings, Proc. Natl. Acad. Sci. (USA), 82:5131-5135, (1985); Atherton, Methods in Enzymology, 289:44-66, (1997), or Guy and Fields, Methods in Enzymology, 289:67-83, (1997), or using a commercially available automated synthesizer.

Small Molecule Inhibitors of Molecular Chaperones

A number of small molecule chaperone inhibitors useful in the methods and compositions described herein are known in the art. For example, small molecule chaperone inhibitors that are useful in the compositions and methods described herein include, but are not limited to, molecules that bind to a Hsp90 ATP binding pocket. Small molecule Hsp90 inhibitors known in the art are described, for example, in Rodina et al., (Nature Chemical Biology, published online Jul. 1, 2007).

In some embodiments, the chaperone inhibitor is an Hsp90 inhibitor selected from one of several chemotypes. Two of these chemotypes are ansamycin and macrolactone inhibitors. These are represented by radicicol and cycloparadicicol, members of the macrolactone Hsp90 inhibitor class, and 17-dimethylaminoethylamino-17-demethoxygeldanamycin (17DMAG) and 17AAG, members of the ansamycin class of Hsp90 inhibitors. The structural basis for inhibition of Hsp90 by radicicol and geldanamycin is known, so one of skill in the art could readily generate and test analogs thereof that would retain Hsp90 inhibitory activity, see, e.g., Roe et al., J. Med. Chem. 42(2):260-6 (1999). Purine inhibitors form a third class of compounds useful in the compositions and methods described herein.

Ansamycin Inhibitors of Hsp90

Further examples of molecular chaperone inhibitors that are useful in this invention include, but are not limited to, quinine ansamycin antibiotics, such as the macbecins, geldanamycin, geldanamycin analogues, and herbimycin A.

Geldanamycin is an inhibitor of heat shock protein-90 (Hsp90), which is involved in the folding, activation and assembly of a wide range of proteins ("client proteins"), including key proteins involved in signal transduction, cell cycle control and transcriptional regulation. The binding of geldanamycin to Hsp90 disrupts Hsp90-client protein interactions, preventing the client proteins from folding correctly. Geldanamycin and geldanamycin analogues are part of this.

As used herein, "geldanamycin analogues" refers to compounds that share a common core structure with geldanamycin but have minor chemical modifications.

Geldanamycin analogues that are variant at position 17 of geldanamycin are known in the art and many are commercially available. Examples of commercially available geldanamycin analogues include, but are not limited to, 17-allylamino-demethoxygeldamycin (17-AAG), 17-dimethylaminogeldanamycin, 17-GMB-APA-GA (a maleimido derivative of geldanamycin that enables the conjugation of GA to a polypeptide), 17-(Dimethylaminoethylamino)-17-demethoxygeldanamycin (17-DMAG), 17-[2-(Pyrrolidin-1-yl)ethyl]aminno-17-demethoxygeldanamycin (17-AEP-GA), and 17-(Dimethylaminopropylamino)-17-demethoxygeldanamycin (17-DMAP-GA). See also Sasaki et al., U.S. Pat. No. 4,261,989 (1981); Schnur et al., U.S. Pat. No. 5,932,566 (1999); Schnur et al., J. Med. Chem., 38:3806-3812, (1995); Schnur et al., J. Med. Chem., 38:3813-3820, (1995); and Santi et al., US 2003/0114450 A1 (2003).

Geldanamycin analogues that are variant at position 11 are known in the art. Examples include, but are not limited to, Muroi et al., U.S. Pat. No. 4,421,688 (1983); Schnur, U.S. Pat. No. 5,387,584 (1995); Schnur et al., U.S. Pat. No. 5,932,566 (1999); Welch et al., U.S. Pat. No. 6,015,659 (2000); Whitesell et al., WO 94/08578 A2 (1994); Ho et al., WO 00/03737 A2 (2000); Snader et al., WO 02/36574 A1 (2002); Snader et al., WO 02/079167 A1 (2002); Santi et al., WO 03/013430 A2 (2003); Zhang et al., WO 03/066005 A2 (2003); Omura et al., JP 63-218620 (1988); Schnur et al., J. Med. Chem., 38:3806-3812, (1995); and Schnur et al., J. Med. Chem., 38:3813-3820, (1995); which are herein incorporated by reference. 11-O-methylgeldanamycin compounds known in the art are described in U.S. Pat. No. 6,855,705, U.S. Pat. No. 6,887,993, and U.S. Pat. No. 6,870,049.

In some embodiments of the composition, the molecular chaperone inhibitor includes geldanamycin analogues:

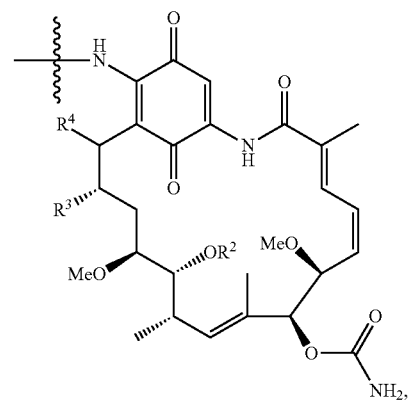

where, $R^2$ is H, alkyl, aryl, or arylalkyl; $R^3$ is H, alkyl; and $R^4$ is H, alkyl, alkenyl, aryl, arylalkyl, $OR^d$, wherein $R^d$ is H, alkyl, or arylalkyl.

In some embodiments of the composition, $R^2$ is H or alkyl; $R^3$ is H, alkyl; and $R^4$ is H, or $OR^d$, wherein $R^d$ is H, alkyl.

In some embodiments of the composition, $R^2$ is H; $R^3$ is methyl; and $R^4$ is H.

Resorcinol-Derived Inhibitors of Hsp90

Compounds derived from Resorcinol are potent inhibitors of Hsp90. These include compounds based on the 4,5-diarylisoxazole scaffold (see, for example, Brough et al., J. Med. Chem, 2007), compounds based on the 3,4-diarylpyrazole scaffold (see, for example, U.S. Pat. No. 7,247,734 and Sharp et al., Cancer Res. 67 (5):2206-16 (2007)), and 3,4-diaryl pyrazole resorcinol HSP90 inhibitor (CCT018159), amide resorcinol compounds (as described, for example, in International Publication No. WO/2006/117669), and isoxazole resorcinol compounds. See also Sharp et al., Mol Cancer Ther. 6 (4):1198-1211 (2007) (synthetic, potent resorcinylic pyrazole/isoxazole amide analogues, e.g., VER-49009 and the corresponding isoxazole VER-50589); Eccles et al., Cancer Res. 68 (8):2850-60 (2008) (NVP-AUY922, a novel resorcinylic isoxazole amide heat shock protein 90 (HSP90) inhibitor); Barril et al., Bioorg. Med. Chem. Let. 16(9):2543-2548 (2006) (piperazinyl, morpholino and piperidyl derivatives of the pyrazole-based Hsp90 inhibitor CCT018159).

Macrolactone-Hsp90 Inhibitors

The macrocyclics radicicol and monocillin, and analogs thereof such as cycloproparadicicol, are inhibitors that bind the ATP-binding site of Hsp90. See, e.g., Turbyville et al., J. Nat. Prod., 69(2):178-184 (2006), Soga et al., Curr. Cancer Drug Targets. 3(5):359-69 (2003), Shiotsu et al., Blood. 96(6):2284-91 (2000), and U.S. Pat. No. 7,115,651. KF25706, a novel oxime derivative of radicicol, has in vivo antitumor activity via selective depletion of Hsp90 binding signaling molecules (Soga et al., Cancer Res. 59(12):2931-8 (1999)).

Chimeric inhibitors that include structural components of radicicol and geldanamycin are also known, see, e.g., Hadden et al., Curr. Top. Med. Chem. 6(11):1173-82; Shen et al., J. Org. Chem. 71(20):7618-31 (2006).

Purine Inhibitors of Hsp90

Hsp90 inhibitors of the purine-scaffold class have been reported to be potent and selective against Hsp90 both in vitro and in vivo models of cancer, and the structural basis of this activity has been determined. See Wright et al., Chem. Biol. 11(6):775-85 (2004). Several 8-Aryl-Sulfanyl Adenine compounds have been synthesized and shown to have Hsp90 inhibitory activity, e.g., PU-H71 and PU-H64, the structures of which have been solved with Hsp90. See Immormino et al., J. Med. Chem. 49(16):4953-60 (2006). Other purine class Hsp90 inhibitors are known in the art and include, for example, 3,4-diaryl pyrazoles and related analogs (McDonald et al., Curr. Top. Med. Chem. 6(11):1193-203 (2006)); pyrazolopyrimidines and related analogs (U.S. Pat. No. 7,148,228), pyrrolopyrimidines and related analogs (U.S. Pat. No. 7,138,402), and 2-aminopurine analogs (U.S. Pat. No. 7,138,401).

Hsp60 Inhibitors

Several Hsp60 inhibitors are known in the art, including epolactaene (Nagumo et al., Biochem. J. 387:835-840 (2005); Tan and Negishi, Org. Lett. 8(13):2783-2785 (2006); and Nagumo et al., Bioorganic & Medicinal Chemistry Letters 14:4425-4429 (2004)), and mizoribine (bredinin) (Itoh et al., J. Biol. Chem. 274:35147-35151 (1999)).

HspA9 (Mortalin) Inhibitors

MKT-077, a cationic rhodacyanine dye analogue with selective toxicity to cancer cells, binds to HspA9/mortalin, and abrogates its interactions with the tumor suppressor protein, p53. See, e.g., Wadhwa et al., Cancer Res. 2000; 60(24):6818-21.

Other Inhibitors

Molecular chaperone inhibitors that are useful in this invention also include molecules that inhibit interaction between Hsp60 and Cyclophilin D, Hsp90 and Cyclophilin D, or TRAP-1 and Cyclophilin D. These inhibitors may be identified from molecules known in the art, or present in chemical libraries by the methods described herein; see, e.g., Meli et al., J. Med. Chem. 49:7721-7730 (2006), and Howes et al., Anal. Biochem., 350(2):202-213 (2006). For example, the non-peptidic small molecule 5-aminoimidazole-4-carboxamide-1-beta-D-ribofuranoside (AICAR) was identified as a structurally novel inhibitor of Hsp90 (see Meli et al., 2006, supra), and can be used in the methods described herein. See also Blagg et al., Med. Res. Rev. 26(3):310-338 (2005).

III. Mitochondrial-Penetrating Moieties

Described herein are mitochondrial penetrating molecular chaperone inhibitors. Any of the molecular chaperone inhibitors described herein can be modified by association with mitochondrial-penetrating moieties using methods known in the art, with the proviso that if the chaperone inhibitor is Shepherdin or an active fragment thereof, the mitochondrial-penetrating moiety is not Antennapedia or a fragment thereof. Examples are given below.

As used herein, a mitochondrial-penetrating moiety is a chemical group, e.g., a peptide, peptidomimetic, or other compound, that increases mitochondrial localization of an associated, e.g., chemically conjugated, molecular chaperone inhibitor, as compared to the molecular chaperone inhibitor alone.

Peptide Mitochondrial-Penetrating Moieties

In the compositions described herein, a chaperone inhibitor (as described herein) can be attached to a peptide mitochondrial-penetrating moiety. For example, an Antennapedia carrier sequence, corresponding to a sequence found on the third α-helix of the Antennapedia (Gratton et al., Cancer Cell, 4:31, (2003)), can be used. An exemplary sequence of such a peptide is RQIKIWFQNRRMKWKK (SEQ ID NO:18), herein ANT. Other examples of targeting peptides to which the chaperone inhibitors disclosed herein can be attached include, but are not limited to, e.g., the TAT protein sequence from HIV-1 (Chen et al., Proc. Natl. Acad. Sci. USA, 96:4325, (1999); Kelemen et al., J. Biol. Chem., 277:8741-8748, (2002)), e.g., RKKRRQRRR (SEQ ID NO:19) (Brooks et al., Adv. Drug Del. Rev., 57(4):559-577 (2005)), or a modified TAT having the sequence RKKRRORRRGC (SEQ ID NO:20) (Barnett et al., Inv. Ophth. Vis. Sci., 47:2589-2595 (2006)). Yet other examples include VP22 protein from Herpes Simplex virus (Lundberg and Johansson, Biochem. Biophys. Res. Comm., 291:367-371, (2002)), and the Pep-1 peptide carrier (Morris et al., Nature Biotech., 19:1173-1176, (2001)). In some embodiments, the peptides comprise D-isomer amino acids or other modifications, e.g., to improve uptake or reduce cellular degradation.

Polypeptides that include peptide mitochondrial-penetrating moieties can be produced by standard techniques, such as chemical synthesis, or expressed from a nucleic acid that encodes the polypeptide.

Other fragments that may be useful as mitochondrial-penetrating moieties include, but are not limited to, mitochondrial-targeting sequences that are found in proteins that localize to mitochondria. Non-limiting examples of mitochondrial-targeting sequences include the N-terminal region of human cytochrome c oxidase subunit VIII, the N-terminal region of the P1 isoform of subunit c of human ATP synthase, or the N-terminal region of the aldehyde dehydrogenase targeting sequence as described in U.S. Pat. App. 20040072774, herein incorporated by reference. For example, fragments of mitofusins (human mitofusin 1 sequence is at GenBank Acc. No. NP_284941.2; human mitofusin 2 sequence is at GenBank Acc. No. NP_055689.1), e.g., amino acids 97-757 of human mitofusin 2 (see U.S. Pat. No. 6,953,680, herein incorporated by reference), are useful as mitochondrial-targeting moieties in this invention.

Peptidomimetic Mitochondrial-Penetrating Moieties

Peptidomimetic mitochondrial penetrating moieties can also be used in the compositions and methods disclosed herein. A general description of peptidomimetics, and methods for making them, can be found above.

For example, non-hydrolyzeable tetraguanidinium compounds as described in Fernandez-Carneado et al. J. Am. Chem. Soc. 127(3):869-74, (2005), incorporated herein, can be used in the present compositions and methods.

Mitochondrial Targeting Signal Peptides

Fragments of that direct proteins to the mitochondria can also be used. Examples include RRIVVLHGYGAVKEV-LLNHK (SEQ ID NO:41), amino acids 74-95 of Rat Cytochrome P450 2E1 (CYP2E1) (Neve and Ingelman-Sundberg, J. Biol. Chem., 276(14):11317-11322 (2001); the cleavable prepiece from the yeast cytochrome c oxidase IV precursor (MLSLRQDIRFFKPATRTLCSSR (SEQ ID NO:42), see Maarse et al., EMBO J. 3(12):2831-2837 (1984) and Hurt et al., FEBS 178(2) 306-310 (1984)); mitochondrial-targeting signal from the PB2 protein of influenza viruses (Carr et al., Virology, 344(2):492-508, (2006); import signal contained within heme lyases (Diekert et al., Proc. Natl. Acad. Sci. U.S.A 96(21):11752-11757, (1999); the leader peptide of the mitochondrial matrix enzyme ornithine transcarbamylase (OTC) (Horwich et al., EMBO J. 4(5):1129-1135, (1985). Hay et al., Biochim. Biophys. Acta. 779(1):65-87, (1984); Fujiwara et al., Genome Inform. Ser. Workshop, Genome Inform. 8:53-60, (1997).

Nucleic Acid Mitochondrial-Penetrating Moieties

Nucleic acids that act as mitochondrial penetrating moieties (such as those described in U.S. Pat. No. 5,569,754, herein incorporated by reference, e.g., CCGC-CAAGAAGCG (SEQ ID NO:21); GCGTGCA-CACGCGCGTAGACTTCC CCCGCAAGTCACTCGT-TAGCCCGCCAAGAAGCGACCCCTCCGGGGCGAGCTG AGCGGCGTGGCGCGGGGGCGTCAT (SEQ ID NO:22); ACGTGCATACGCACGTAGACATTCCCCGCTTC-CCACTCCAAAGTCCGCCAAG AAGCGTATCCCGCT-GAGCGGCGTGGCGCGGGGGCGTCATCCGTCAGCTC (SEQ ID NO:23); or ACTTCCCCCGCAAGTCACTCGT-TAGCCCGCCAAGAAG CGACCCCTCCGGGGC-GAGCTG (SEQ ID NO:24) can also be used in the compositions and methods described herein. Methods for linking nucleic acids to peptides are known in the art.

Lipophilic Cation Mitochondrial-Penetrating Moieties

Lipophilic cations that act as mitochondrial penetrating moieties are described in Smith et al., Proc. Natl. Acad. Sci. U.S.A., 100(9):5407-12 (2003), which is herein incorporated by reference in its entirety. Lipophilic cations that are useful to this invention include, for example, Rhodamine 123 and phosphonium salts, e.g., methyltriphenylphosphonium and tetraphenylphosphonium.

In some embodiments, the cationic mitochondrial-penetrating moiety includes:

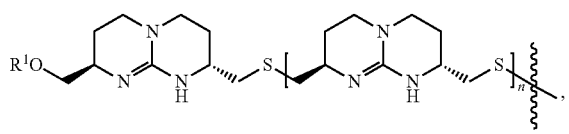

where $R^1$ is H, alkyl, alkenyl, alkynyl, haloalkyl, aryl, arylalkyl, or $R^a R^b R^c Si$; $R^a$, $R^b$, and $R^c$ are independently selected from alkyl or aryl; and n can be 0, 1, 2, 3, 4, 5, or 6.

In some embodiments, the cationic mitochondrial-penetrating moiety includes

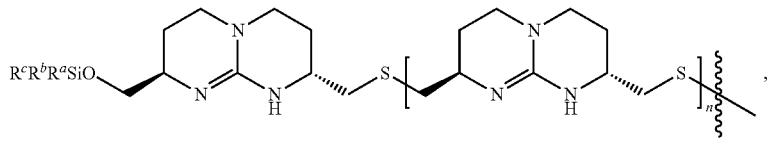

where, IV, $R^b$, and $R^c$ are independently selected from alkyl or aryl; and n can be 1, 2, or 3. In some embodiments, the cationic mitochondrial-penetrating moiety includes (aryl)$_3$ P—. In some embodiments, the cationic mitochondrial-penetrating moiety includes Rhodamine 123:

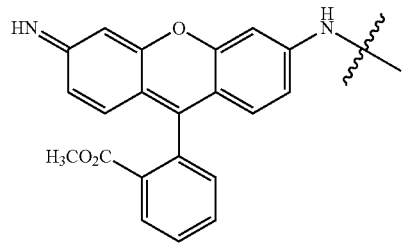

IV. Linking Moiety

In some embodiments, the mitochondrial penetrating moiety is linked to a molecular chaperone inhibitor as described herein via a linker. As used herein, to "link" means to associate a mitochondrial-penetrating moiety and a chaperone inhibitor via a covalent or non-covalent bond or association.

A number of linkers can be used to link the chaperone inhibitor, to the mitochondrial-penetrating moiety. For example, a peptide linker can be used, e.g., a peptide linker including one, two, three, four, five, six, seven, eight, or more amino acids. In some embodiments, the peptide linker is flexible, i.e., contains amino acids that adopt flexible conformations, e.g., comprising glycine, alanine, and/or glutamine residues.

In embodiments where the mitochondrial-penetrating moiety and the chaperone inhibitor are both peptides, it will generally be desirable to produce the mitochondrial-targeted chaperone inhibitor as a fusion protein, with or without an intervening linker, e.g., using a nucleic acid that encodes the entire fusion protein.

In some embodiments, the linker moiety is divalent and can be selected from the group consisting of alkylene, alkenylene, alkynylene, cycloalkylene, arylene, heteroarylene, and peptide linker, wherein any two adjacent carbon-carbon bonds of said alkylene, alkenylene, or alkynylene, can be optionally replaced with one or more of O, NH, S, PR$^e$, C(O)NR$^f$, arylene, heterocycloalkylene, or heteroarylene; wherein R$^e$ and R$^f$ are independently selected from alkyl or aryl.

In some embodiments, the linker moiety is:

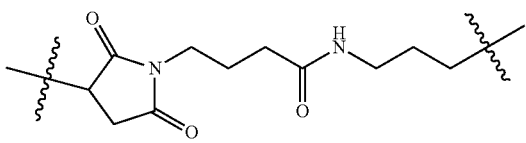

In some embodiments, the linker moiety is alkylene

In some embodiments, the linker moiety is alkylene with six carbon atoms.

One type of mitochondrial-targeted chaperone inhibitor is produced by crosslinking a chaperone inhibitor to a mitochondrial-penetrating moiety. Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

General methodology useful for making the compositions described herein are known in the art. In some embodiments, the methods can include contacting a mitochondrial-penetrating moiety, e.g., ANT as described herein, with a linker, e.g., a disulfide linker such as SSP, to form a reaction mixture, contacting the reaction mixture with a chaperone inhibitor, e.g., a geldanamycin analog, and obtaining a composition that includes a mitochondrial-penetrating moiety conjugated to the chaperone inhibitor. In some embodiments, the methods include contacting the mitochondrial-penetrating moiety with an amount of linker such that the ratio of linker to mitochondrial-penetrating moiety in the reaction mixture is about 1:1. Accordingly, the invention features methods of preparing a mitochondrial-penetrating moiety, e.g., ANT as described herein, conjugated to a chaperone inhibitor, e.g., a geldanamycin analog such as 17-AAG.

The mitochondrial-penetrating moiety and chaperone inhibitor can be joined, using recombinant methods known in the art, by a synthetic linker that enables them to be made as a single protein chain; see e.g., Bird et al., Science, 242:423-426 (1988); and Huston et al. Proc. Natl. Acad. Sci. USA, 85:5879-5883 (1988)).

For example, chaperone inhibitor of the invention can be functionally linked (by chemical coupling, genetic fusion, noncovalent association or otherwise) to one or more mitochondrial-penetrating moieties.

The compositions described herein include compounds of the formula:

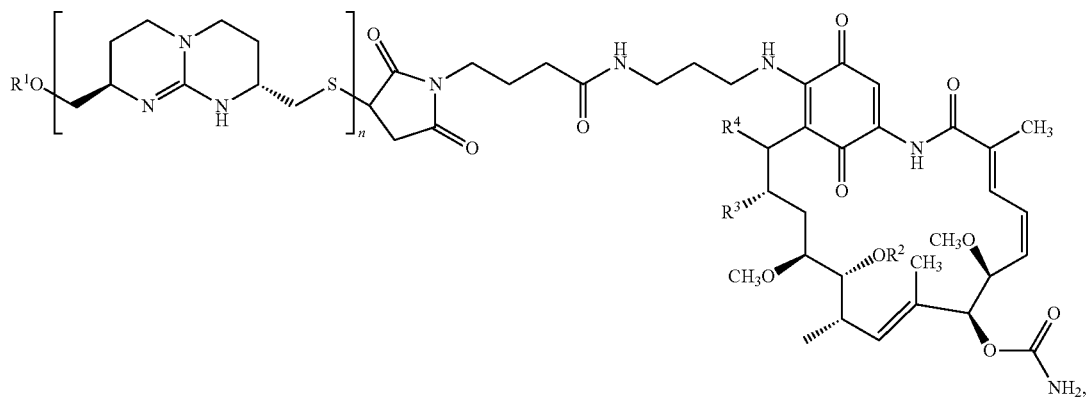

wherein, $R^1$ is H, alkyl, alkenyl, alkynyl, haloalkyl, aryl, arylalkyl, or $R^aR^bR^cSi$; $R^2$ is H, alkyl, aryl, or arylalkyl; $R^3$ is H, alkyl; $R^4$ is H, alkyl, alkenyl, aryl, arylalkyl, $OR^d$, wherein $R^d$ is H, alkyl, or arylalkyl; $R^a$, $R^b$, and $R^c$ are independently selected from alkyl or aryl; and n is an integer between 1 and 10, inclusive or a pharmaceutically acceptable salt thereof.

In some embodiments, the salt is a hexafluorophosphate salt

In some embodiments, $R^1$ is $R^aR^bR^cSi$, $R^a$, $R^b$, and $R^c$ are independently selected from alkyl or aryl; $R^2$ is H; $R^3$ is H, alkyl; $R^4$ is H; and n is 1, 2, 3, or 4.

In some embodiments, the compounds can be selected from:

35     36
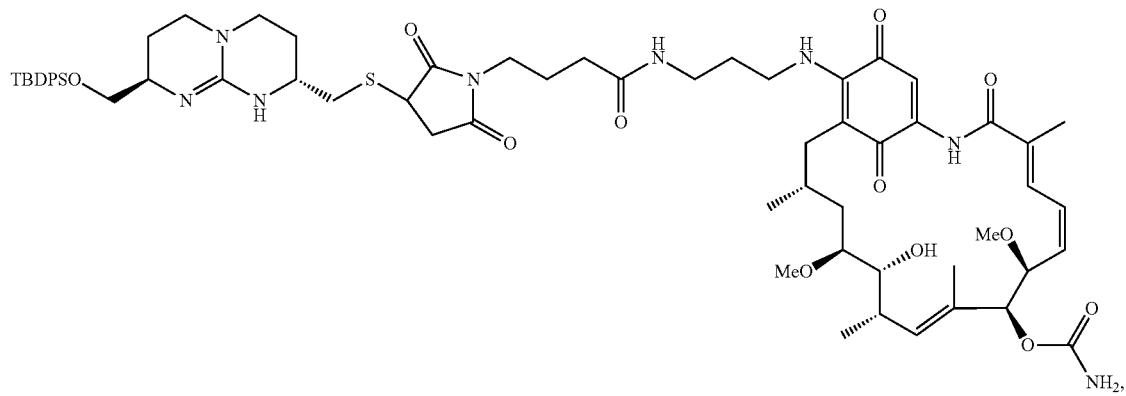
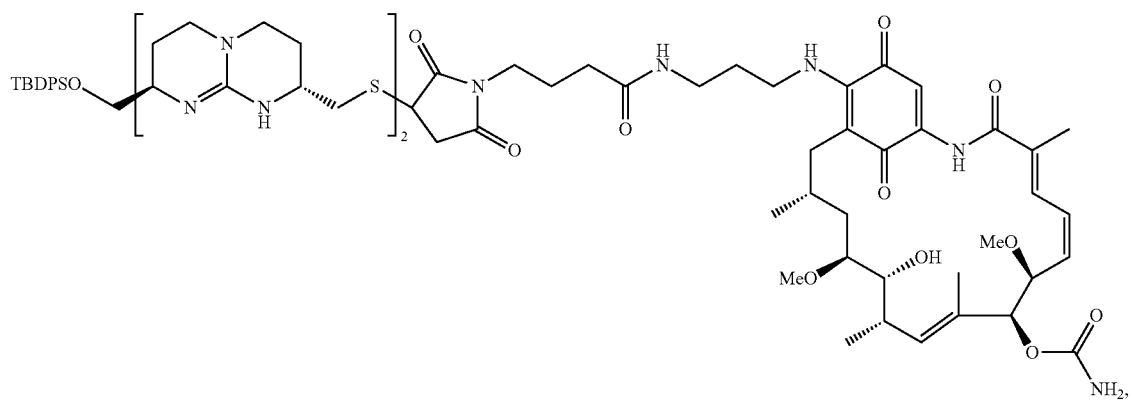
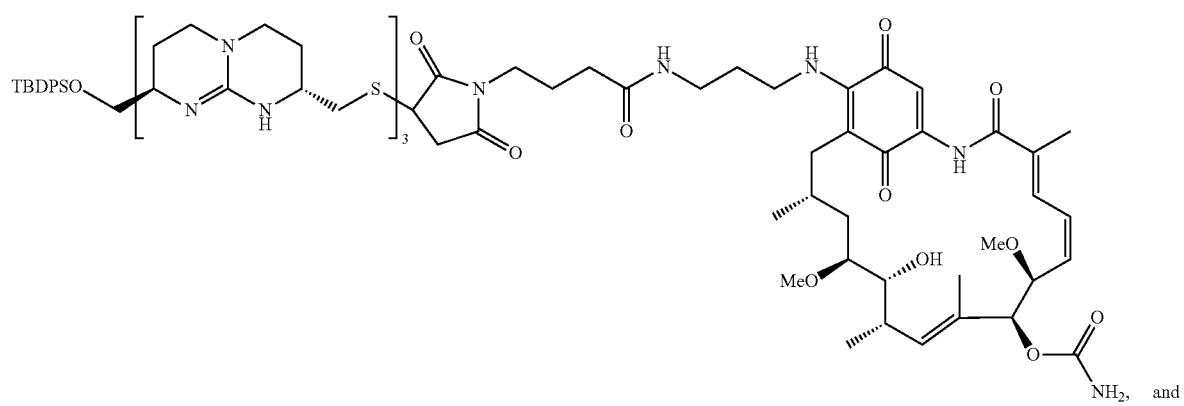, and
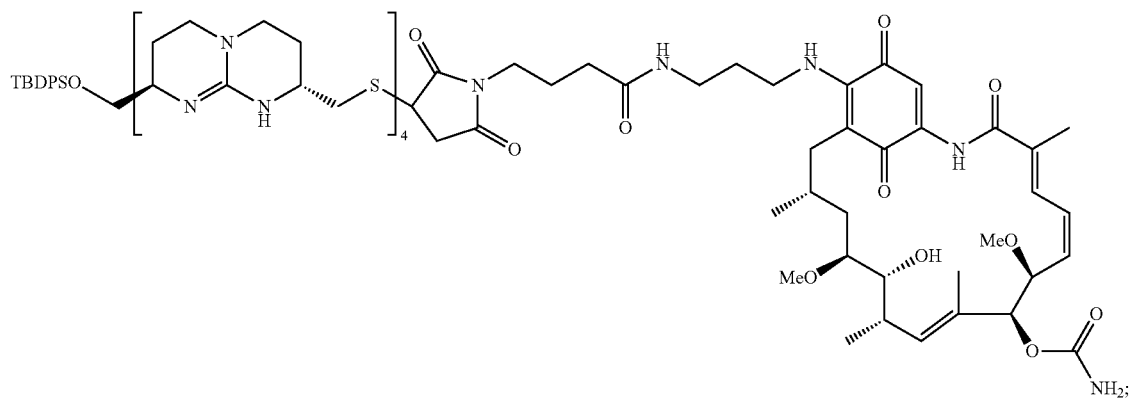;

or a pharmaceutically acceptable salt thereof.

In some embodiments, the compounds can be of the formula:

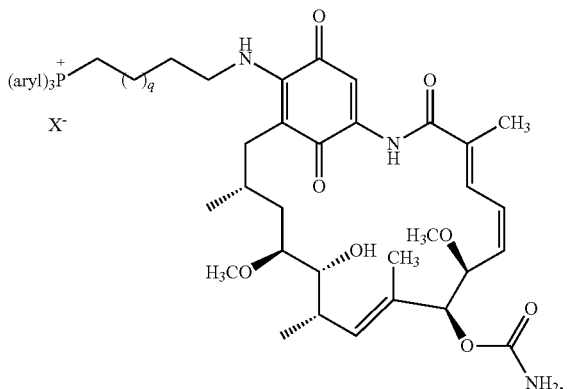

wherein, q is 1, 2, 3, 4, 5, or 6; and X is pharmaceutically acceptable counter-ion.

In some embodiments, q is 3.
In some embodiments, aryl is phenyl.
In some embodiments, aryl is phenyl and q is 3.
In some embodiments, X can be hexafluorophosphate.
In some embodiments, the compound can be:

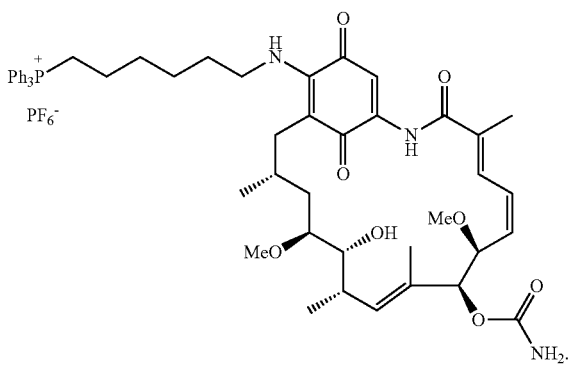

Methods of Synthesis

The compounds described herein can be prepared by the conjugation of geldanamycin or the 17-GMB-APA-GA analogue. The use of the either of these compounds allows for conjugation with nucleophilic moieties such as thiols, amines, or alcohols. The elaboration of the cationic mitochondrial-penetrating moiety can be performed to include between one and 10 of the guanidinio moieties containing the monomeric structure:

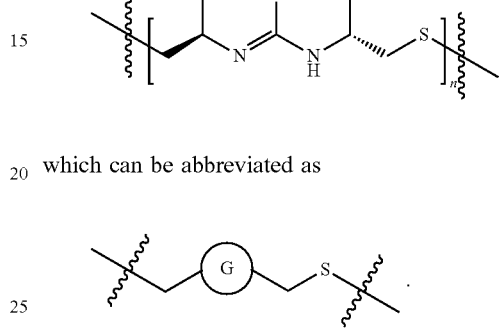

which can be abbreviated as

A general iterative method of synthesis of such compositions containing oligomeric guanidinio structures is shown below. The mesylate G1 can be treated with potassium acetate (KSAc) to provide the thio ester which upon base treatment followed by exposure to the maleimide derivative (L-GA) of a molecular chaperone inhibitor, such as geldanamycin (GA), can provide the desired first generation compositions G1-GA. The G1-thioester compound can in turn be treated in sequence such as with methanesulfonic acid; cesium carbonate in the presence of tributylphosphine; followed by reaction with G1 and finally treating with methanesulfonic anhydride provides G2 which is the higher homologue of G1. Such iterative process as can be seen clearly provides access to oligomeric guanidinio units. Few compounds are elaborated below in the Examples to demonstrate the process. Although the scheme shown here is described for the linkers with maleimide group for facilitating conjugation, this method can be extended to linkers with other functionalities for conjugation such as the N-hydroxy succinimide esters (such as 17-NETS-ALA-GA). One of skill in the art will also recognize that this iterative scheme can be extended to other non-GA based Hsp90 inhibitors such as the purine based antagonists or the resorcinol antagonists.

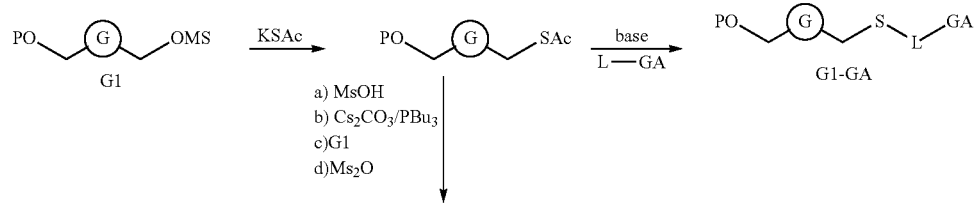

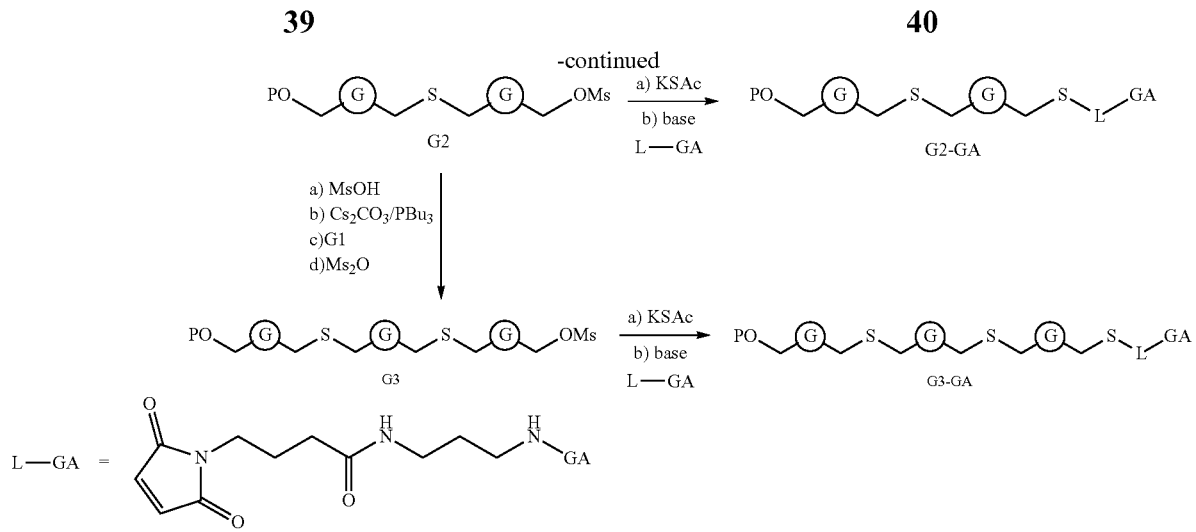

V. Methods of Treatment

The compounds described herein, i.e., mitochondrial-targeted chaperone inhibitors, are useful in the treatment of disorders associated with uncontrolled cellular proliferation, as occurs, for example, in tumor formation and in cancer. In some embodiments, tumors treated by a method described herein can be associated with a cancer described herein.

Generally, the methods include administering a therapeutically effective amount of a therapeutic compound as described herein, to a subject who is in need of, or who has been determined to be in need of, such treatment.

As used in this context, to "treat" means to ameliorate at least one symptom of the disorder associated with uncontrolled cellular proliferation. Ideally, a treatment can result in the death of the proliferating cells, or in a decrease in the rate of proliferation of the cells (i.e., the cancer or tumor cells).

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected.

The compositions can be administered systemically, locally, or both, using methods known in the art, e.g., parenteral, oral, mucosal, or other routes of administration. As one of skill in the art will appreciate, the route of administration should be selected based on suitability for the treatment of the specific condition, and the formulation of the composition.

The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The compounds described herein are useful in the treatment of tumors and cancer. The compounds described herein can be administered to a patient diagnosed with cancer, e.g., any of the types of cancers referred to herein. For example, the mitochondrial-targeted chaperone inhibitor disclosed herein can be used, without limitation, to treat a subject suffering from one or more of a cancer or tumor of the lung, breast, epithelium, large bowel, rectum, testicle, gallbladder, bile duct, biliary tract, prostate, colon, stomach, esophagus, pancreas, liver, uterus, ovary, or brain. In certain embodiments, the compounds described herein are useful in the treatment of chronic myelogenoeous leukemia, B lymphoblastoid leukemia, breast adenocarcinoma, lung adenocarcinoma, prostate adenocarcinoma, gliobastoma, colon adenocarcinoma, and cervical carcinoma. In other examples, the mitochondrial-targeted chaperone inhibitor disclosed herein can be used to treat, without limitation, a subject suffering from haemangioma, Hodgkin's disease, large cell non-Hodgkin's lymphoma, malignant lymphoma, leukemia, polycythemia vera, neuroblastoma, retinoblastoma, myelodysplastic syndrome with refractory anemia, neuroblastoma, glioma, pheochromocytoma, soft tissue sarcoma, maxillary cancer, lingual cancer, lip cancer, mouth cancer, melanoma, or non-melanoma skin cancer. In general, cancers that can be treated by the compounds and candidate compounds described herein include but are not limited to carcinomas, sarcomas, lymphomas, leukemias, or germ cell tumors. In preferred embodiments, the compounds described herein can be administered to a patient diagnosed with cervical cancer, breast cancer, prostate cancer, lung cancer, epithelial carcinoma, colorectal cancer, Burkitt lymphoma, myeloid leukemia, and leukemic monocyte lymphoma.

Administration and Dosing

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, or other compound can include a single treatment or, preferably, can include a series of treatments.

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Identifying Subjects for Treatment

In some embodiments, the methods include (i) identifying and selecting an individual suffering from cancer, and optionally (ii) determining if the individual's cancer cells express high levels of Hsp90 chaperones in the mitochondria. If these cells express high levels of Hsp90 chaperones in the mitochondria, then the individual is a candidate for, i.e., can be selected for, treatment with a mitochondrial-targeted chaperone inhibitor, and the method further includes (iii) administering to the individual a pharmaceutical composition including a mitochondrial-targeted chaperone inhibitor.

Individuals with cancer can be identified using methods known in the art, e.g., because they display symptoms or as a result of screening. Additional clinical tests can be performed and include, but are not limited to, blood tests, X-rays, CT scans, endoscopy, and histological examination of biopsy tissue, to confirm the diagnosis.

Symptoms of cancer in an individual include, but are not limited to, unusual lumps or swelling, hemorrhage, pain and/or ulceration, enlarged lymph nodes, cough and hemoptysis, hepatomegaly (enlarged liver), bone pain, fracture of affected bones and neurological symptoms, weight loss, poor appetite and cachexia (muscle wasting), excessive sweating, and anemia.

Screens for identifying individuals with cancer are known in the art. Screening methods include, but are not limited to, self-examination, mammograms, fetal occult blood testing, cervical cytology (e.g., Pap smear), digital rectal exam, prostate specific antigen (PSA) blood testing, sigmoidoscopy, which looks for visual abnormality in the rectum and lower part of the colon, and colonoscopy, which allows visualization of the rectum and entire colon, and double contrast barium enema (DCBE), which allows radiographic examination of the rectum and colon.

A number of methods are known in the art for detecting high levels of chaperones in the mitochondria, including immunoassays, e.g., using an antibody to Hsp90. For example, the detection of chaperones in mitochondria can be achieved by obtaining mitochondrial and submitochondrial fractions, followed by the use of known detection methods, such as Western blotting, immunoelectron microscopy with an antibody to Hsp90, and matrix-assisted laser desorption/ionization (MALDI) proteomics (e.g., mass spectroscopy and time-of-flight analysis) of mitochondrial fractions.

Additional methods of identifying individuals who are candidates for treatment with a chaperone inhibitor are disclosed herein. In these methods, a cancer cell from an individual is (i) exposed to a mitochondrial-targeted chaperone inhibitor and (ii) assayed for the presence of one or more of the following activities: increased cell death, loss of cell viability, loss of mitochondrial membrane potential, loss of mitochondrial membrane integrity (e.g., Smad or cytochrome c release), and loss of Hsp90 chaperone activity (e.g., degradation of Akt kinase). Methods for performing such assays are known in the art and include flow cytometry, the MTT assay, gel electrophoresis, and western blotting. Exemplary methods are also described in the Examples herein.

If the cancer cell exhibits one or more of these activities, then the individual is classified as a candidate for treatment with a mitochondrial-targeted chaperone inhibitor. In other new methods, cancer cells from the same individual are placed in culture media. Some of the cancer cells are contacted with a mitochondrial-targeted chaperone inhibitor, and cultured under conditions that allow the cells to proliferate. If the mitochondrial-targeted chaperone inhibitor inhibits proliferation and/or induces apoptosis of the contacted cancer cells, e.g., relative to cells that are not contacted with an inhibitor, then the individual is a candidate for treatment with mitochondrial-targeted chaperone inhibitor.

VI. Pharmaceutical Compositions

The mitochondrial-targeted chaperone inhibitors described herein (all of which can be referred to herein as "active compounds") can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions. Also included are the pharmaceutical compositions themselves, and pharmaceutically acceptable salts of the compounds described herein. It is well known in the pharmacological arts that nontoxic addition salts of pharmacologically active amine compounds do not differ in activities from their free base. Pharmaceutically acceptable salts include both acid and base addition salts. "Pharmaceutically acceptable salt" refers to those salts which retain the biological effectiveness and properties of the free bases and which are not biologically or otherwise undesirable. Suitable pharmaceutically acceptable acid addition salts can be formed with inorganic acids such as hydrochloric acid, hydrobromic acid, sulfuric acid, nitric acid, phosphoric acid, and the like, and organic acids such as acetic acid, propionic acid, glycolic acid, pyruvic acid, fumaric acid, tartaric acid, citric acid, benzoic acid, cinnamic acid, mandelic acid, methanesulfonic acid, and p-toluenesulfonic acid, and the like. Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines, including naturally occurring substituted amines, cyclic amines and basic ion exchange resins, such as isopropylamine, tripropylamine, ethanolamine, 2-diethylaminoethanol, 2-dimethylaminoethanol, dicyclohexylamine, lysine, arginine, histidine, caffeine, procain, hydrabamine, choline, betaine, ethylenediamine, glucosamine, methylglucamine, theobromine, purines, piperazines, piperidine, polyamine resins and the like. Particularly preferred organic non-toxic bases are isopropylamine, diethylamine, ethanol-amine and dicyclohexylamine.

A pharmaceutical composition is generally formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent which delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Although applicants do not wish to be bound by theory, any non-specific cytotoxic effects of a systemically administered mitochondrial-targeted chaperone inhibitor as described herein are expected to be minimal, for at least the following reasons: levels of mitochondrial Hsp90 and TRAP 1 are low in most normal tissue; as demonstrated herein, mitochondrial localization of Hsp90 and TRAP-1 is generally tumor cell-specific, so that the inhibitors will preferentially accumulate in the mitochondria of tumor cells; in those normal tissues that have mitochondrial-localized Hsp90 and TRAP-1, the activity of Hsp90 and TRAP-1 is decreased relative to the activity in tumor cells; and the blood-brain barrier is expected to protect the brain.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Nucleic acid molecules encoding a polypeptide described herein can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al., Proc. Natl. Acad. Sci. USA, 91:3054-3057, (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Modifications such as lipidation can be used to stabilize proteins and to enhance uptake and tissue penetration. A method for lipidation is described by Cruikshank et al., J. Acquired Immune Deficiency Syndromes and Human Retrovirology, 14:193, (1997).

The pharmaceutical compositions can be included in a container, pack, or dispenser together with instructions for administration.

VII. Nucleic Acids

Also included within the present disclosure are nucleic acids that encode peptide-based mitochondrial-targeted chaperone inhibitors as described herein.

Nucleic acids that are part of this invention can encode any of the peptides identified by the methods disclosed herein that bind to and inhibit mitochondrial Hsp90 chaperones, e.g., Hsp90 and TRAP-1. The nucleic acids disclosed herein also include nucleic acids encoding modified versions of peptides that bind to and inhibit mitochondrial Hsp90 chaperones, e.g., retro peptides, peptides linked to a heterologous polypeptide sequence, peptides linked to a mitochondrial-penetrating sequence, peptides linked to a cellular internalization sequence, and retro peptides linked to a mitochondrial-penetrating sequence.

In some embodiments, the nucleic acids encode mitochondrial-targeted chaperone inhibitors for use in gene therapy.

Nucleic acids disclosed herein include both RNA and DNA, including recombinant DNA isolated from a cell and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Also included in the invention are genetic constructs (e.g., vectors and plasmids) that include a nucleic acid encoding a mitochondrial-targeted chaperone inhibitor described herein operably linked to a transcription and/or translation sequence that enables expression of the mitochondrial-targeted chaperone inhibitor, e.g., expression vectors. A selected nucleic acid, e.g., a DNA molecule encoding a peptide described herein, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain, and optionally express, a nucleic acid disclosed herein. Prokaryotic and eukaryotic cells, e.g., mammalian cells (e.g., tumor cells), yeast, fungi, and bacteria (such as *Escherichia coli*), and primary and transformed cells, can be host cells. A number of suitable cells are known in the art.

VIII. Methods of Screening

Described herein are methods for identifying candidate compounds, e.g., small organic or inorganic molecules (e.g., having a M.W. less than 1,000 Da), oligopeptides, oligonucleotides, carbohydrates, and antibodies that are useful in the methods of treatment described herein. In some methods, a candidate compound is screened for its ability to bind a chaperone, e.g., Hsp90 or TRAP-1. In some methods, a candidate compound is screened for its ability to bind Cyclophilin D. In some methods, candidate compounds are screened in silico by computational methods (as described, for example, in Example 12, in order to identify candidate compounds that are expected to bind to Hsp90, e.g., the apo-open form of Hsp90). Libraries of chemical structures are known in the art.

These candidate compounds can optionally be linked (via covalent or non-covalent interactions) to the mitochondrial-penetrating moieties described herein. In some methods, a candidate compound is screened for its ability to inhibit an interaction between Cyclophilin D and a chaperone, e.g., Hsp90 or TRAP-1. In some methods, a candidate compound is screened for its ability to localize to mitochondria. In some methods, a candidate compound is screened for its ability to induce cell death.

Libraries of Test Compounds

In certain embodiments, screens for candidate compounds that can be used to treat cancer cells use libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. In some cases libraries include classes of compounds with enhanced potential for having anti-cancer activity. Classes of compounds with enhanced potential include known chaperone inhibitors and structurally similar compounds. For example libraries can include ansamycin antibiotics, geldanamycin analogs, and pyrazolopyrimidines and related analogs. A library can be designed and synthesized to cover such a class of chemicals.

The synthesis of combinatorial libraries has been reviewed (see, e.g., Gordon et al., J. Med. Chem., 37:1385, (1994); DeWitt and Czarnik, Acc. Chem. Res., 29:114, (1996); Armstrong et al., Acc. Chem. Res., 29:123-131, (1996); Ellman, J. A., Acc. Chem. Res., 29:132, (1996); Gordon et al., Acc. Chem. Res., 29:144, (1996); Lowe, G. Chem. Soc. Rev., 309, (1995), Blondelle et al., Trends Anal. Chem., 14:83, (1995); Chen et al., J. Am. Chem. Soc., 116:2661, (1994); U.S. Pat. Nos. 5,359,115, 5,362,899, and 5,288,514; and PCT Publication Nos. WO92/10092, WO93/09668, WO91/07087, WO93/20242, and WO94/08051).

Libraries of compounds can be prepared according to a variety of methods, some of which are known in the art. For example, a split-pool strategy can be implemented in the following way: beads of a functionalized polymeric support are placed in a plurality of reaction vessels; a variety of polymeric supports suitable for solid-phase peptide synthesis are known, and some are commercially available (for examples, see, e.g., Bodansky, *Principles of Peptide Synthesis,* 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, pooled (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a biased library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The split-pool strategy can result in a library of peptides, e.g., modulators, which can be used to prepare a library of test compounds for use in the screens described herein. In another illustrative synthesis, a diversomer library is created by the method of DeWitt et al., Proc. Natl. Acad. Sci. U.S.A., 90:6909, (1993). Other synthesis methods, including the "tea-bag" technique, described in Houghten et al., Nature, 354:84, (1991), can also be used to synthesize libraries of compounds according to the subject invention.

Libraries of compounds can be screened to determine whether any members of the library have chaperone, e.g., Hsp90 or TRAP-1, inhibitory activity, and, if so, to identify the inhibitor. Methods of screening combinatorial libraries have been described. See, e.g., Gordon et al., J. Med. Chem., supra. Soluble compound libraries can be screened to isolate inhibitors of chaperones, e.g., Hsp90 or TRAP-1, followed by identification of the isolated ligands by conventional techniques (e.g., mass spectrometry, NMR, and the like). Screens are described herein.

Screens

Provided herein are methods for identifying candidate compounds for the treatment of tumors or cancer. Although applicants do not intend to be bound by any particular theory as to the biological mechanism involved, such compounds are thought to inhibit chaperones in mitochondria thereby inhibiting chaperone-mediated antagonism of Cyclophilin D (CypD) function. Cyclophilin D is an immunophilin that induces mitochondrial cell death, and chaperones are thought to antagonize CypD function via protein folding/refolding mechanisms. Disabling this pathway using novel Hsp90 ATPase antagonists directed to mitochondria causes sudden collapse of mitochondrial function and selective tumor cell death. Thus, chaperones are novel regulators of mitochondrial integrity, and their organelle-specific antagonists may provide a novel class of potent anticancer agents.

In certain embodiments, screening for compounds capable of inhibiting chaperones in mitochondria can include identifying from a group of test compounds those that (i) inhibit and/or bind to a molecular chaperone, (ii) inhibit interaction between a molecular chaperone and Cyclophilin D, and/or (iii) decrease levels of chaperones in tumor cell mitochondria. Test compounds that exhibit one or more of activities (i), (ii), or (iii) are referred to herein as "candidate compounds." Screening assays can optionally include further testing candidate compounds for their ability to modulate proliferation of cancer cells in vitro or in vivo. Screening assays of the present invention may be carried out in whole cell preparations and/or in ex vivo cell-free systems. In some embodiments, test compounds or candidate compounds are linked to a mitochondrial-penetrating moiety.

Binding of a test compound to a cell-free sample that includes a chaperone protein can be detected, for example, in vitro by reversibly or irreversibly immobilizing the chaperone protein on a substrate, e.g., the surface of a well of a plate (e.g., 96-well polystyrene microtitre plate). For example, microtitre plates can be coated with the chaperone protein, or a fragment thereof, washed and blocked (e.g., with BSA) to prevent non-specific binding of test compounds to the plates. The chaperone protein is then cross-linked to the plate. Test compounds are added to the coated plate under a number of conditions (e.g., at 37° C. for 0.5-12 hours). The plate can then be rinsed and binding of the test compound to the chaperone protein can be detected by any of a variety of art-known methods. For example, an antibody that specifically binds to the chaperone protein can be used in an immunoassay. If desired, the antibody can be labeled (e.g., fluorescently or with a radioisotope) and detected directly (see, e.g., West and McMahon, J. Cell Biol., 74:264, (1977)). Alternatively, a second antibody can be used for detection (e.g., a labeled antibody that binds to the anti-chaperone protein antibody). Test compounds that bind to the chaperone protein can be detected by their ability to inhibit binding of antibody to immobilized chaperone protein. In an alternative detection method, the test compound is labeled (e.g., with a radioisotope, fluorophore, chromophore, or the like), and the binding of a test compound to the chaperone protein is detected by detecting label that is immobilized on the substrate.

In still another embodiment, test compounds are immobilized on a substrate, e.g., to a microtitre plate as described above, incubated with a cell free sample that includes a chaperone protein (or a fragment thereof), washed, and the ability of the chaperone protein to bind to an immobilized test compound is detected. For example, Hsp90 (or a fragment thereof) can be produced as a fusion protein with a protein that can be detected optically, e.g., green fluorescent protein or a variant thereof (which can be detected under UV light), and the ability of the fusion protein to bind the test compound is detected. Alternatively, a chaperone can be produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins). In these methods, the ability of the chaperone fusion protein to bind to a test compound is detected.

To identify polypeptides that bind to a chaperone protein a two-hybrid assays of protein/protein interactions can be used (see, e.g., Chien et al., Proc. Natl. Acad. Sci. USA, 88:9578, (1991); Fields et al., U.S. Pat. No. 5,283,173; Fields and Song, Nature, 340:245, (1989); Le Douarin et al., Nucleic Acids Research, 23:876, (1995); Vidal et al., Proc. Natl. Acad. Sci. USA, 93:10315-10320, (1996); and White, Proc. Natl. Acad. Sci. USA, 93:10001-10003, (1996)). Kits for practicing various two-hybrid methods are commercially available (e.g., from Clontech; Palo Alto, Calif.).

In certain other embodiments, the interaction of a chaperone protein, or fragment thereof, and test compound is detected by fluorescence resonance energy transfer (FRET) between a donor fluorophore covalently linked to either the chaperone protein or the test compound and an acceptor fluorophore covalently linked to either the chaperone protein or the test compound, wherein the acceptor and donor fluorophore are not both linked to the chaperone protein or the test compound, and there is suitable overlap of the donor emission spectrum and the acceptor excitation spectrum to give efficient nonradiative energy transfer when the fluorophores are brought into close proximity through the chaperone protein-test compound interaction.

In some methods, test compounds that are candidate compounds for the treatment of tumors or cancer can be identified by contacting a test compound to a sample that includes one or more chaperone proteins and CypD, and then screening for decreased interaction between a chaperone and CypD. In one embodiment, a cell-free system is used to determine if recombinant TRAP-1 or recombinant Hsp90 co-immunoprecipitate with recombinant CypD in the presence of a test compound.

In some methods, test compounds that are candidate compounds for the treatment of tumors or cancer are contacted with one or more tumor cells and are evaluated for decreased expression of the chaperone. In a related method, one or more test compound is contacted to a tumor cell that expresses a recombinant chaperone, and the cells are evaluated for decreased expression of the recombinant chaperone. Expression of a chaperone can be measured, for example, by Northern blot, RT-PCR analysis, RNAse protection analyses, Western blot, enzyme-linked immunosorbent assay (ELISA), radioimmunoassay (MA) and fluorescent activated cell sorting (FACS). The level of expression in the presence of the test molecule, compared with the level of expression in its absence, will indicate whether or not the test compound inhibits the expression of the chaperone. In one embodiment, the test compound is a small interfering RNA (siRNA).

Having identified a test compound as a candidate compound, the candidate compound can be further tested, e.g., in proliferation assays of tumor cells using in vitro or in vivo model systems. In vitro proliferation assays include contacting a candidate compound to a culture of tumor cells, e.g., Raji cells, and evaluating the ability of the candidate compound to induce apoptosis in and/or prevent proliferation of the cultured cells. In vivo tumor assays include administering a candidate compound to an animal model, e.g., a rodent, with a tumor or a predisposition to develop a tumor, and subsequently evaluating the candidate compound's ability to inhibit tumor development or tumor proliferation in the animal. Exemplary animal models of cancer include animals with xenografted cancer cells. Other animal models include rodents with a genetic predisposition to develop tumors, e.g., mice bearing mutant forms of (i) adenomatous polyposis coli (APC) gene (e.g., a multiple intestinal neoplasia ($APC^{Min}$) mouse (see, e.g., Haigis et al., Proc. Nat'l. Acad. Sci. USA, 101:9769-9773, (2004)), (ii) mut-s homologue-2 (Msh2) gene (see, e.g., Kohonen-Corish et al., Cancer Research, 62:2092-2097, (2002)), and/or (iii) MutL homologue-1 (Mlh1) gene (see, e.g., Cohen et al., Cell, 85:1125-1134, (1996)). The C57BL/6J-$Apc^{Min}$ mouse is available from Jackson Harbor Labs (Bar Harbor, Me.). Alternatively, an animal model can be exposed to carcinogenic chemicals such as dimethylhydrazine derivatives or heterocyclic amines, such as 2-amino-1-methyl-6-phenylimidazo[4,5-b]pyridine (PhIP), that have been reported to induce tumors in animal models.

In some methods, candidate compounds for the treatment of tumors or cancer can be further tested for apoptosis-inducing activity by contacting the candidate compound to a sample that includes one or more tumor cells, and then screening for decreased cell viability. In one embodiment, decreased cell viability is measured using an MTT (344,5-dimethylthiazol-2-yl)-2,5-diphenyltetrazolium bromide) reduction assay. The colorimetric MTT assay, developed by Mossman (J. Immunol. Methods 65:55-63 (1983)), is based on the conversion of the water-soluble MTT to an insoluble purple formazan. The formazan is then solubilized, and its concentration determined by optical density at 570 nm. The methods can be performed, e.g., as described in Plescia et al. (Cancer Cell. 2005 May; 7(5):457-68). Other viability assays can also be used.

In some methods, candidate compounds for the treatment of tumors or cancer can be further tested by contacting a test compound to a sample that includes one or more tumor cells, and then screening for increased apoptosis. In one embodiment, increased apoptosis is evident as increased caspase activity as determined by DEVDase hydrolysis. Methods for measuring apoptosis are well known in the art.

In some methods, candidate compounds for the treatment of tumors or cancer can be further tested for their ability to disrupt mitochondrial membrane integrity. For example, candidate compounds can be further tested for their ability to induce a change in mitochondrial membrane potential, increase cytochrome c release, or increase Smad release. In one embodiment, cells are treated with a candidate compound and further treated with a mitochondrial membrane potential-sensitive fluorescent dye JC-1, and analyzed for changes in green/red fluorescence ratio by flow cytometry.

In some methods, candidate compounds for the treatment of tumors or cancer can be further tested for their ability to inhibit chaperone activity. For example, candidate compounds can be further tested for their ability to induce degradation of Akt, an Hsp90 client protein.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry can modify moieties on a candidate compound or agent (i.e., a lead compound) and measure the effects of the modification on the efficacy of the compound or agent to thereby produce derivatives with increased potency. For an example, see Nagarajan et al., J. Antibiot., 41:1430-1438, (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

EXAMPLES

The invention is further described in the following examples, which do not limit the scope of the invention described in the claims.

Example 1: Hsp90 Chaperones in Mitochondria

The experiments described in this example were designed to determine subcellular localization of the chaperones TRAP-1 and Hsp90.

An antibody to TRAP-1 detected an abundant ~75 kDa immunoreactive band in purified mitochondria isolated from various tumor cell types (FIG. 1A). This localization was selective because TRAP-1 was found at very low levels in mitochondria isolated from normal mouse tissues (FIG. 1A), and was absent in the cytosol of tumor or normal cells (FIG. 1A and not shown) (Chen et al., Mol. Cell. Biol., 16:4691-4699, (1996)). Differential TRAP-1 expression in primary tumor specimens and their respective normal tissues, in vivo, were examined. By immunohistochemistry, TRAP-1 was intensely expressed in the tumor cells of adenocarcinoma of the pancreas (FIG. 1C), breast (FIG. 1E), colon (FIG. 1G), and lung (FIG. 1I). Conversely, epithelia of normal pancreas (FIG. 1B), breast (FIG. 1D), colon (FIG. 1F), and lung (FIG. 1H) contained very low levels of TRAP-1, and IgG did not stain normal or tumor tissues (not shown).

Figure 2A:
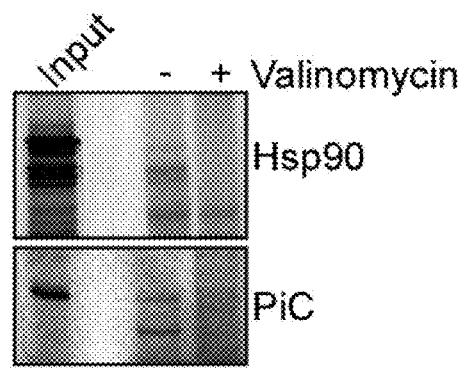
FIG. 2A is a set of two autoradiographs of extracts from purified mouse brain mitochondria incubated with $^{35}$S-labeled, in vitro transcribed and translated Hsp90 or control PiC with or without valinomycin and treated with proteinase K (PK) showing levels of radiolabeled Hsp90 or control PiC following treatment.

In addition to its known localization in cytosol, an abundant pool of Hsp90 was detected in mitochondria of various tumor cell types, by Western blotting (FIG. 1J). Accordingly, an antibody to Hsp90 labeled purified mitochondria isolated from HeLa cells (26.6±4.1 gold particles/mitochondria, n=13), by electron microscopy (FIG. 1K), whereas IgG did not significantly stain mitochondria (1.1±0.33 gold particles/mitochondria, n=13; p<0.0001) (FIG. 1L). Mitochondria were characterized as follows. Mitochondrial fractions purified from HeLa cells contained TRAP-1 and Hsp90, but not proteins of the endoplasmic reticulum (calnexin), or cytosol (GAPDH), and very low amounts of Lamp-1, a lysosomal marker (FIG. 1M). Hsp90 was actively imported in isolated mitochondria. $^{35}$S-labeled in vitro transcribed and translated Hsp90 proteins readily accumulated inside isolated brain mitochondria after treatment with proteinase K, and this reaction was completely inhibited by the uncoupler, valinomycin (FIG. 2A). Similar results were obtained with $^{35}$S-labeled mitochondrial phosphate carrier, PiC, as a control for mitochondrial import (FIG. 2A).

Figure 8:
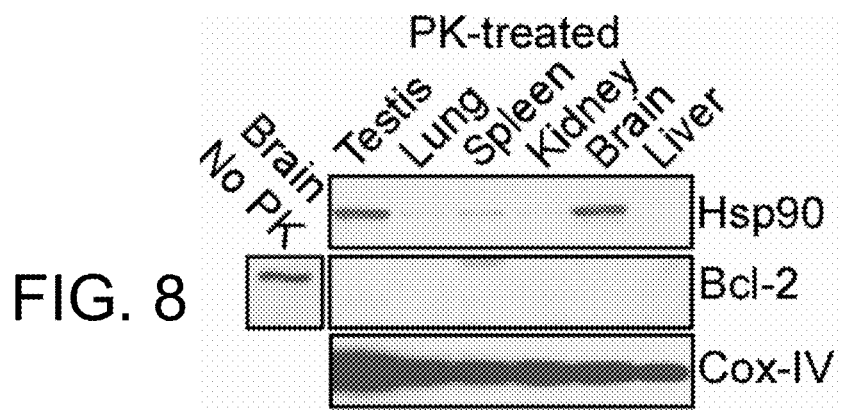
FIG. 8 is a set of four immunoblots. The top panel is an Hsp90 immunoblot of proteinase K (PK) treated mitochondria isolated from testis, lung, spleen, kidney, brain, and liver, showing minimal expression in testis and brain, only. Bcl-2 (middle panels) and Cox-IV (bottom panel) immunoblots were used as negative and positive controls, respectively. A Bcl-2 immunoblot in brain mitochondria without PK treatment was also used as a positive control (panel to left).

To determine if Hsp90 localized to mitochondria in vivo, immunoblots were performed on mitochondrial extracts obtained from primary testis, lung, spleen, kidney, brain and liver cells. These immunoblots showed that Hsp90 is expressed at low levels in the mitochondria of primary cells (FIG. 8). Proteinase K degradation of outer membrane proteins, including Bcl-2, did not reduce Hsp90 reactivity in isolated mitochondria (FIG. 8), suggesting that it was protected from proteolysis.

Figure 2B:
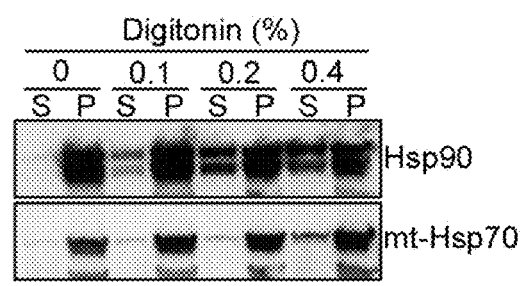
FIG. 2B is a pair of immunoblots of pellets (P) or supernatants (S) from PK treated HeLa cell mitochondria incubated with varying concentrations of digitonin showing protein levels of Hsp90 and mt-Hsp70 as control.
Figure 2C:
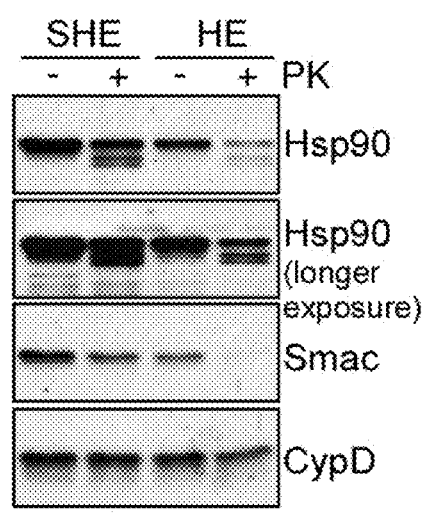
FIG. 2C is a set of four immunoblots of the protein content of HeLa cell mitochondria suspended in buffer with (SHE) or without (HE) sucrose in the presence or absence of PK and having outer mitochondrial membrane mechanically disrupted by repeated pipetting showing protein levels of Hsp90, Smac, and CypD.
Figure 2D:
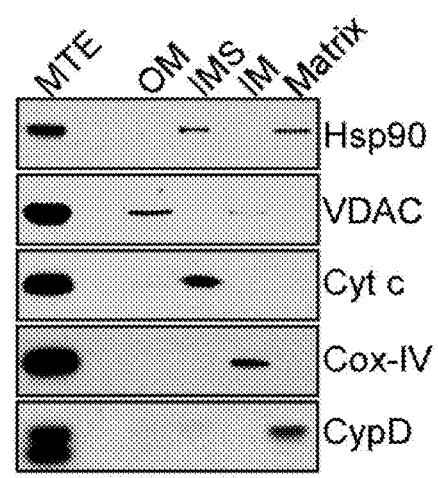
FIG. 2D is a set of five immunoblots of total mitochondrial extracts (MTE) from HeLa cells, further fractionated outer membrane extracts (OM), intermembrane space extracts (IMS), inner membrane extracts (IM) and mitochondrial matrix extracts (Matrix) showing protein levels of Hsp90, VDAC, Cyt c, Cox-IV, and CypD.

Conversely, permeabilization of the outer membrane with digitonin resulted in concentration dependent release of Hsp90 from mitochondrial pellets into the supernatant, whereas matrix associated mt-Hsp70 was unaffected (FIG. 2B). In the absence of sucrose, mechanical disruption of the outer membrane completely depleted Smac from the mitochondrial intermembrane space, without affecting matrix-associated Cyclophilin D (CypD) (FIG. 2C). Although reduced by this treatment, substantial Hsp90 reactivity remained associated with mitochondria (FIG. 2C), suggesting that Hsp90 localized to both the matrix and the mitochondrial intermembrane space. A submitochondrial fractionation protocol that allows analysis of individual organelle compartments, including the outer membrane (OM), intermembrane space (IMS), inner membrane (IM) and the matrix was used to examine localization of Hsp90. Hsp90 localized to both the intermembrane space and the mitochondrial matrix (FIG. 2D).

Figure 2E:
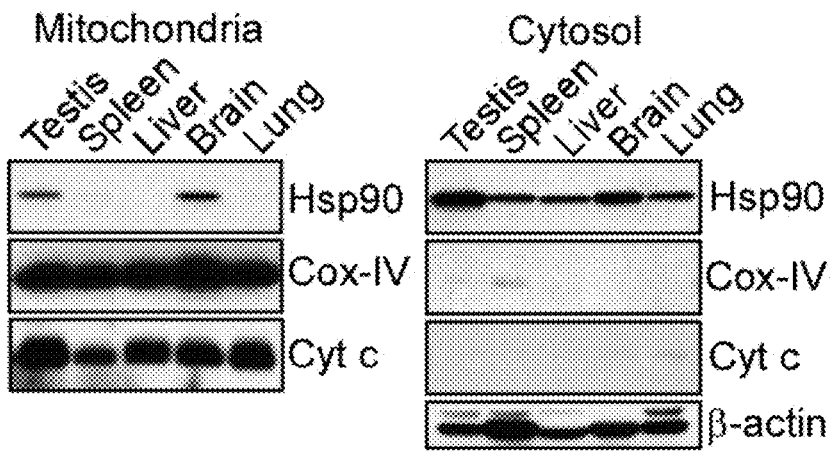
FIG. 2E is a set of seven immunoblots of mouse organs fractionated into mitochondria (left) or cytosol (right), showing protein levels of Hsp90, Cox-IV, and Cyt c. β-actin is a cytosolic control.
Figure 2F:
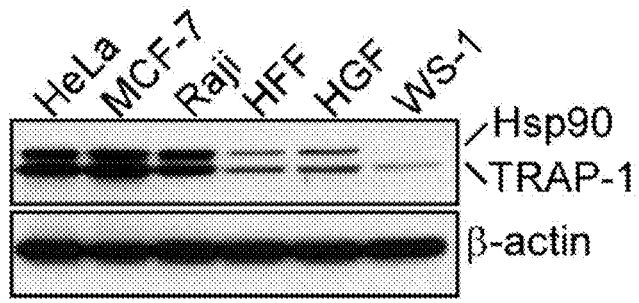
FIG. 2F is a pair of immunoblots of total cell extracts from tumor (HeLa, MCF-7, Raji) or normal (HFF, HGF, WS-1) cells showing Hsp90 and TRAP-1 levels. β-actin is a control.
Figure 2G:
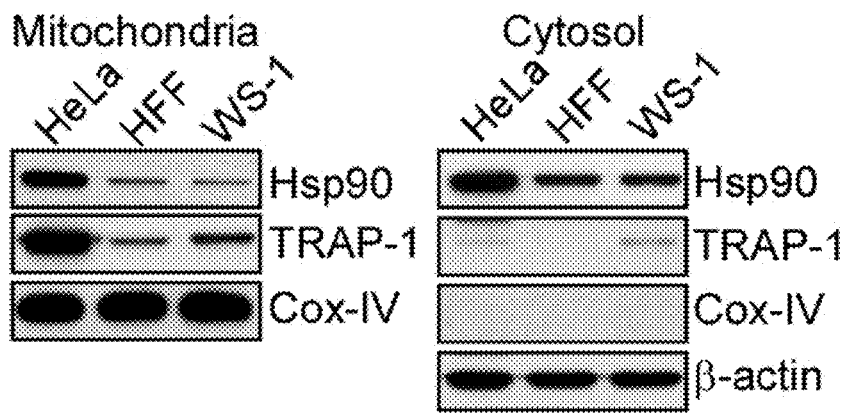
FIG. 2G is a set of seven immunoblots of indicated normal cell types or control HeLa cells fractionated in mitochondria (left three blots) or cytosolic extracts (right four blots), showing levels of Hsp90, TRAP-1, and Cox-IV. β-actin is a control.

Similar to TRAP-1, the mitochondrial localization of Hsp90 was selective, and, except for brain and testis, no expression of mitochondrial Hsp90 was found in other normal mouse tissues surveyed (FIG. 2E). Further, levels of mitochondrial Hsp90 in brain and testis was significantly lower than mitochondrial Hsp90 levels observed for tumor cell types (FIG. 1J). Conversely, the cytosolic pool of Hsp90 was ubiquitously present in normal and tumor cell types (FIG. 2E). In human cells, both Hsp90 and TRAP-1 were expressed at high levels in various tumor cell lines, but expressed at low levels in three normal primary fibroblast cell types (FIG. 2F). This differential localization was not due to a globally reduced expression of Hsp90 chaperones in normal versus tumor cells. The cytosolic amount of Hsp90 in normal cells was comparable to that of a representative tumor cell type, whereas its mitochondrial pool was considerably reduced, and TRAP-1 levels in mitochondria were also decreased (FIG. 2G).

Example 2: Targeting Mitochondrial Hsp90 Chaperones Causes Mitochondrial Permeability Transition and Cell Death In the experiments described in this example, two ATPase pocket antagonists of Hsp90 chaperones were used, the small molecule GA derivative, 17-AAG (Isaacs et al., Cancer Cell, 3:213-217, (2003)), and the peptidomimetic Shepherdin (Sheph), which is made cell permeable by the addition of an Antennapedia helix III homeodomain cell-penetrating sequence ("ANT", Plescia et al., Cancer Cell, 7:457-468, (2005)). Both molecules inhibit Hsp90 chaperone activity by competing with ATP binding and inhibiting Hsp90 ATPase activity (Neckers and Ivy, Curr. Opin. Oncol., 15:419-424, (2003); Plescia et al., Cancer Cell, 7:457-468, (2005)).

Purified mitochondria were isolated from HeLa cells as described below. Fluorescein-conjugated Sheph-ANT accumulated inside the purified mitochondria (FIG. 3A), whereas no fluorescence signal was detected for Shepherdin lacking the Antennapedia cell-penetrating sequence, Sheph (FIG. 3B), or in the absence of mitochondria (FIG. 3C). A fluorescein-conjugated cell-permeable scrambled peptidomimetic, Scram-ANT, also accumulated inside isolated mitochondria (FIG. 3D), and quantification of fluorescence intensity showed that both Sheph-ANT and Scram-ANT sequence were indistinguishable for efficiency of intramitochondrial penetration (FIG. 3E) in the isolated mitochondria.

Figure 3G:
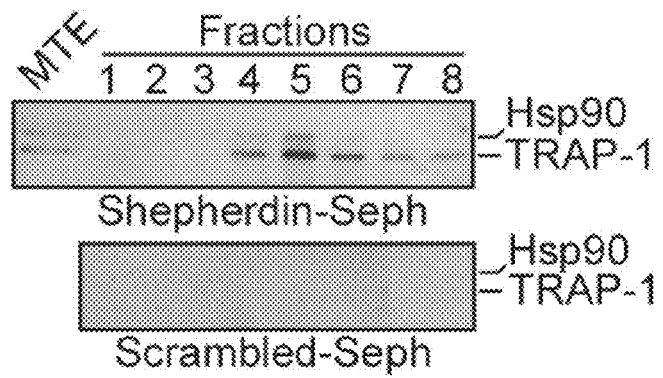
FIG. 3G is a pair of immunoblots of eluted fractions from Raji mitochondrial extracts (MTE) fractionated over Shepherdin-Sepharose (top) or scrambled peptidomimetic-Sepharose (bottom) beads, showing that Hsp90 and TRAP-1 are bound by Shepherdin-Sepharose and not scrambled peptidomimetic-Sepharose.

The submitochondrial distribution of Shepherdin with (Sheph-ANT) or without (Sheph) Antennapedia cell-penetrating peptide was quantified. Cell permeable Sheph-ANT was present in unfractionated mitochondria, as well as in all submitochondrial compartments, including the intermembrane space, the inner membrane and the matrix (FIG. 3F). This localization was entirely dependent on the Antennapedia peptide (ANT), as Sheph (without ANT) was not found in mitochondria or any sub-mitochondrial compartment (FIG. 3F). To determine whether Shepherdin directly bound Hsp90 molecules in mitochondria in vivo, we next coupled Shepherdin or scrambled peptidomimetic to Sepharose beads. Fractionation of Raji mitochondrial extracts over Shepherdin-Sepharose resulted in the specific elution of both TRAP-1 and Hsp90, by Western blotting (FIG. 3G; top). In contrast, no association of Hsp90 molecules with immobilized scrambled peptidomimetic was demonstrated (FIG. 3G; bottom).

Figure 3H:
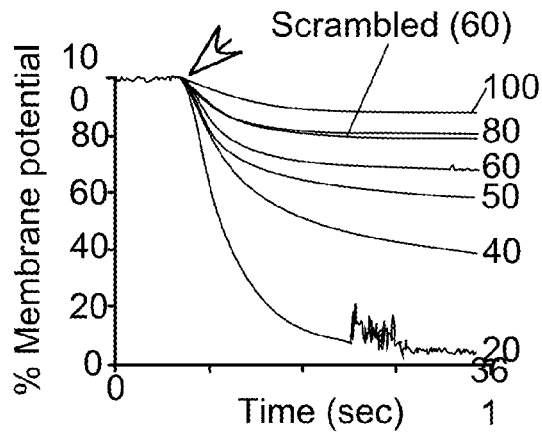
FIG. 3H is a line graph of mitochondrial membrane potential over time given increasing concentrations (µg) of TMRM-loaded mitochondria purified from HeLa cells incubated with Sheph-ANT and analyzed for changes in fluorescence emission, showing that Sheph-ANT induces a change in mitochondrial membrane potential and that the effect decreases with increasing concentrations of mitochondria. A scrambled peptidomimetic (Scram-ANT) was incubated with 60 µg of TMRM-loaded mitochondria as control.
Figure 3I:
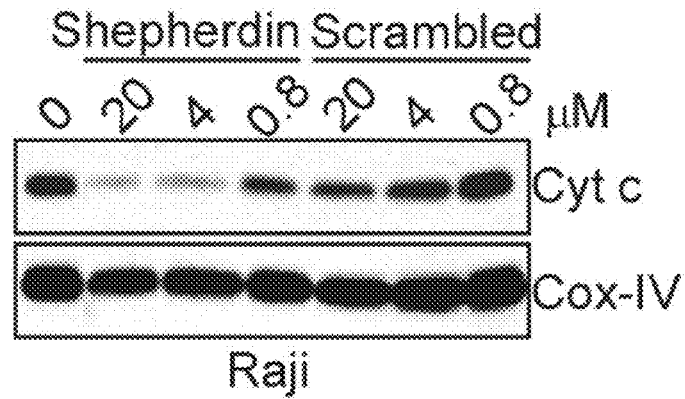
FIG. 3I is a pair of immunoblots of extracts from purified mitochondria of Raji cells treated with Sheph-ANT or Scram-ANT, showing that Sheph-ANT treatment reduces mitochondrial Cyt c in a dose-dependent manner.
Figure 3J:
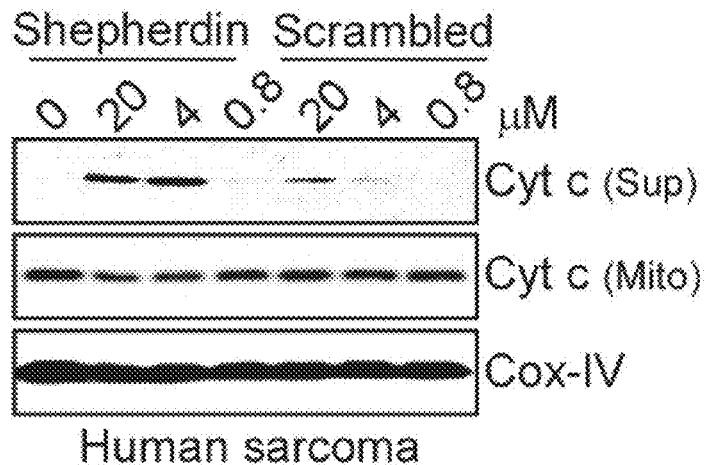
FIG. 3J is a set of three immunoblots of extracts from a primary human sarcoma sample obtained by treating sample with Sheph-ANT or Scram-ANT and fractionating mitochondria (Mito) from supernatant (Sup), showing that Sheph-ANT treatment increases Cyt c release into the supernatant in a dose-dependent manner.
Figure 3K:
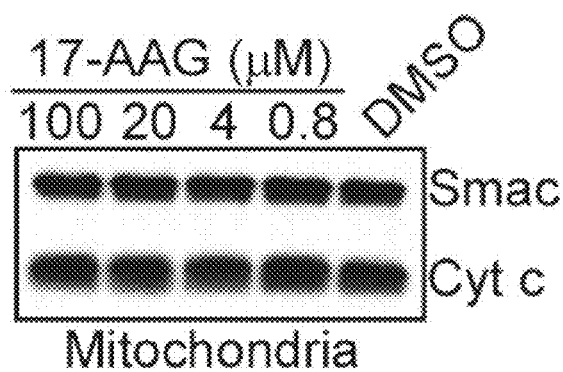
FIG. 3K is an immunoblot of HeLa cell mitochondria incubated with DMSO or 17-AAG, showing protein levels of inner mitochondrial membrane proteins Smac and Cyt c.
Figure 3L:
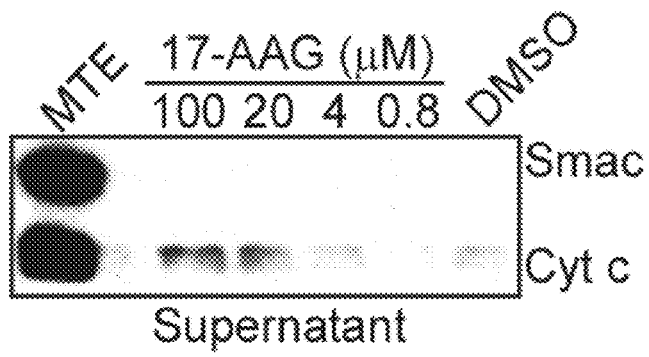
FIG. 3L is an immunoblot of supernatants from 17-AAG-treated HeLa cell mitochondria, showing Smac and Cyt c levels in the supernatant. Mitochondrial extract (MTE) is used as a control.
Figure 4A:
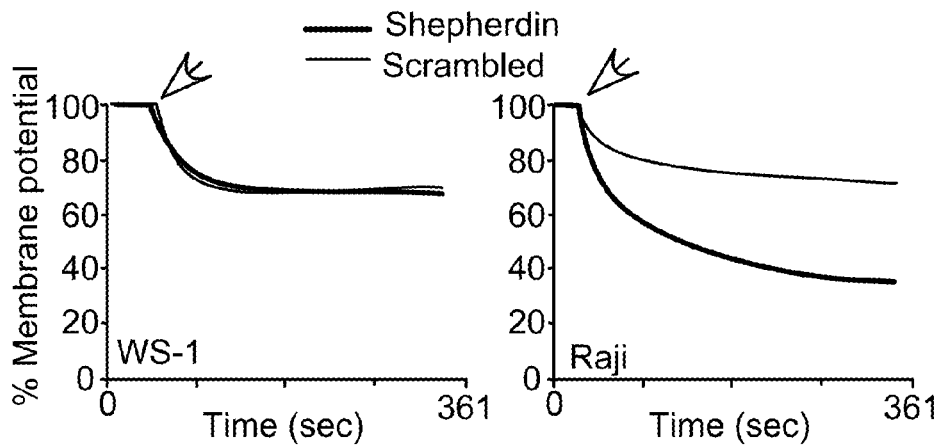
FIG. 4A are two line graphs showing mitochondrial membrane potential over time following the addition of Sheph-ANT or Scram-ANT in primary WS-1 fibroblasts (left) or Raji lymphoblastoid cells (right).

Under these experimental conditions, addition of Sheph-ANT to purified HeLa cell mitochondria caused sudden loss of mitochondrial membrane potential (FIG. 3H). This response was progressively attenuated at increasing mitochondria concentrations (FIG. 3H), suggesting a requirement for compound accumulation inside mitochondria. Conversely, Sheph-ANT did not affect mitochondrial membrane potential of normal cells over background levels (see below, FIGS. 4A, C, E, G), and a scrambled peptidomimetic (Scram-ANT) had no significant effect on mitochondrial membrane potential of tumor or normal cells (FIG. 3H and see below, FIGS. 4A, C, E, G). In addition, Sheph-ANT-induced concentration-dependent release of cytochrome c from mitochondria isolated from Raji lymphoblastoid cells (FIG. 3I), and a primary human sarcoma sample, in vivo (FIG. 3J), whereas Scram-ANT had no significant effect (FIGS. 3I, J). At variance with these data, the Hsp90 antagonist 17-AAG did not induce cytochrome c or Smac release from isolated tumor mitochondria (FIG. 3K), and only at high concentrations (20 μM), it caused a small discharge of mitochondrial cytochrome c, but not Smac, in the supernatant (FIG. 3L).

Figure 4B:
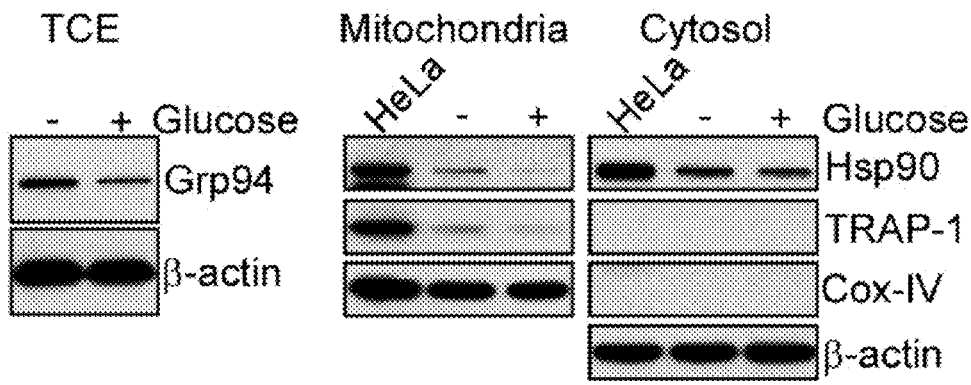
FIG. 4B shows three sets of immunoblots of total cell extracts (TCE, two blots on the left) or extracts from isolated mitochondrial (middle set of three blots) and cytosolic (right hand set of four blots) fractions obtained after incubating normal WS-1 fibroblasts or HeLa cells in the presence (+) or absence (−) of glucose, showing protein levels of Hsp90, TRAP-1, or Grp94. CoxIV and β-actin are controls.
Figure 4C:
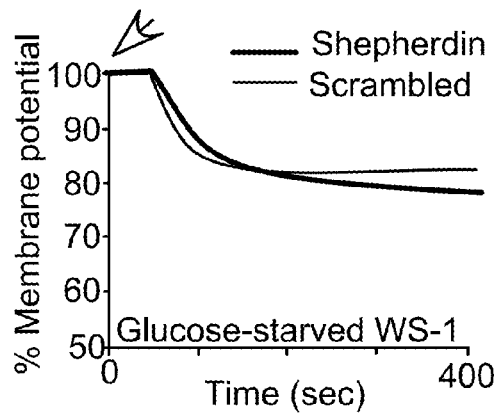
FIG. 4C is a graph of mitochondrial membrane potential over time following the addition of Sheph-ANT or Scram-ANT to TMRM-loaded mitochondria isolated from glucose-starved WS-1 fibroblasts.

Example 3: Differential Regulation of Mitochondrial Homeostasis in Tumor Versus Normal Cell Types Sheph-ANT did not cause loss of membrane potential of mitochondria isolated from WS-1 normal human fibroblasts (FIG. 4A, left), whereas it readily depolarized mitochondria purified from B-lymphoblastoid Raji cells (FIG. 4A, right). Scram-ANT did not have significant effect on normal or tumor mitochondria (FIG. 4A). Hsp90 levels can be modulated by cellular stress. Glucose deprivation of WS-1 fibroblasts increased the levels of the endoplasmic reticulum Hsp90 homolog, Grp94, used as a control (FIG. 4B, left). However, there were minimal changes in endogenous TRAP-1 and Hsp90 expression in WS-1 mitochondria after glucose deprivation (FIG. 4B, right). Consistent with this, Sheph-ANT did not significantly affect membrane potential of glucose-deprived WS-1 mitochondria, as compared with Scram-ANT (FIG. 4C).

Figure 4D:
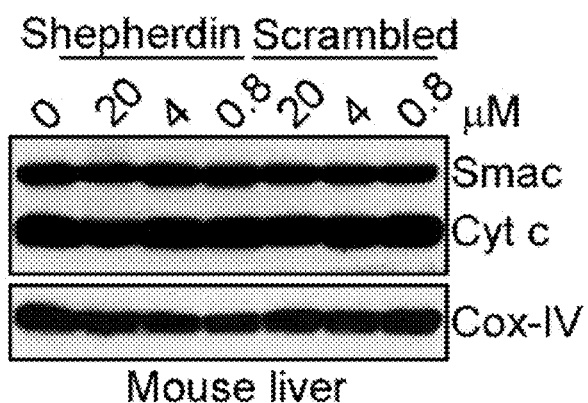
FIG. 4D is a pair of immunoblots of extracts from isolated mitchondria from normal mouse liver incubated with Sheph-ANT or Scram-ANT.
Figure 4E:
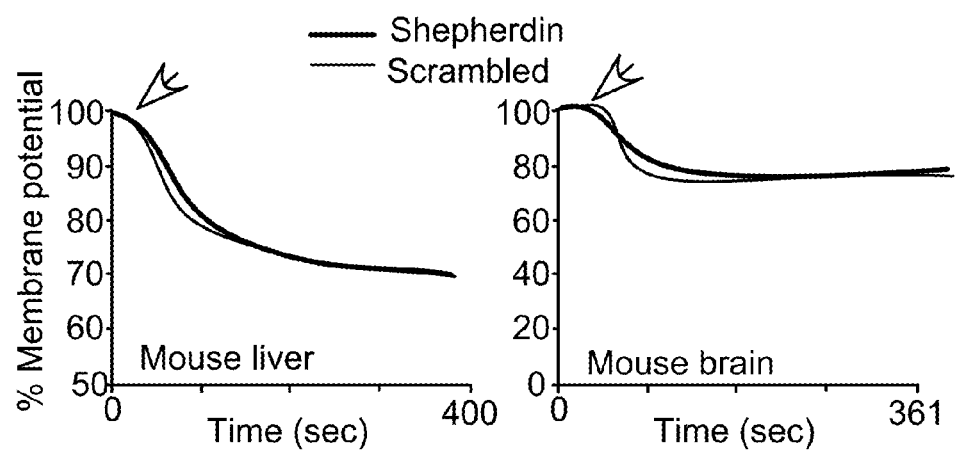
FIG. 4E is two line graphs of mitochondrial membrane potential over time following the addition of Sheph-ANT or Scram-ANT to TMRM-loaded mitochondria isolated from normal mouse liver (left) or normal mouse brain (right).
Figure 9:
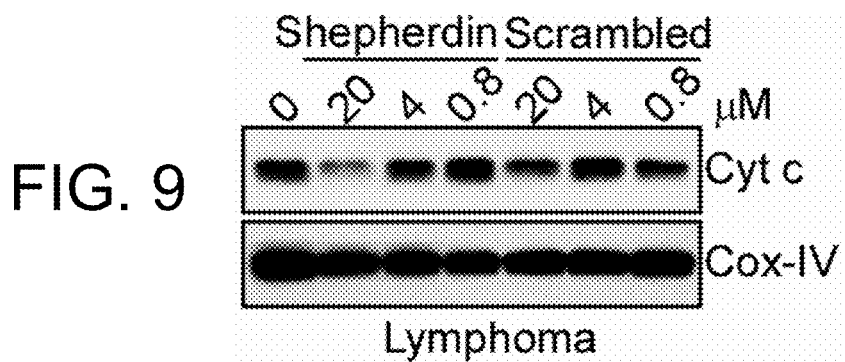
FIG. 9 is a pair of immunoblots. The upper panel is a Cyt c immunoblot of extracts prepared from mitochondria isolated from primary p53−/− mouse lymphoma specimen and incubated with Sheph-ANT or Scram-ANT. A Cox-IV immunoblot was used as a positive control (lower panel).

Sheph-ANT-induced cytochrome c release from mitochondria isolated from a p53$^{-/-}$ mouse lymphoma specimen (FIG. 9); this treatment had no effect on cytochrome c or Smac levels of normal mouse liver mitochondria (FIG. 4D), and did not affect membrane potential of normal mouse liver (FIG. 4E, left), or brain (FIG. 4E, right) mitochondria. A control scrambled peptidomimetic, Scram-ANT, did not have a significant effect on normal or tumor mitochondria (FIG. 9, FIG. 4D, E).

Figure 4F:
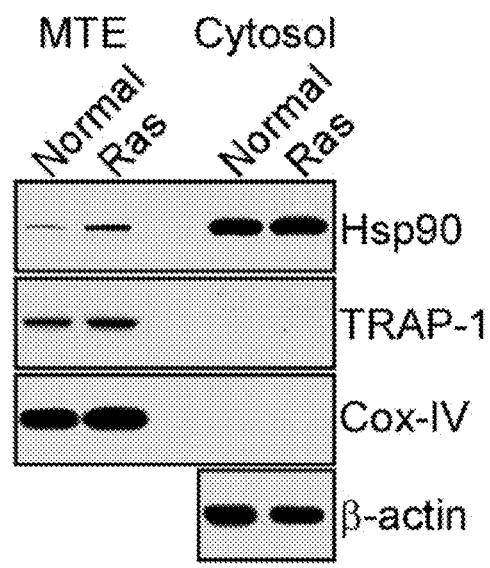
FIG. 4F is a set of four immunoblots of mitochondrial (MTE) or cytosolic extracts from wildtype NIH3T3 (normal) or Ras-transformed NIH3T3 fibroblasts, showing Hsp90, TRAP-1 protein levels. Cox-IV and β-actin are controls.
Figure 4G:
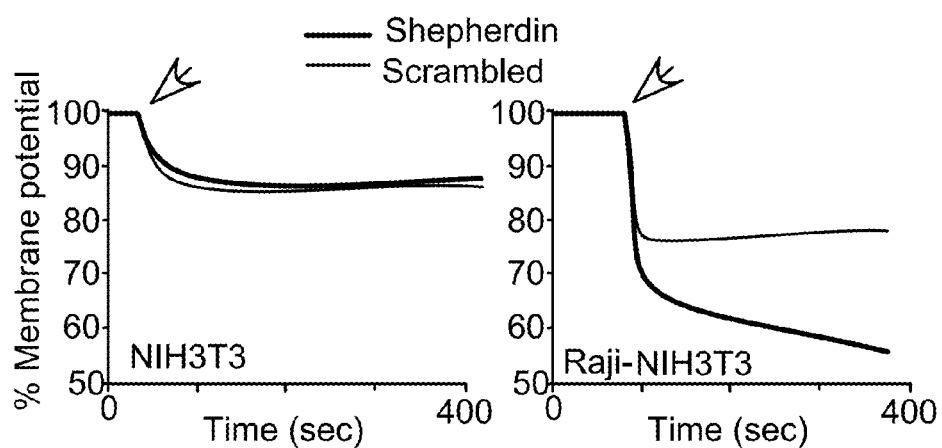
FIG. 4G consists of two line graphs of mitochondrial membrane potential over time following addition (at arrow) of Sheph-ANT or Scram-ANT to TMRM-loaded mitochondria isolated from NIH3T3 (left) or Ras-transformed NIH3T3 (right) fibroblasts, showing that Sheph induces loss of mitochondrial membrane potential in transformed cells.

To examine the basis for the differential recruitment of Hsp90 molecules to tumor versus normal mitochondria, the effect of oncogene expression on Hsp90 localization and expression levels were examined. Normal NIH3T3 fibroblasts exhibited low levels of mitochondrial Hsp90 (FIG. 4F). However, retroviral transduction of these cells with a mutant Ras oncogene resulted in increased recruitment of Hsp90 to mitochondria, whereas TRAP-1 expression increased less prominently (FIG. 4F). Conversely, cytosolic Hsp90 levels did not change in normal or Ras-transformed NIH3T3 cells (FIG. 4F). Sheph-ANT had no effect on mitochondria isolated from normal NIH3T3 cells (FIG. 4Q left), whereas it readily depolarized Ras-transformed NIH3T3 mitochondria (FIG. 4Q right), similarly to established tumor cells.

Example 4: Differential Regulation of Tumor Cell Killing by Inhibition of Mitochondrial Hsp90 Molecules Sheph-ANT was shown to selectively kill tumor cells. Fluorescein-conjugated Sheph-ANT accumulated in the perinuclear area of tumor cells, and co-localized with the reactivity of a mitochondrial marker, MitoTracker, by confocal microscopy (FIG. 5A). Although Scram-ANT accumulated inside isolated, purified mitochondria (FIG. 3D, E), Scram-ANT did not colocalize with MitoTracker in intact, living cells (FIG. 5B). These results suggest that while Scram-ANT is competent for penetrating mitochondria (as indicated by accumulation in isolated mitochondria), Scram-ANT does not accumulate to levels detectable by confocal microscopy in mitochondria in situ (in cells). Although applicants do not wish to be bound by theory, the inability to detect accumulation of Scram-ANT in mitochondria in situ may reflect non-specific penetration of Scram-ANT in other cytosolic membranous compartments, e.g., an equilibrium distribution of the Scram-ANT throughout the compartments of the cell, thereby reducing steady state levels of mitochondrially-localized Scram-ANT beyond the limit of detection of confocal microscopy. Again, not wishing to be bound by theory, the accumulation of the Sheph-ANT is likely to be due to tight binding of the Sheph moiety to Hsp90 or TRAP-1 localized inside the mitochondria. Consistent with this prediction, quantification of fluorescence intensity revealed that Scram-ANT accumulation in mitochondrial extracts of treated cells was reduced, as compared to Sheph-ANT (FIG. 5C). Conversely, both sequences comparably accumulated in total cell extracts and cytosol fractions of treated cells (FIG. 5C).

Figure 5F:
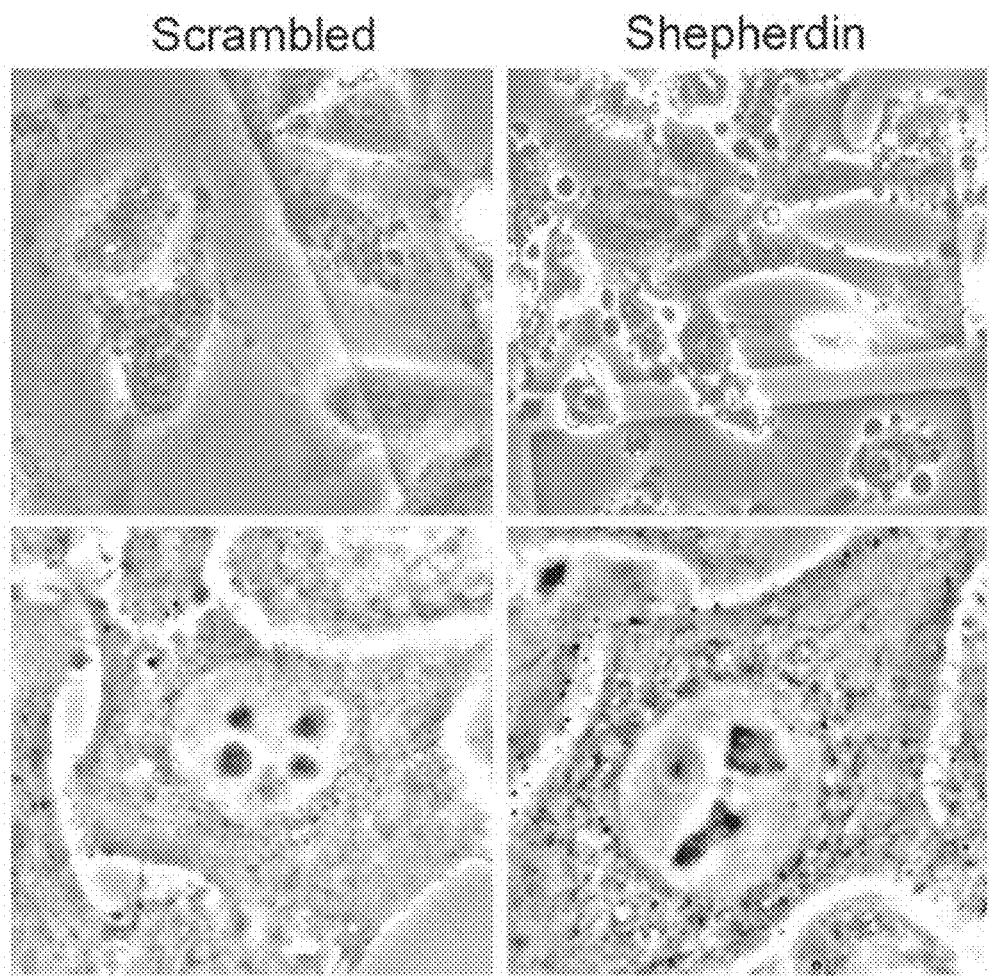
FIG. 5F panels are time-lapse video microscopy still images of HeLa cells treated with Sheph-ANT or Scram-ANT showing cellular morphology of apoptosis (top, right panel) or mitochonria fusion/fission (bottom, right panel).
Figure 5G:
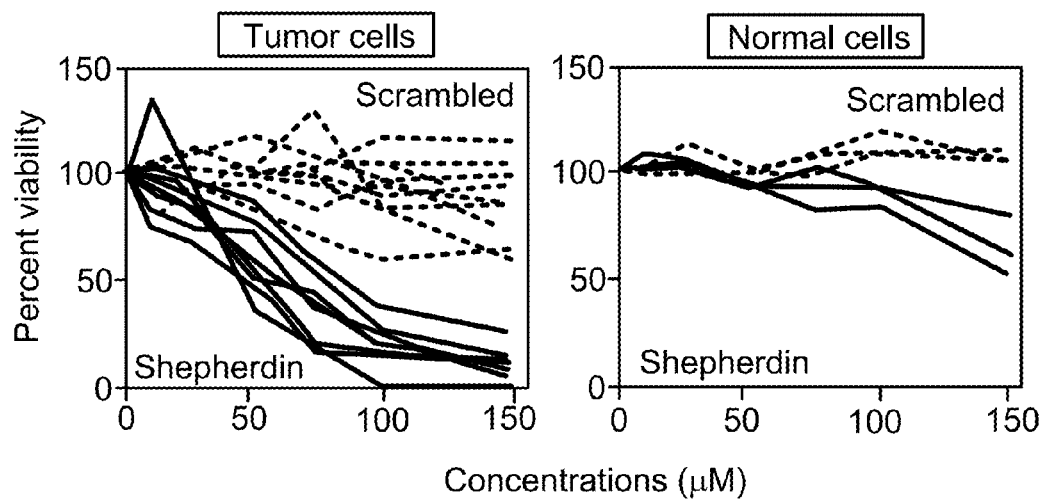
FIG. 5G consists of two line graphs showing percent viabilities, as determined by MTT (3-(4,5-dimethylthiazol-2-yl)-2,5-diphenyltetrazolium bromide) viability analysis, of tumor cells (left) and normal cells (right) incubated with increasing concentrations of Sheph-ANT (solid line) or increasing concentrations of Scram-ANT (broken line).
Figure 5H:
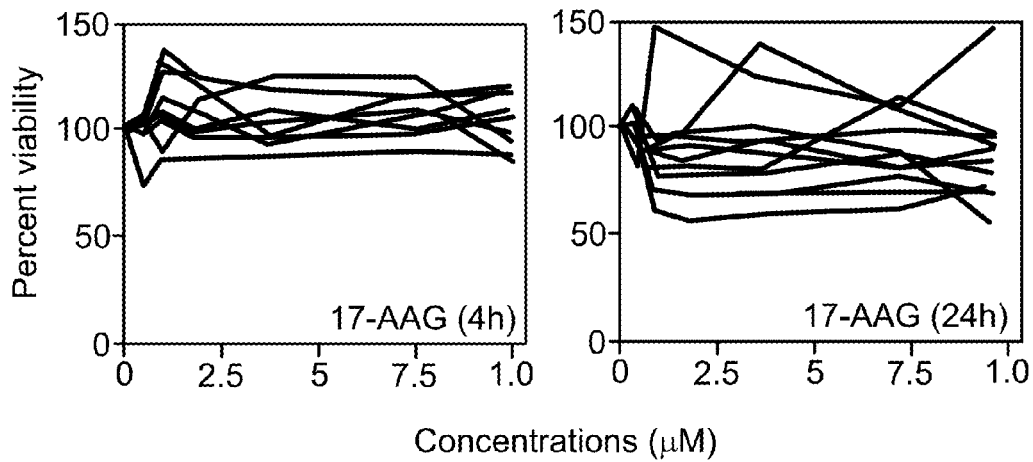
FIG. 5H consists of two line graphs showing percent viabilities, as determined by MTT, of tumor cells (left) and normal cells (right) incubated with increasing concentrations of 17-AAG for 4 hours (left) or 24 hours (right).

Within five minutes of addition, Sheph-ANT-induced loss of mitochondrial membrane potential in tumor cells (FIG. 5D), and discharge of mitochondrial cytochrome c in the cytosol (not shown). In contrast, a cell permeable scrambled peptidomimetic (Scram-ANT) was without effect (FIG. 5D). In parallel experiments, 17-AAG did not affect mitochondrial membrane potential in HeLa cells (FIG. 5D), and had no effect on cytochrome c release over a wide range of concentrations (FIG. 5E). When analyzed by time-lapse videomicroscopy, tumor cells exposed to Sheph-ANT, but not Scram-ANT, exhibited within minutes morphological features of apoptosis, including cell shrinkage, membrane blebbing, and fusion/fission of mitochondria around the perinuclear area (FIG. 5F). Accordingly, a 1 hour exposure to Sheph-ANT was sufficient to kill disparate tumor cell types in a concentration-dependent manner, whereas a cell-permeable scrambled peptidomimetic, Scram-ANT, was ineffective (FIG. 5G). Consistent with selectivity of action, comparable concentrations of Sheph-ANT did not affect the viability of various normal human fibroblast cell types (FIG. 5G). In contrast, 17-AAG had no effect on tumor cell viability within the same kinetics, and only a prolonged exposure to the drug resulted in partial cell killing, detectable 24 hours after treatment (FIG. 5H).

Example 5: An Hsp90-Regulated Chaperone Network in Mitochondria

Figure 6A:
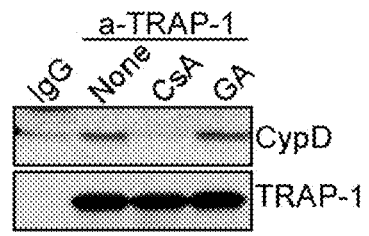
FIG. 6A is a set of two immunoblots of mitochondrial TRAP-1 and CypD immunoprecipitated using antibody to TRAP-1 or IgG (as control), from purified Raji mitochondrial extracts treated with cyclosporine A (CsA) or geldanamycin (GA). Mitochondrial extracts not treated with any drug (None) is a control.
Figure 6B:
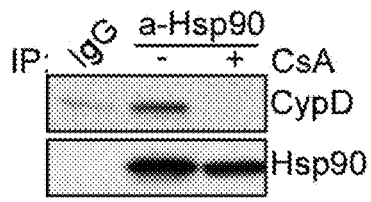
FIG. 6B is a set of two immunoblots of Hsp90 and CypD immunoprecipitated from Raji mitochondrial extracts treated with (+) or without (−) CsA using antibody to Hsp90 or IgG (as control).
Figure 6C:
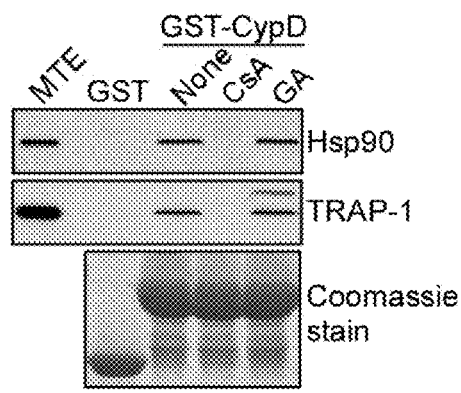
FIG. 6C is a set of three immunoblots; the upper and middle panels are immunoblots of Hsp90 and TRAP-1 captured from Raji mitochondrial extracts treated with CsA or GA or no drug (None) using GST (as control) or GST-CypD. The lower panel is the Coomassie stained gel corresponding to immunoblots in upper and middle panels.
Figure 10A:
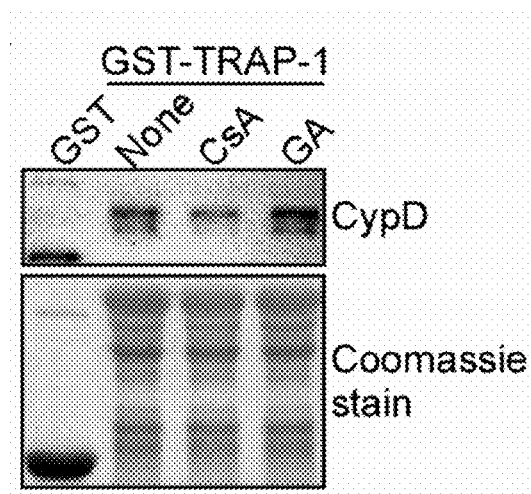
FIG. 10A is a set of two immunoblots. The top panel is a CypD immunoblot in which GST or GST-TRAP-1 was incubated with recombinant CypD with addition of CsA, GA, or no drug, showing that GST-TRAP1 CypD is pulled down by GST-TRAP-1 but not GST. The bottom panel of FIG. 10A is a Coomassie stain of the immunoblotted gel.
Figure 10B:
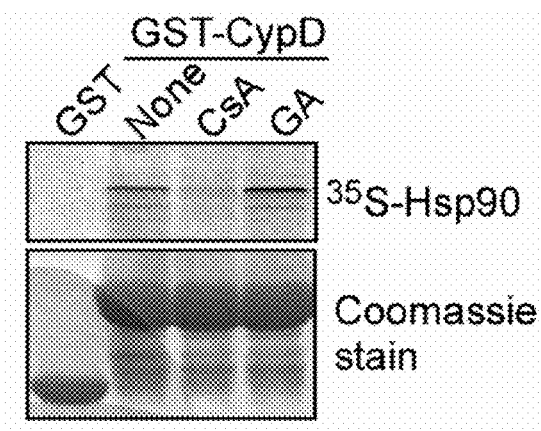
FIG. 10B is a set of two immunoblots. The top panel is an autoradiograph of a protein gel from electrophoresis of GST or GST-CypD pull-down of in vitro transcribed and translated $^{35}$S-labeled Hsp90.
Figure 10C:
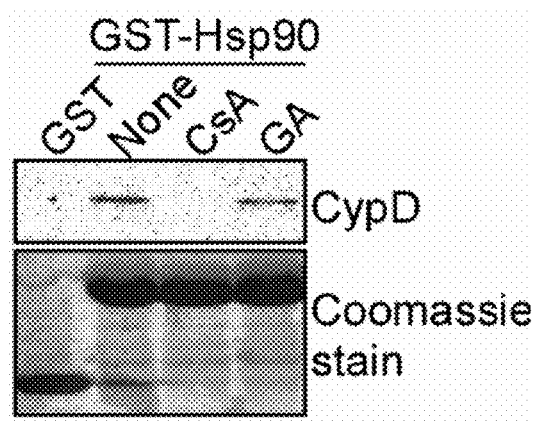
FIG. 10C is a set of two immunoblots. The top panel is an autoradiograph of a protein gel from electrophoresis of GST or GST-Hsp90 pull-down of in vitro transcribed and translated $^{35}$S-labeled CypD.

TRAP-1 immunoprecipitated from isolated Raji mitochondria was found in a complex with endogenous CypD (FIG. 6A). The CypD inhibitor, cyclosporine A (CsA), prevented the formation of a CypD-TRAP-1 complex, in vivo (FIG. 6A). Treatment with GA had no effect (FIG. 6A). Similar to TRAP-1, Hsp90 immunoprecipitated from isolated mitochondrial extracts associated with endogenous CypD, in vivo, and this interaction was also prevented by CsA (FIG. 6B). Hsp90 was not found in TRAP-1 immune complexes (not shown), suggesting the existence of independent TRAP-1- and Hsp90-complexes containing CypD in mitochondria. The interactions between Hsp90 chaperones and CypD were confirmed using a cell-free system. In pull down experiments, recombinant TRAP-1 or Hsp90 bound directly to recombinant CypD, and, vice versa, CypD directly associated with recombinant Hsp90 molecules, in a reaction also abolished by CsA, but not GA (FIG. 10). In contrast, GST did not associate with Hsp90 or TRAP-1, in vitro (FIG. 10). Incubation of GST-CypD with Raji mitochondrial extracts resulted in the isolation of both TRAP-1 and Hsp90, and these interactions were inhibited by CsA, but not GA (FIG. 6C).

Example 6: Molecular Requirements of Hsp90-Directed Mitochondrial Homeostasis

Figure 6D:
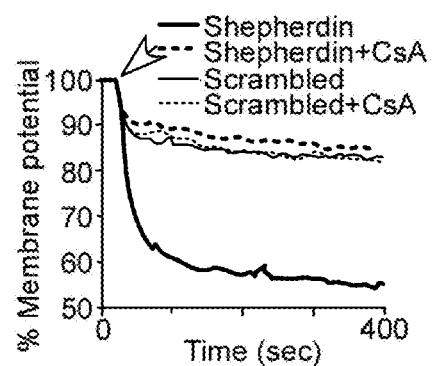
FIG. 6D is a line graph showing mitochondrial membrane potential over time following addition (at arrow) of Sheph-ANT or Scram-ANT in the presence (broken line) or absence (solid line) of CsA to TMRM-loaded mitochondria isolated from HeLa cells.
Figure 6E:
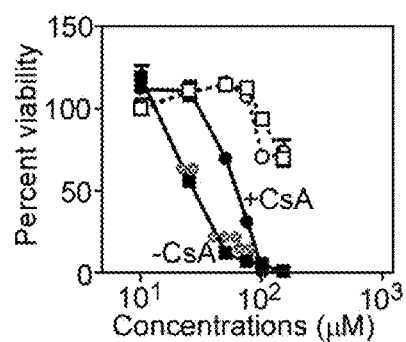
FIG. 6E is a line graph showing percent viability, as determined by MTT, of HeLa cells treated with increasing concentrations of Sheph-ANT (solid symbols) or Scram-ANT (open symbols) in the presence (circles) or absence (squares) of CsA.
Figure 6F:
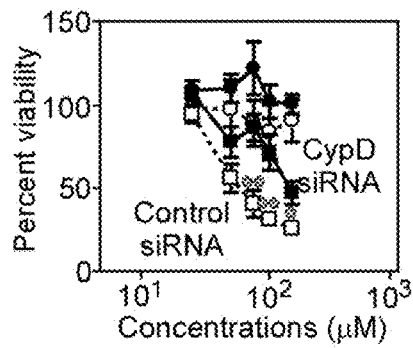
FIG. 6F is a line graph showing percent viability, as determined by MTT, of HeLa cells transfected with control siRNA (open symbols) or CypD-directed siRNA (solid symbols), treated with increasing concentrations of Sheph-ANT (squares) or Scram-ANT (circles).

Inhibition of CypD activity with CsA completely prevented membrane depolarization of tumor mitochondria by Sheph-ANT (FIG. 6D). Sheph-ANT had no effect on normal liver mitochondria, with or without CsA. CsA significantly inhibited Sheph-ANT-induced cell death, preserving a 70% cell viability at concentrations of Sheph-ANT (50 μM) that produce complete cell killing in cultures that are not treated with CsA (FIG. 6E). To confirm that the protective effect of CsA was specific, we next acutely ablated its target, CypD, by small interfering RNA (siRNA), and quantified tumor cell killing mediated by Shepherdin. siRNA ablation of CypD also prevented Sheph-ANT-induced tumor cell killing, restoring a 60-70% cell viability over a broad range of effective concentrations (50-100 μM) of Sheph-ANT (FIG. 6F). In contrast, a scrambled peptidomimetic, Scram-ANT, had no effect in the presence or absence of CsA (FIG. 6E), or after transfection of non-targeted or CypD-directed siRNA (FIG. 6F).

Figure 6G:
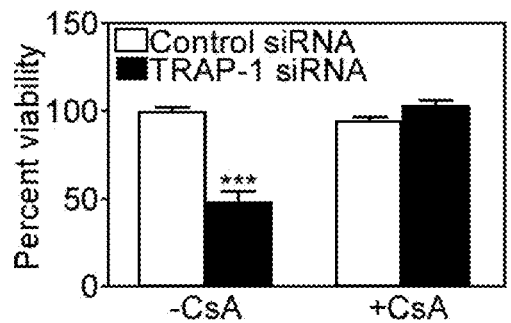
FIG. 6G is a bar graph showing percent viability, as determined by MTT, of HeLa cells transfected with control siRNA or TRAP-1-directed siRNA in the presence or absence of CsA.
Figure 6H:
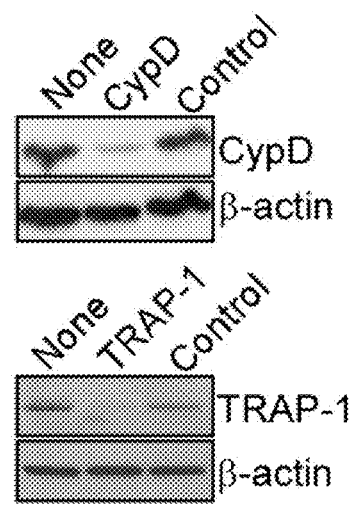
FIG. 6H is a set of two pairs of immunoblots of extracts of HeLa cells transfected with control siRNA, or CypD-directed siRNA (top set of two panels) or TRAP-1-directed siRNA (bottom set of two panels). Non-transfected cultures (None) are controls. β-actin immunoblots are controls.
Figure 6I:
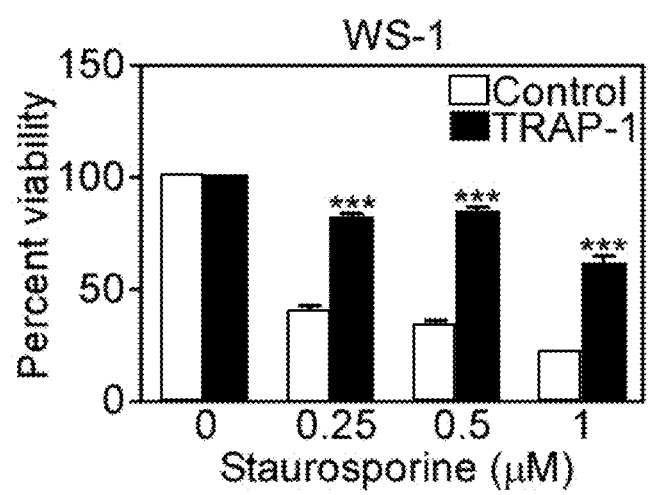
FIG. 6I is a bar graph of percent viability, as determined by MTT, of normal WS-1 fibroblasts transfected with pcDNA3 (as a control) or TRAP-1 cDNA, treated with increasing concentrations of staurosporine.
Figure 11:
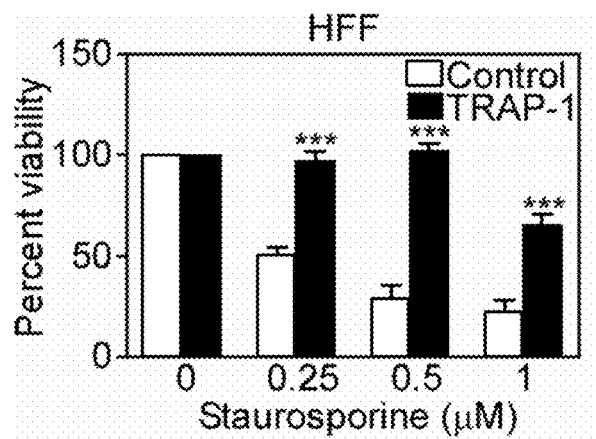
FIG. 11 is a bar graph showing percent viability, as determined by MTT, of normal HFF human fibroblasts transfected with pcDNA3 (as a control) or TRAP-1 cDNA and treated with various concentrations of staurosporine.

In order to determine if mitochondrial Hsp90, TRAP-1, or both molecules antagonize the function of CypD in permeability transition, the following experiments were performed. TRAP-1 expression, which is solely present in mitochondria, was ablated by siRNA and the effects on cell viability were determined. TRAP-1 silencing reduced HeLa cell viability by approximately 50%, as compared with non-targeted siRNA (FIG. 6G). Preincubation with CsA completely inhibited cell death induced by TRAP-1 silencing (FIG. 6G), suggesting that Hsp90 chaperone antagonism of CypD in the mitochondria is required for cancer cell viability. In control experiments, siRNA directed to TRAP-1 or CypD reduced the expression of these two proteins in HeLa cells, whereas non-targeted siRNA had no effect (FIG. 6H). To further examine whether mitochondrial Hsp90 molecules confer active protection against apoptosis, TRAP-1 was transfected into normal human fibroblasts, which express very low levels of this protein (FIG. 2F, G). The transfected human fibroblasts were subsequently tested for resistance to staurosporine-induced apoptosis. Expression of recombinant TRAP-1 in WS-1 (FIG. 6I) or HFF (FIG. 11) normal human fibroblasts strongly counteracted apoptosis over a broad range of staurosporine concentrations, as compared with controls.

Example 7: Design and Chemical Synthesis of Mitochondria-Directed GA

Figure 12A:
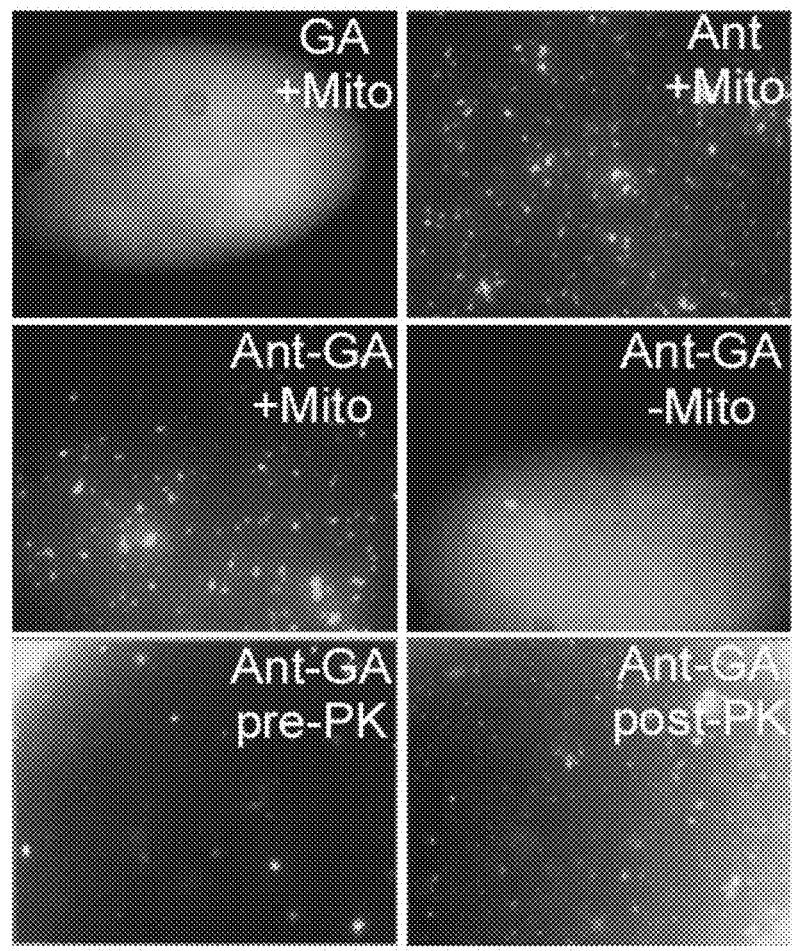
FIG. 12A is a set of six panels of images; the top and middle rows are fluorescent microscopy images of FITC-GA (top, left panel), FITC-ANT (top, right panel), or FITC-ANT-GA (middle, left panel) incubated with purified Raji cell mitochondria or FITC-ANT-GA (middle, right panel) incubated without purified Raji cell mitochondria. The panels in the bottom row are FITC-ANT-GA incubated with purified Raji cell mitochondria before (bottom, left panel) and after (bottom, right panel) PK treatment.
Figure 12B:
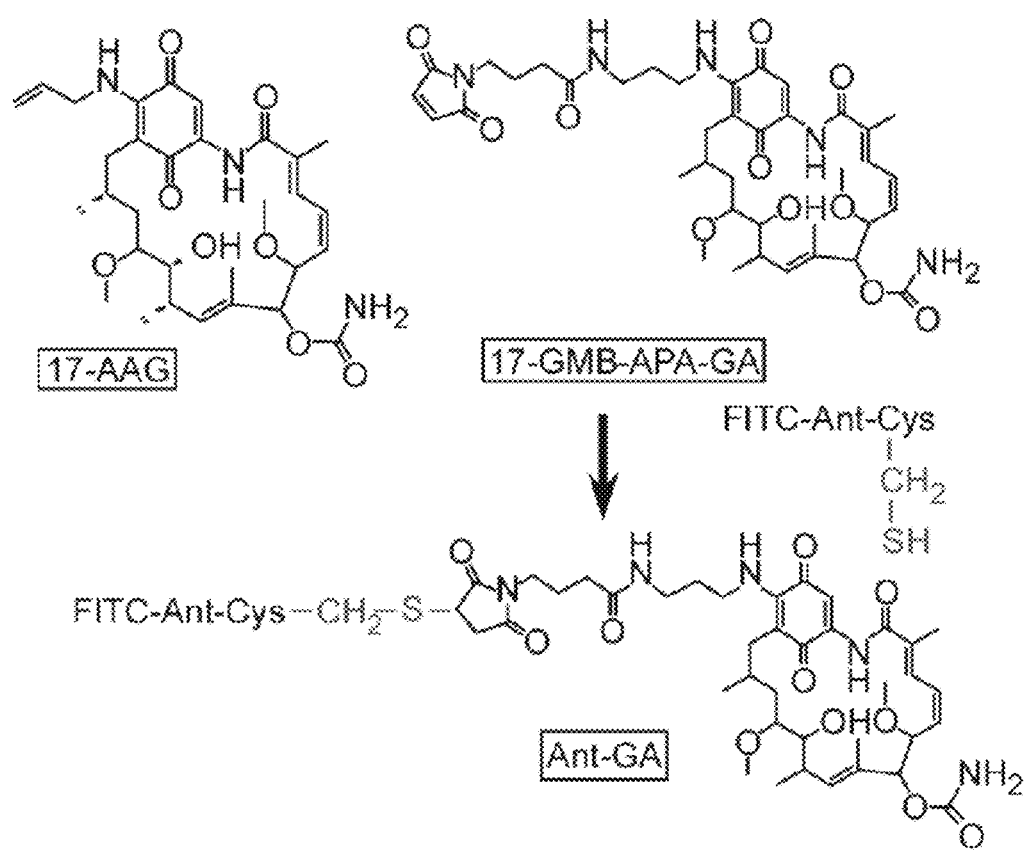
FIG. 12B is a diagram showing one scheme for the coupling of 17-AAG or 17-GMB-APA-GA to ANT by a thioether linkage to produce ANT-GA.

Although Sheph-ANT induced permeability transition in isolated mitochondria and live cells, and triggered selective tumor cell death, a well-characterized Hsp90 antagonist, 17-AAG (Neckers and Ivy, Curr. Opin. Oncol., 15:419-424, (2003)), had no effect on mitochondrial integrity (FIG. 3K, L), and exhibited modest anticancer activity (FIG. 5H). In order to determine if the lack of effect of 17-AAG was due to a failure of 17-AAG to accumulate inside mitochondria, localization studies were performed. Fluorescein-conjugated GA failed to accumulate inside isolated tumor cell mitochondria (FIG. 12A). A variant of 17-AAG, 17-(3-(4-Maleimidobutyrcarboxamido)propylamino)-demethoxygeldanamycin (17-GMB-APA-GA) (FIG. 12B, C) was covalently coupled by a thioether linkage to the Antennapedia cell-penetrating peptide (ANT). When conjugated with FITC, this new compound, termed ANT-GA (FIG. 12C), readily accumulated inside isolated tumor mitochondria, whereas no fluorescence signal was detected in the absence of mitochondria (FIG. 12A). Pretreatment of ANT-GA with proteinase K abolished intramitochondrial accumulation, whereas addition of proteinase K after ANT-GA incubation with mitochondria was ineffective (FIG. 12A), indicating that the compound was protected from proteolysis. Overnight incubation of HeLa cells with a suboptimal concentration of ANT-GA resulted in the degradation of Akt, an Hsp90 client protein (FIG. 12D), confirming its ability to inhibit Hsp90 ATPase activity, indistinguishably from the uncoupled mixture of ANT and GA (GA/ANT).

Example 8: Induction of Mitochondrial Permeability Transition and Selective Tumor Cell Death by Mitochondria-Directed GA (ANT-GA)

Figure 7A:
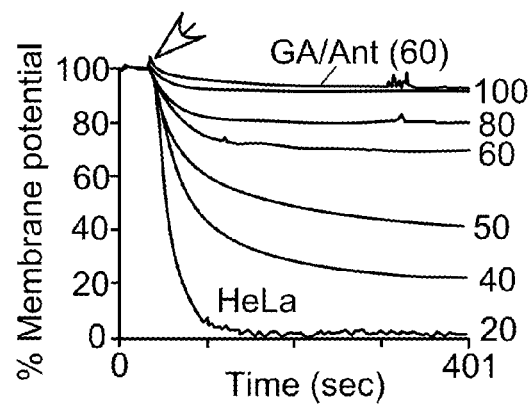
FIG. 7A is a line graph showing mitochondrial membrane potential over time following addition (at arrow) of ANT-GA or the uncoupled mixture GA/ANT, for varying concentrations (μg) of TMRM-loaded mitochondria isolated from HeLa cells. The uncoupled mixture GA/ANT, incubated with 60 μg of isolated mitochondria, is a control.
Figure 7B:
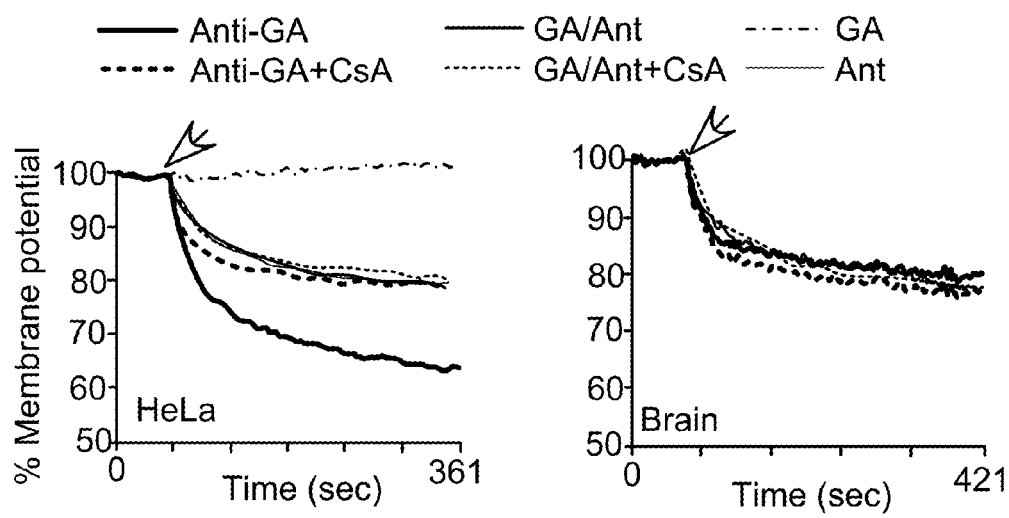
FIG. 7B consists of two line graphs showing mitochondrial membrane potential over time following addition (at arrow) of ANT-GA or the uncoupled mixture GA/ANT with or without CsA of TMRM-loaded mitochondria isolated from HeLa cells (left) or mouse brain (right).
Figure 7F:
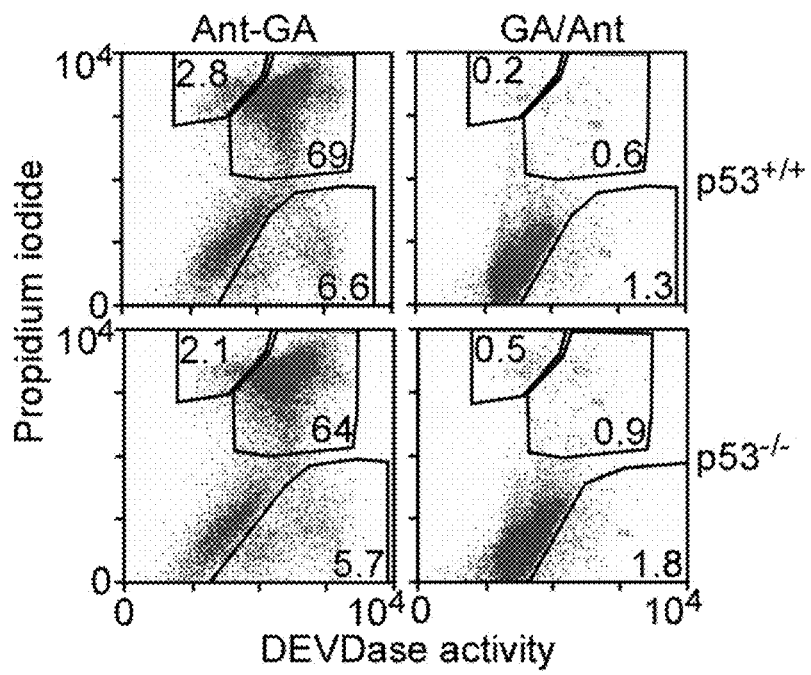
FIG. 7F is four scatter plots, with propidium iodide staining intensity on the y-axis and DEVDase activity on the x-axis, of flow cytometry analysis of p53$^{+/+}$ (two plots at top) and p53$^{-/-}$ (two plots at bottom) HCT116 cells treated with ANT-GA (two plots at left) or the GA/ANT (two plots at right). The percentage of cells in each quadrant is indicated.

Incubation of purified HeLa cell mitochondria with ANT-GA resulted in sudden loss of mitochondrial membrane potential (FIG. 7A). This response was progressively attenuated at increasing mitochondria concentrations, indicating that compound accumulation inside mitochondria was required for activity (FIG. 7A). CsA completely reversed ANT-GA-induced membrane depolarization of tumor mitochondria (FIG. 7B), reinforcing a role of CypD in this pathway. In addition, ANT-GA was selective for tumor cells, and triggered concentration-dependent release of cytochrome c in isolated tumor mitochondria (FIG. 7C, top), but did not affect the membrane potential of normal brain mitochondria, with or without CsA (FIG. 7B), or the cytochrome c content of normal liver mitochondria (FIG. 7C, bottom). In control experiments, the uncoupled mixture of GA/ANT, or GA alone, did not significantly affect normal or tumor mitochondria membrane potential (FIG. 7B), and had no effect on cytochrome c release (FIG. 7C). When added to tumor cells, ANT-GA, but not GA alone or the uncoupled ANT/GA mixture, produced rapid (~2 hours), and concentration-dependent cell killing (FIG. 7D), whereas none of the compounds affected the viability of various normal human fibroblast cell types (FIG. 7E). Finally, tumor cell killing induced by ANT-GA had the hallmarks of apoptosis with increased caspase activity, as determined by DEVDase hydrolysis, and was unaffected by the presence or absence of p53 (FIG. 7F). In contrast, the uncoupled mixture GA/ANT did not induce apoptosis in $p53^{+/+}$ or $p53^{-/-}$ cells (FIG. 7F).

Example 9: Selective Hsp60 Cytoprotection in Tumors

Figure 13B:
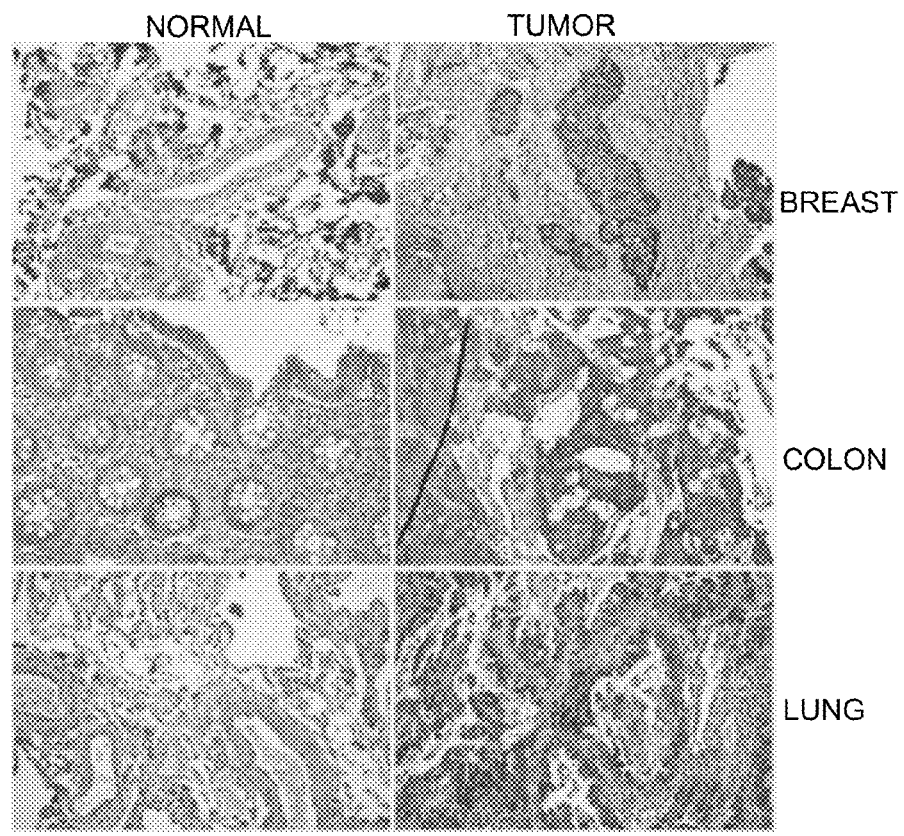
FIG. 13B is a set of six photomicrographs showing primary human tissue specimens of adenocarcinoma of breast, colon, or lung (tumor), or matched normal tissues (normal) stained with an antibody to Hsp60, and analyzed by immunohistochemistry. Magnification, ×200.

To determine whether Hsp60 cytoprotection was preferentially exploited in cancer, its expression and function in normal versus tumor cell types was examined. Mitochondrial and cytosolic fractions were extracted from tumor cells (6-7×107), essentially as described (Dohi et al., J Clin Invest 2004; 114:1117-27). Hsp60 was abundantly present in mitochondrial and extramitochondrial (Soltys and Gupta, Int Rev Cytol 2000; 194:133-96), i.e. cytosolic, fractions of Breast adenocarcinoma MCF-7 and colon adenocarcinoma HCT116 cells (FIG. 13A, top panel). In contrast, primary WS-1 and HFF human fibroblasts exhibited considerably reduced levels of Hsp60 in both subcellular compartments (FIG. 13A, bottom panel). By immunohistochemistry, Hsp60 was undetectable, or expressed at very low levels in normal epithelium of breast, colon, and lung, in vivo (FIG. 13B). In contrast, Hsp60 was abundantly expressed in the tumor cell population of adenocarcinoma of breast, colon, and lung (FIG. 13B); the primary tissue specimens of breast, lung and colon adenocarcinoma, and normal matched tissues were obtained anonymously from the UMass Memorial Cancer Center Tissue Bank. Tissue sections were processed for immunohistochemistry using IgG or an antibody to Hsp60 (1:1000), as described (Dohi et al., J Clin Invest 2004; 114:1117-27). In control experiments, IgG did not stain normal or tumor epithelia.

To determine whether Hsp60 cytoprotection was selectively operative in tumor cells, Hsp60 expression was targeted in normal and tumor cell types, and cell viability analyzed. Gene silencing by small interfering RNA (siRNA) was carried out by transfection of non-targeted (VIII) or Hsp60-directed double stranded (ds) RNA oligonucleotides using oligofectamine (3 µl/well), as described (Beltrami et al., J Biol Chem 2004; 279:2077-84). Alternatively, cells were transfected with control or SMART pool siRNA oligonucleotides to Hsp60 (Dharmacon), by oligofectamine. For double transfection experiments, cells were loaded twice with control or Hsp60-directed siRNA at 48 hour intervals between each transfection.

Figure 13C:
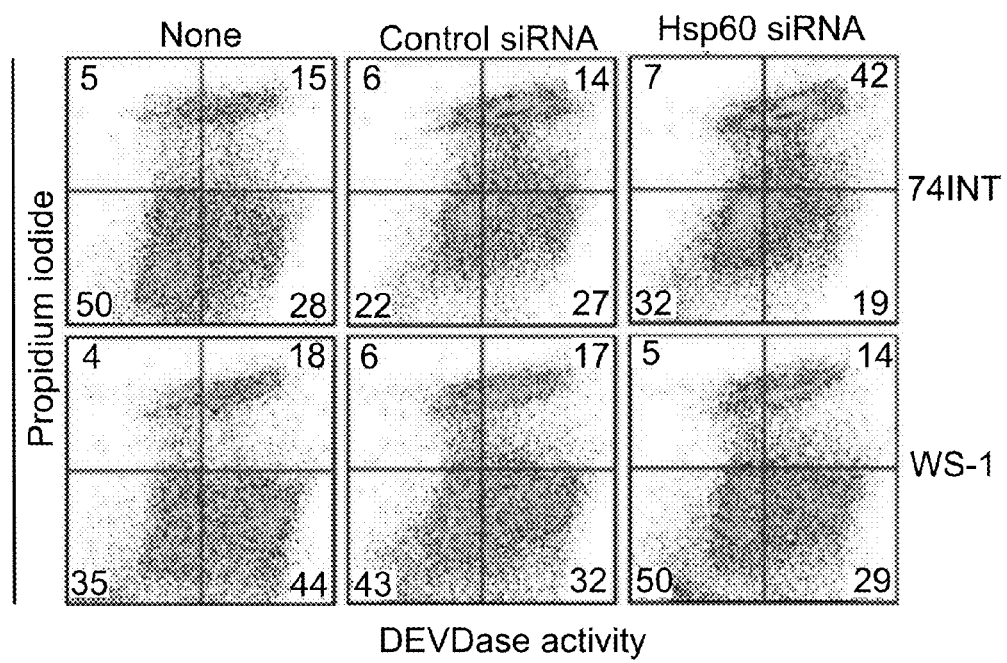
FIG. 13C is a set of six plots showing the results of experiments in which 74INT normal epithelial cells or primary WS-1 normal fibroblasts were transfected with non-targeted or Hsp60-directed siRNA, and analyzed by DEVDase activity and propidium iodide staining by multiparametric flow cytometry. The percentage of cells in each quadrant is indicated. None, non transfected cells.

Transfection of 741NT normal human epithelial cells or WS-1 primary human fibroblasts with Hsp60-directed siRNA resulted in suppression of Hsp60 expression, whereas a non-targeted siRNA was without effect. At variance with the results obtained with tumor cell lines, acute siRNA ablation of Hsp60 in normal cells did not result in loss of cell viability, or increased caspase activity, as compared with control cultures transfected with non-targeted siRNA (FIG. 13C).

Thus, Hsp60 (which binds to survivin, data not shown) contributes to a broad anti-apoptotic program that is differentially exploited in tumors, in vivo, and can therefore be targeted for preferentially killing tumor cells while sparing normal cells.

Example 10: Gamitrinibs Efficiently Disrupt Mitochondrial Integrity

Figure 15A:
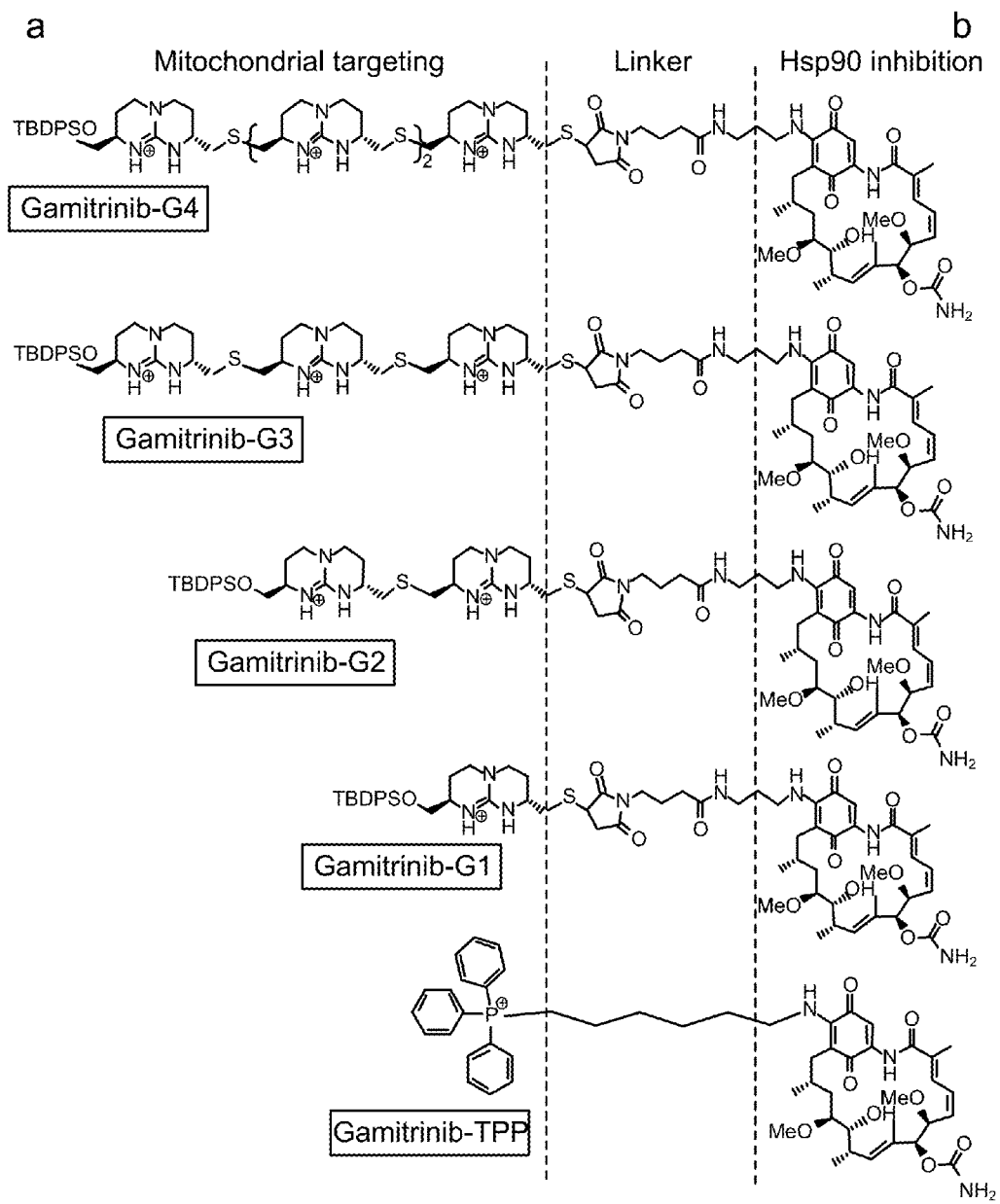
FIG. 15A is a diagram showing the combinatorial modular structure of Gamitrinibs in which TBDPS indicates tert-butyldiphenylsilyl.

Gamitrinibs (GA mitochondrial matrix inhibitors) are the first class of small molecule antagonists of Hsp90 chaperones compartmentalized in mitochondria. The structure of Gamitrinibs is combinatorial, and contains a benzoquinone ansamycin backbone derived from the Hsp90 inhibitor, 17-allylamino geldanamycin (17-AAG) (Isaacs et al., Cancer Cell, 3:213-217 (2003)), a linker region on the C17 position, and a mitochondrial targeting moiety, either provided by one to four tandem repeats of cyclic guanidinium (Fernandez-Carneado et al., J Am Chem Soc, 127:869-874 (2005)). (Gamitrinib G1-G4), or triphenylphosphonium (Armstrong, Br J Pharmacol, 151:1154-1165 (2007)) (Gamitrinib-TPP) (FIG. 15A). The 17-AAG portion of Gamitrinibs is predicted to make contacts with the Hsp90 ATPase pocket, whereas the guanidinium module is excluded from the binding interface, pointing outside of the ATPase pocket towards the solvent. In the predicted docking structure, the binding arrangement of Gamitrinibs to Hsp90 closely follows that of Geldanamycin (GA) (Stebbins et al., Cell, 89:239-250 (1997)), with root mean square deviation of heavy atoms of the 17-AAG region being 0.5 Å.

Figure 15B:
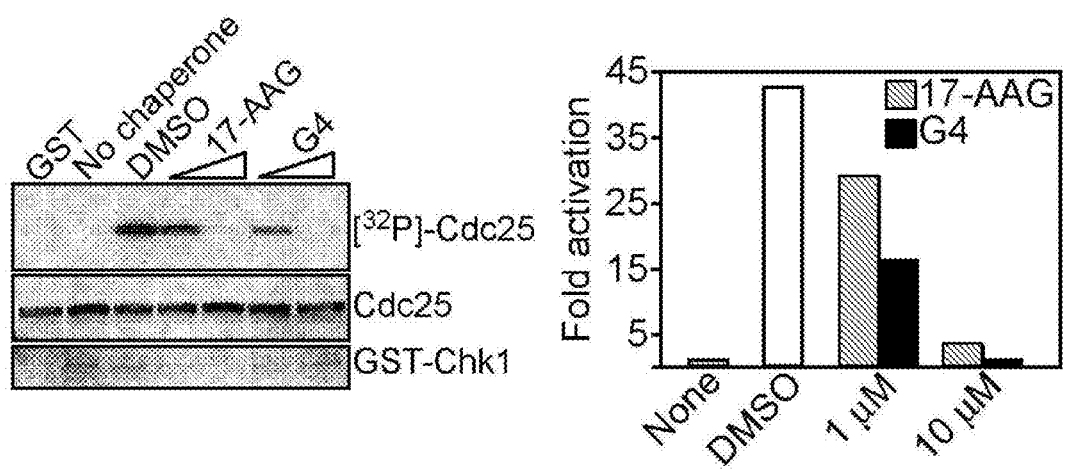
FIG. 15B left panel at top is an autoradiogram showing chaperone activity as Chk1-dependent phosphorylation of Cdc25 in cells treated with 17-AAG or Gamitrinib-G4 (indicated as "G4") (1-10 μM) with loading controls shown at middle (Cdc25) and bottom (GST-Chk1). The right panel is a bar graph showing densitometric quantification of the bands shown in the left panel and is representative of two experiments.
Figure 15C:
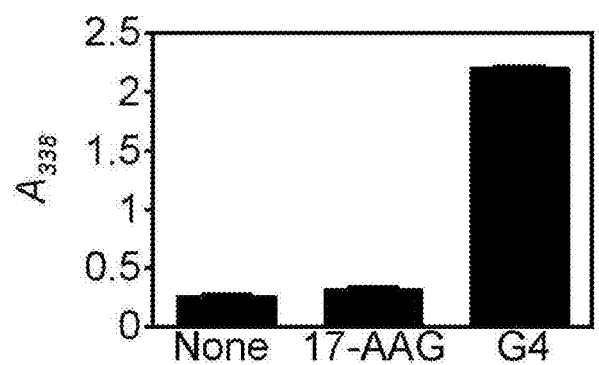
FIG. 15C is a bar graph quantifying mitochondrial accumulation of 17-AAG or Gamitrinib-G4 (indicated as "G4") in which "None" indicates vehicle control. Mean±SEM (n=3).

Gamitrinib-G4 effectively competed with GA affinity beads for binding to Hsp90 in a tumor cell lysate and inhibited Hsp90 chaperone activity (FIG. 15B) in a purified client protein reconstitution assay (Arlander et al., J. Biol. Chem., 281:2989-2998 (2006)). Gamitrinib-G4 selectively accumulated in isolated tumor mitochondria, whereas non-targeted 17-AAG did not penetrate or accumulate in mitochondria (FIG. 15C)(Kang et al., Cell, 131:257-270 (2007)).

Figure 16C:
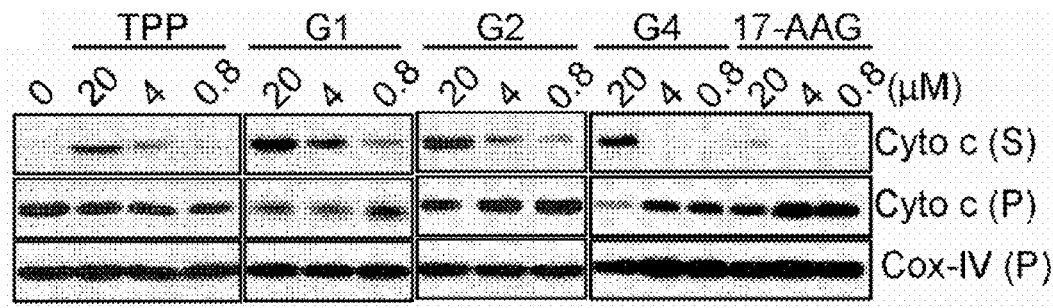
FIG. 16C is a panel of immunoblots showing cytochrome c release in supernatants (S) or pellets (P) showing Cox-IV as a mitochondrial marker in tumor mitochondria treated with Gamitrinib-G1 ("G1"), Gamitrinib-G2 ("G2"), Gamitrinib-G4 ("G4"), or 17-AAG (20 minutes).

Gamitrinibs disrupted mitochondrial integrity. When added to isolated tumor mitochondria, Gamitrinibs caused sudden loss of inner membrane potential, all with comparable efficiency (FIG. 16A). In contrast, non-targeted Hsp90 antagonists, GA, 17-AAG or 17-(dimethylaminoethylamino)-17-demethoxygeldanamycin (DMAG) did not affect mitochondrial membrane potential (FIG. 16A). Gamitrinibs (G4 or TPP) promptly depolarized tumor mitochondria, and this reaction was inhibited by cyclosporine A (CsA), an inhibitor of CypD (FIG. 16B). In contrast, 17-AAG or GA mixed with the isolated mitochondrial-penetrating moieties, e.g., TG-OH or TPP-OH, had no effect on mitochondrial membrane potential, with or without CsA (FIG. 16B). All Gamitrinibs also induced rapid (20 minutes) discharge of mitochondrial cytochrome c, whereas 17-AAG was ineffective (FIG. 16C).

Figure 16D:
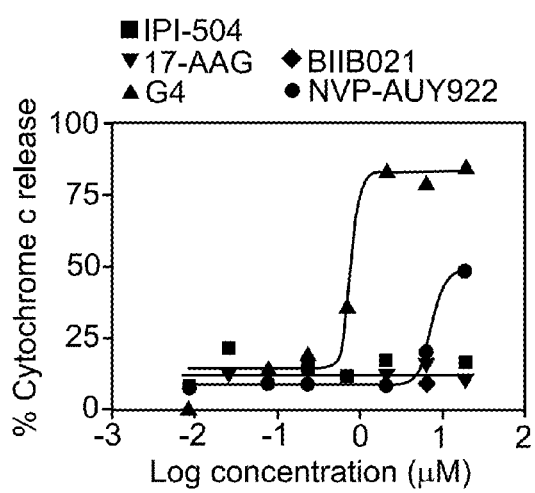
FIG. 16D is a line graph showing percent cytochrome c release over time from mitochondria incubated with IPI-504, BIIB021, NVP-AUY922, 17-AAG, or Gamitrinib-G4 ("G4") for 3 hours. Data are representative of two independent experiments.
Figure 19:
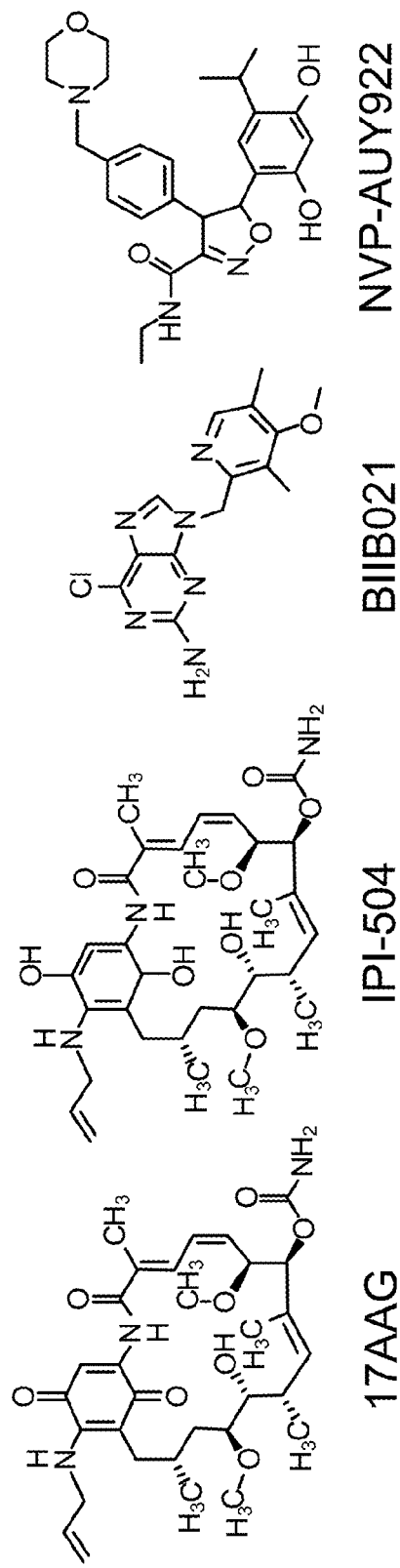
FIG. 19 is a schematic diagram of chemical structures of GA (17-AAG), IPI-504, and non-GA based (BIIB021 and NVP-AUY922) Hsp90 inhibitors used in these studies.

Several recently developed purine- and isoxazole resorcinol-based Hsp90 antagonists (FIG. 19) were tested for changes in mitochondrial integrity. Gamitrinib-G4 induced sudden and complete discharge of cytochrome c from mitochondria (FIG. 16D). In contrast, 17-AAG, hydroquinone derivative of 17-AAG (IPI-504), purine analog (BIIB021), or isoxazole (NVP-AUY922) Hsp90 inhibitors had no effect on cytochrome c release (FIG. 16D).

Figure 17A:
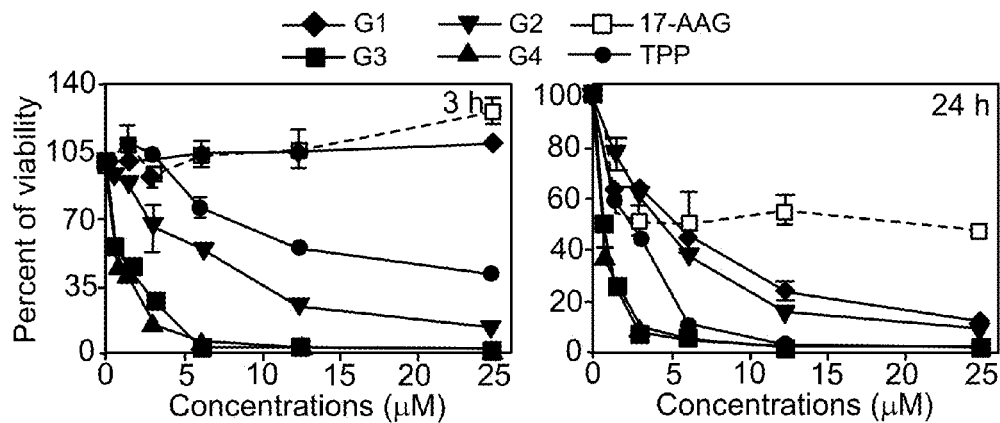
FIG. 17A consists of two line graphs showing percent viability of H460 cells, as analyzed by MTT, treated with Gamitrinib-G1 ("G1"), Gamitrinib-G2 ("G2"), Gamitrinib-G3 ("G3"), Gamitrinib-G4 ("G4"), Gamitrinib-TPP ("TPP"), or 17-AAG at different concentrations after 3 hours of treatment in the line graph to the left and after 24 hours of treatment in the line graph to the right. Mean±SD (n=2).

Mitochondrial depolarization and release of cytochrome c are hallmarks of mitochondrial permeability transition (Green et al., Science 305:626-629 (2004)), which typically results in cell death. Consistent with this prediction, a 3 hour exposure of lung adenocarcinoma H460 cells to Gamitrinib-G3 or -G4 was sufficient to produce a concentration-dependent ($IC_{50}$~0.5 μM) and complete loss of cell viability (FIG. 17A, left). Within this time frame, Gamitrinib-G1 or 17-AAG had no effect, and Gamitrinib-G2 or Gamitrinib-TPP had intermediate activity, reflecting different efficiencies of intracellular accumulation (FIG. 17A, left). By 24 hours, all Gamitrinibs had comparably killed the entire tumor cell population, whereas 17-AAG resulted in a partial reduction in cell viability or cell proliferation (FIG. 17A, right).

Figure 17B:
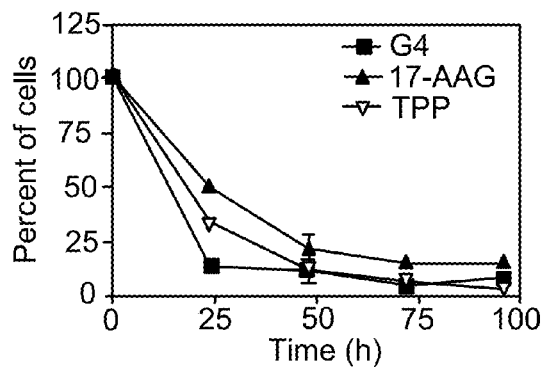
FIG. 17B is a line graph showing percent viability over time of SKBr3 cells treated with Gamitrinib-G4 ("G4"), Gamitrinib-TPP ("TPP"), or 17-AAG (at a concentration of 10 µM) and analyzed by MTT.
Figure 17C:
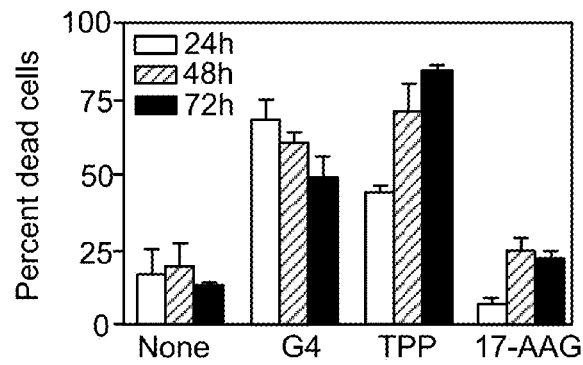
FIG. 17C is a bar graph showing the percentage of dead cells as analyzed by Trypam blue staining in SKBr3 cells treated with 10 µM of Gamitrinib-G4 ("G4"), Gamitrinib-TPP ("TPP"), or 17-AAG at the indicated time intervals. Mean±SEM (n=3).
Figure 17D:
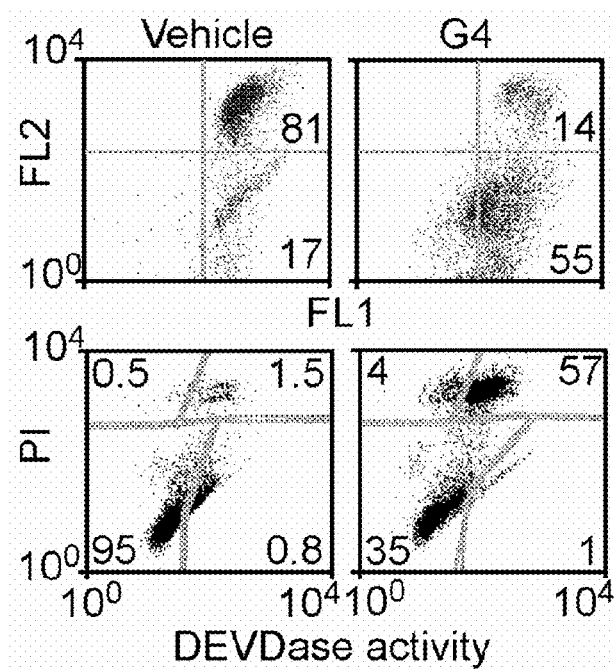
FIG. 17D consists of four scatter plots. H460 cells were treated with Gamitrinib-G4 ("G4") or vehicle for four hours and were labeled with JC-1, and analyzed (by multiparametric flow cytometry) for loss of mitochondrial membrane potential by changes in FL2/FL1 fluorescence ratio as shown in the scatter plots at top, or DEVDase (caspase) activity as shown in the scatter plots at bottom. The percentage of cells in each quadrant is indicated and PI is used to indicate propidium iodide.
Figure 17E:
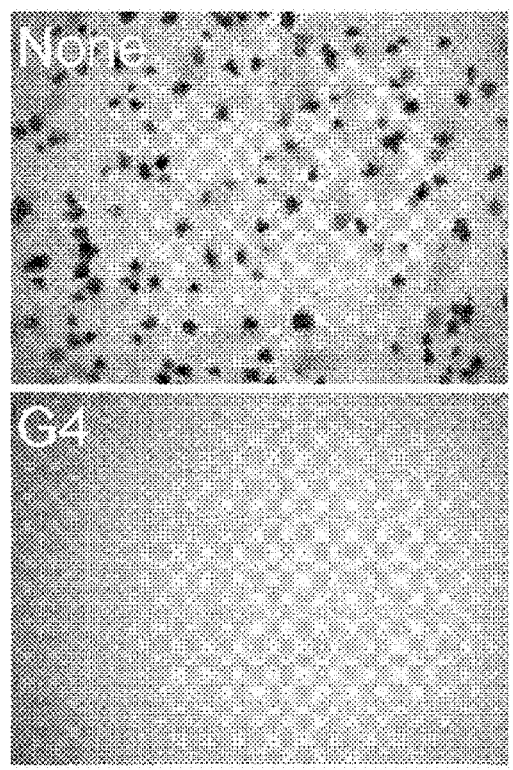
FIG. 17E are two pictures of colony formation in soft agar showing colony formation after two weeks using H460 cells treated with vehicle (None) for 4 hours in the top picture and colony formation after two weeks using H460 cells treated with Gamitrinib-G4 ("G4") at 50 µM for 4 hours in the bottom picture. Magnification, ×200.
Figure 17F:
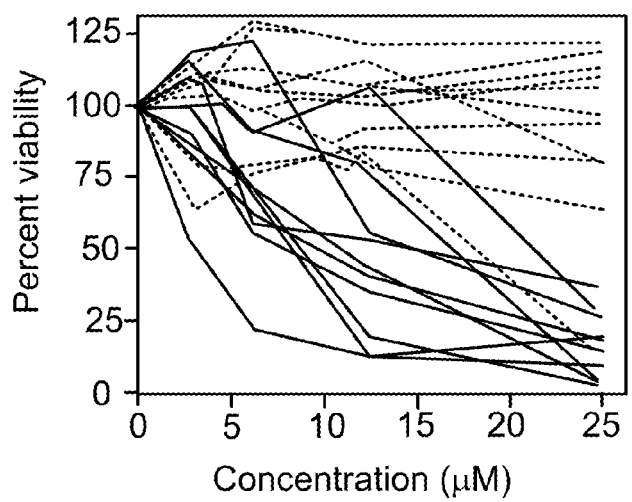
FIG. 17F is a line graph showing percent viability as a function of concentration Gamitrinib-G4 (solid lines) or 17-AAG mixed with TG-OH (dashed lines) in tumor cell lines (K562, black; MDA-MB-231, light orange; U87MG, red; MCF-7, pink; H1975, light brown; DU145, orange; H460, blue; HCT116, purple; HL-60, violet; Raji, dark pink; THP-1, green) as analyzed by MTT. Data are representative of two experiments.
Figure 17G:
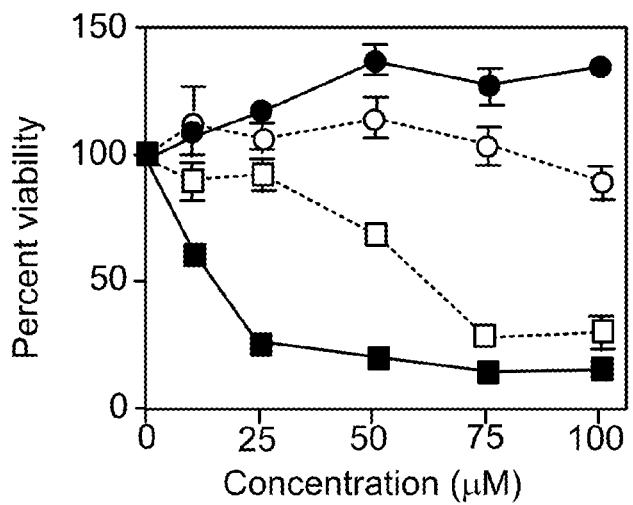
FIG. 17G is a line graph showing percent viability as a function of concentration 17-AAG (circles) or Gamitrinib-G4 (squares) in H460 cells transfected with control (closed symbols) or CypD (open symbols) siRNA as analyzed by MTT. Mean±SEM (n=3).

Current Hsp90 inhibitors predominantly cause cell cycle arrest in most tumor cell types, followed by a variable degree of apoptosis by 48-72 hours. To look for potential mechanistic differences in anticancer activity of Gamitrinibs compared to non-mitochondrially targeted Hsp90 inhibitors, breast adenocarcinoma SKBr3 cells (a model cell type that is highly sensitive to Hsp90 inhibition) was used. Treatment of SKBr3 cells with Gamitrinibs (G4 or TPP) or 17-AAG comparably reduced metabolic activity, by 48 hours and throughout a 96-hours interval (FIG. 17B). However, most SKBr3 cells treated with 17-AAG were still alive after 72 hours, whereas Gamitrinibs were cytotoxic, and caused nearly complete tumor cell killing by 24 hours (FIG. 17C). This cell death response was characterized by loss of mitochondrial inner membrane potential and caspase activity, indicative of mitochondrial apoptosis (FIG. 17D). Consistent with their cytotoxic properties, Gamitrinibs (G4) suppressed anchorage-independent tumor growth in soft agar (FIG. 17E) and had cytotoxic effect on a panel of heterogeneous tumor cell types (including, for example, human tumor cell types, chronic myelogenoeous leukemia cells, B lymphoblastoid leukemia cells, breast adenocarcinoma cells, lung adenocarcinoma cells, prostate adenocarcinoma cells, gliobastoma cells, colon adenocarcinoma cells, and cervical carcinoma cells). The cytotoxic effect of Gamitrinibs was independent of p53 status and expression of survival factors, e.g. Bcl-2 (FIG. 17F). Acute silencing of CypD (Green et al Science, 305:626-629 (2004)) by siRNA partially attenuated tumor cell killing mediated by Gamitrinib (FIG. 17G), confirming a role of a permeability transition pore in this pathway.

Figure 17H:
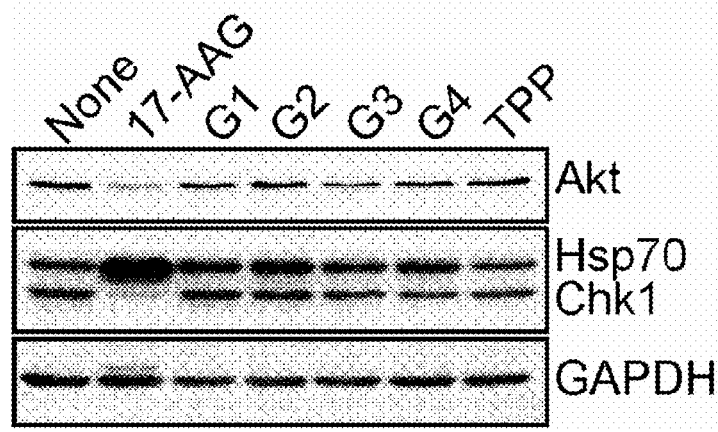
FIG. 17H is a series of immunoblots showing Akt, Hsp70, Chk1, and GAPDH protein levels in HeLa cells treated with Gamitrinib-G1 ("G1"), Gamitrinib-G2 ("G2"), Gamitrinib-G3 ("G3"), Gamitrinib-G4 ("G4"), Gamitrinib-TPP ("TPP"), or 17-AAG (at a concentration of 5 µM for 24 hours).

In order to determine if Gamitrinibs are specific for the mitochondrial pool of Hsp90 chaperones, cervical carcinoma HeLa cells were treated with 17-AAG, resulting in destabilization of client proteins, Chk1 and Akt (Isaacs et al., Cancer Cell, 3:213-217 (2003)), and increased expression of the chaperone Hsp70 (Beere et al., Nat Cell Biol, 2:469-475 (2000)). Decreased levels of Chk1 and Akt and increased levels of Hsp70 are consistent with inhibition of cytosolic Hsp90 (FIG. 17H). In contrast, Gamitrinibs had undetectable effect on levels of Chk1, Akt, and Hsp70 suggesting that it has minimal effect on cytosolic Hsp90 (FIG. 17H).

Example 11: Gamitrinibs are Effective in Xenograft Tumor Models

The effectiveness and toxicity of gamitrinibs was evaluated in xenograft tumor models.

To create the models used in this example, HL60 ($10 \times 10^6$) or H460 ($4 \times 10^6$) cells suspended in sterile PBS (200 μl) were injected subcutaneously into both flanks of 10 week-old CB17 SCID/beige (Taconic Farms) immunocompromised female mice. Alternatively, MDA-MB-231 cells ($5 \times 10^6$) suspended in 200 μl of 50% Matrigel (BD Biosciences) were used for subcutaneous injection in CB17 SCID/beige mice. When superficial tumors reached volumes of 100-150 mm³, animals were randomized in two groups (2 tumors/mouse, 3 animals/group), and treated with vehicle (DMSO) or Gamitrinib dissolved in 20% Cremophor EL (Sigma) in PBS by intraperitoneal (i.p.) injection. Gamitrinib-G4 was used as sterile i.p. injections with the following schedules: HL60 xenografts, 2 mg/Kg twice daily; H460 xenografts, 2 mg/Kg twice daily for d 0, 2.5 mg/kg twice daily for d 1, 3.0 mg/kg twice daily for the duration of treatment; MDA-MB-231 xenografts, 2 mg/Kg twice daily for d 0-2, 2.5 mg/Kg twice daily for d 3-5, and 3 mg/Kg twice daily throughout the rest of the treatment. 17-AAG was dissolved in 20% Cremophor EL and used as systemic i.p. injections with the same dose-escalating regimen as Gamitrinib-G4 in H460 xenograft studies. Gamitrinib-G1 was used with following schedules: 30 mg/Kg daily (d 0-2), and 50 mg/Kg daily for the rest of treatment. Gamitrinib-TPP was used as i.p. injections at 10 mg/Kg daily throughout the duration of the experiment. Tumor measurements were taken daily with a caliper, and tumor volume was calculated with the formula ([length in millimeters]×[width in millimeters]²)/2. Mice in the various treatment groups were weighed at the beginning and at the end of each experiment.

In vivo subcellular fractionation was performed as follows. HL60 xenograft tumors from vehicle- or Gamitrinib-treated mice were harvested when they reached a volume of 300-400 mm³, and cytosol fractions were prepared using a Mitochondria Isolation Kit (SIGMA). Cytochrome c released in the cytosol was analyzed by Western blotting.

In situ internucleosomal DNA fragmentation (TUNEL) was performed as follows. At the end of treatment, tumors were harvested from vehicle- or Gamitrinib-treated animals, fixed in formalin, embedded in paraffin, and sectioned. TUNEL staining was performed with the ApopTag Plus Peroxidase In Situ Apoptosis Detection kit (Chemicon), according to the instruction manual, as described previously (Dohi et al., Mol Cell, 27:17-28 (2007)). Images were captured using an Olympus microscope with an on-line charge-coupled device camera at 400× magnification (necrotic regions were excluded from the analysis). For quantification, TUNEL-positive cells were counted in 10 independent areas of a 400× magnification field (10 fields/each group).

Histology was performed as follows. Animals in the vehicle or Gamitrinib group were euthanized at the end of the experiment, and organs, including brain, colon, heart, kidney, liver, lung, pancreas, small intestine, spleen, and stomach were collected, fixed in formalin and embedded in paraffin. Sections (5 μm) were put on high-adhesive slides, stained with hematoxylin eosin and analyzed by light microscopy.

Data were analyzed using the unpaired t-test on a GraphPad software program (Prism 4.0). All of the statistical tests were two sided. A p-value of 0.05 was considered to be statistically significant.

Figure 18A:
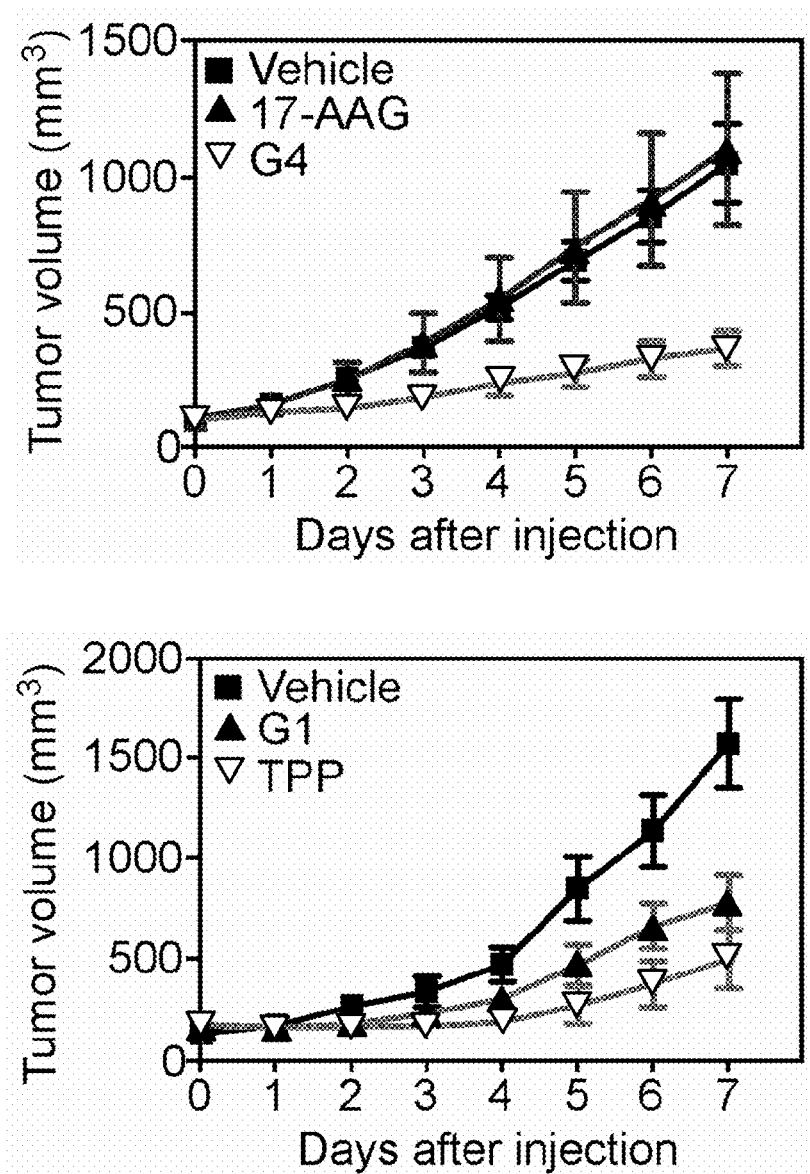
FIG. 18A consists of two line graphs at top and bottom. The line graph at top shows tumor volume as a function of time in SCID/beige mice carrying H460 lung adenocarcinoma xenograft tumors (100-150 mm$^3$) and treated with Gamitrinib-G4 ("G4") or 17-AAG. The line graph at bottom shows tumor volume as a function of time in mice treated with a dose escalation regimen as described in Example 11 with vehicle, Gamitrinib-G1 ("G1") or Gamitrinib-TPP ("TPP"). Tumor volume was measured with a caliper.
Figure 18C:
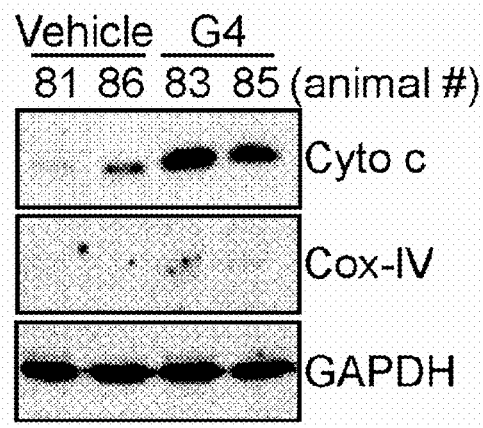
FIG. 18C shows a series of immunoblots for cytochrome c (Cyto c), Cox-IV, and GAPDH in cytosolic fractions of H460 xenograft tumors harvested from vehicle- or Gamitrinib-G4 ("G4") treated animals. Two mice/group (animal #) were analyzed.
Figure 18D:
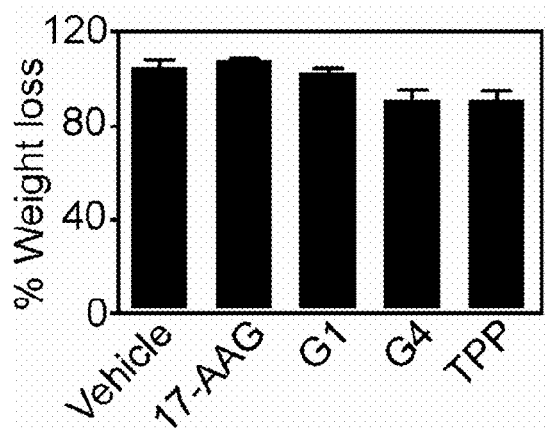
FIG. 18D is a bar graph showing percentage weight loss in mice treated with vehicle, 17-AAG, Gamatrinib-G1 ("G1"), Gamatrinib-G4 ("G4"), or Gamatrinib-TPP ("TPP") as measured at the end of the experiment. Mean±SEM.
Figure 18E:
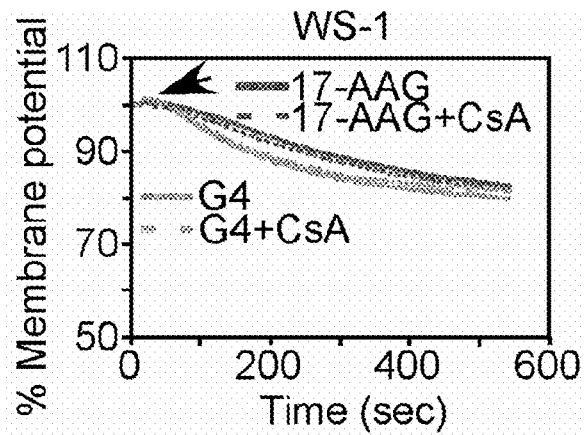
FIG. 18E is a line graph showing percentage membrane potential over time in TMRM-loaded mitochondria isolated from normal WS-1 fibroblasts and incubated with uncoupled 17-AAG/TG-OH or Gamitrinib-G4 ("G4"), with or without CsA. Arrow, point of addition.
Figure 18F:
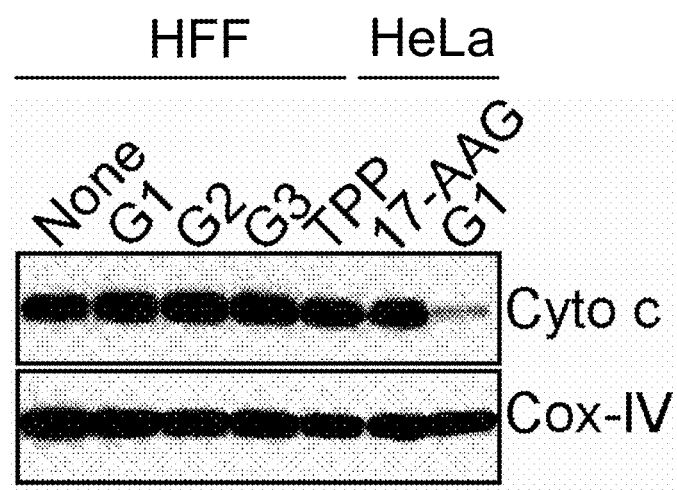
FIG. 18F shows two immunoblots for Cyto c and Cox-IV in mitochondria isolated from normal HFF fibroblasts or HeLa cells and treated with Gamitrinib-G1 ("G1"), Gamitrinib-G2 ("G2"), Gamitrinib-G3 ("G3"), Gamitrinib-G4 ("G4"), Gamitrinib-TPP ("TPP"), or 17-AAG. Cox-IV was used as a mitochondrial marker.
Figure 18G:
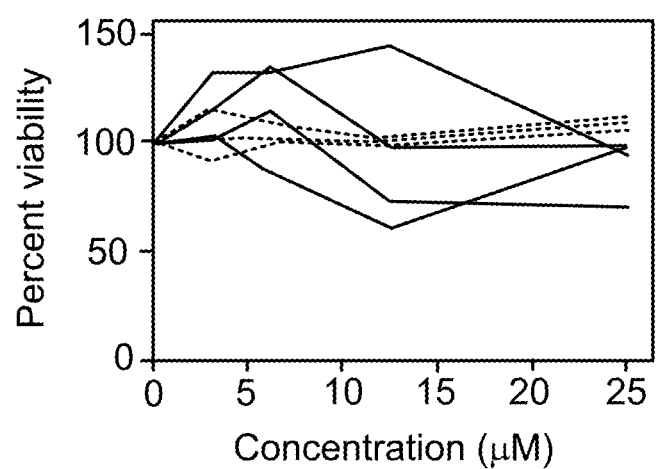
FIG. 18G is a line graph showing percent viability as a function of concentration of Gamitrinib-G4 (solid lines) or 17-AAG (dashed lines) in human fibroblasts (HFF, black line), bovine aortic endothelial cells (medium grey), intestinal epithelial cells (dark grey), or human umbilical vein endothelial cells (light grey) as analyzed by MTT after 24 hours of incubation. Data are representative of two experiments.

Systemic administration of Gamitrinib-G4 to mice inhibited the growth of established human leukemia (FIG. 20A), breast tumors (FIG. 20B), and lung tumors (FIG. 18A) in vivo. Comparable doses of 17-AAG had no effect on human lung cancer growth in mice (FIG. 18A, top). Gamitrinibs carrying different mitochondriotropic moieties (monoguanidinium (G1) or triphenylphosphonium (TPP)) also inhibited lung cancer growth in vivo (FIG. 18A, bottom). Lung tumors harvested from Gamitrinib-treated animals exhibited extensive apoptosis in situ (FIG. 18B). In addition, lung tumors harvested from Gamitrinib-treated animals exhibited cytosolic cytochrome c (FIG. 18C), suggesting Gamitrinib induced mitochondrial dysfunction in vivo. Furthermore, the results suggest that Gamitrinibs could have minimal side effects: at the concentrations used, Gamitrinibs did not cause significant weight loss in animal subjects over the course of treatment (FIG. 18D), and organs collected from Gamitrinib-treated animals were histologically normal relative to tissues from animals not treated with Gamitrinib. In order to determine if Gamitrinibs induction of mitochondrial dysfunction is selective for tumor, but not normal cells, Gamitrinib was used to treat tumor and normal cells. Effective concentrations of Gamitrinib did not affect mitochondrial membrane potential (in the presence and absence of CsA (FIG. 18E)) of normal human fibroblasts. Neither did Gamitrinib affect the cytochrome c content (FIG. 18F) of normal human fibroblasts. Concentrations of Gamitrinibs that induce complete tumor cell killing did not decrease the viability of normal human cell types (FIG. 18G).

These results indicate that Gamitrinibs are selective, effective, and safe.

Example 12: Computational Methods for Identifying Mitochondriotropic Chaperone Inhibitors The crystal structure of Hsp90 used for all docking calculations was taken from the protein data bank with coordinates corresponding to the pdb code 1YET.pdb (Stebbins et al., Cell, 89:239-250 (1997)). The original X-ray structure contained the ligand Geldanamycin (GA), which was removed from the active site to yield the apo-open form of Hsp90. Gamitrinib was docked into the active site of Hsp90 using different docking procedures, different computational approaches programs, and energy functions to define a consensus structure representative of the free energy minimum of the Gamitrinib-Hsp90 complex. First, the structure of Gamitrinib was minimized using the Macromodel program (Mohamadi et al., J. Comp. Chem., 11:440-467 (1990)), the AMBER force field (Duan et al., J. Comp. Chem., 24:1999-2012 (2003)) and the GB/SA approach (Rami Reddy et al., J. Comp. Chem., 19:769-780 (1998)) to take into account the effects of the water solvent.

In a first set of docking calculations, the energy minimized structure of Gamitrinib was subjected to blind docking experiments on the putative N-terminal Hsp90 receptor using the program AutoDock (Morris et al., J. Comp. Chem. 19:1639-1662 (1998)). Mass-centered grid maps were generated with 0.35 Å spacing by the program Autogrid around the ATPase pocket of Hsp90. Lennard-Jones parameters 12-10 and 12-6 (default parameters in the program package) were used for modeling H-bonding and Van der Waals interactions, respectively. The distance dependent dielectric permittivity of Mehler and Solmajer (Mehler and Solmajer, Protein Eng, 4:903-910 (1991)) was used for the calculation of the electrostatic grid maps. The Lamarckian genetic algorithm (LGA) and the pseudo-Solis and West methods were applied for minimization using default parameters. The number of generations was set to 25 million in all runs, and the stopping criterion was therefore defined by the total number of energy evaluations. Random starting positions on the grid, random orientations, and torsions (flexible ligand only) were used for the ligand. A total of 310 runs were performed. At the end of the docking runs, conformations of the ligand were listed in increasing energy order. Subsequently, the ligand conformation with lowest energy was used as a reference, and all conformations with a center of mass to center of mass distance of <1.5 Å from the reference were taken to belong to the first cluster. Once a conformation was assigned to a cluster, it was not used again for other (energetically less favorable) clusters. Then the process was repeated for all hitherto unclassified conformations until all conformations were put in a cluster. Most of the docked structures shared common conformational characteristics which are prototypically represented by the structure of the global minimum of the complex. The 17-AAG region of free energy minimum structure obtained from the Autodock runs is well superimposible to the benzoquinone ansamicyin backbone of GA with a root mean square deviation (rmsd) of all heavy atoms of 0.56 Å.

In a second set of docking calculations, the minimized structure of Gamitrinib was docked onto the Hsp90 receptor using the Glide software (Friesner et al., J. Med. Chem., 47:1739-1749 (2004); and Halgren et al., J. Med. Chem., 47:1750-1759 (2004)). A cubic bounding box of 14 Å length on for each side was build for the ligand around the ATPase binding pocket. Full flexibility was allowed for the ligand and the docking poses were scored using the Glide standard-precision (SP) mode. The 17-AAG region of Gamitrinib in best docking pose obtained from this procedure is once again superimposible to the benzoquinone ansamicyin backbone of GA in the X-ray structure (Stebbins et al., Cell, 89:239-250 (1997)), and in previous docking calculation (rmsd of 0.51 Å).

Finally, in order to evaluate the possibility that different conformations of the flexible ligand may determine a different complex geometry, Gamitrinib was subjected to a preliminary conformational analysis in isolation in solution, with an implicit representation of water through the GB/SA method. To explore the conformational space of Gamitrinib, a torsion-based conformational search was run using 10000 steps of Monte Carlo Multiple Minimum method (Chang et al., J. Am. Chem. Soc., 111:4379-4386 (1989)) and the AMBER force field, as implemented in Macromodel. 4223 unique conformations were identified and saved for the ligand. All the conformations obtained from this calculation were then used as ligands for docking calculations on the Hsp90 receptor using the same procedures as described in the simple Glide docking approach. Each the conformations docked into the receptor with a different score. Importantly, the top-ranked 226 poses are once more fully overlapping in their 17-AAG region with the to the benzoquinone ansamicyin backbone of GA, with an average rmsd of 0.6 Å.

Example 13: Synthesis of (4E,6Z,8S,9S,10E,12S, 13R,14S,16R)-19-(3-(4-(3-(((2R,8R)-8-((((2R,8R)-8-((((2R,8R)-8-((((2R,8R)-8-((tert-butyldiphenylsilyloxy)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, tetrakis hexafluorophosphate salt (Gamitrinib-G4, 1)

Step 1. ((2R,8R)-8-((((2R,8R)-8-((((2R,8R)-8-((((2R,8R)-8-((tert-butyldiphenylsilyloxy)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methyl methanesulfonate, tetrakis hexafluorophosphate salt 4

A solution of alcohol 3 (synthesized as described in Fernandez-Carneado et al., J. Am. Chem. Soc., 127:869-874 (2005), 445 mg, 0.276 mmol) in acetonitrile (5 mL) was treated with N-methylmorpholine (0.30 mL, 2.76 mmol) and methanesulfonic anhydride (240 mg, 1.38 mmol) at room temperature under $N_2$. After stirred for 5 hours at room

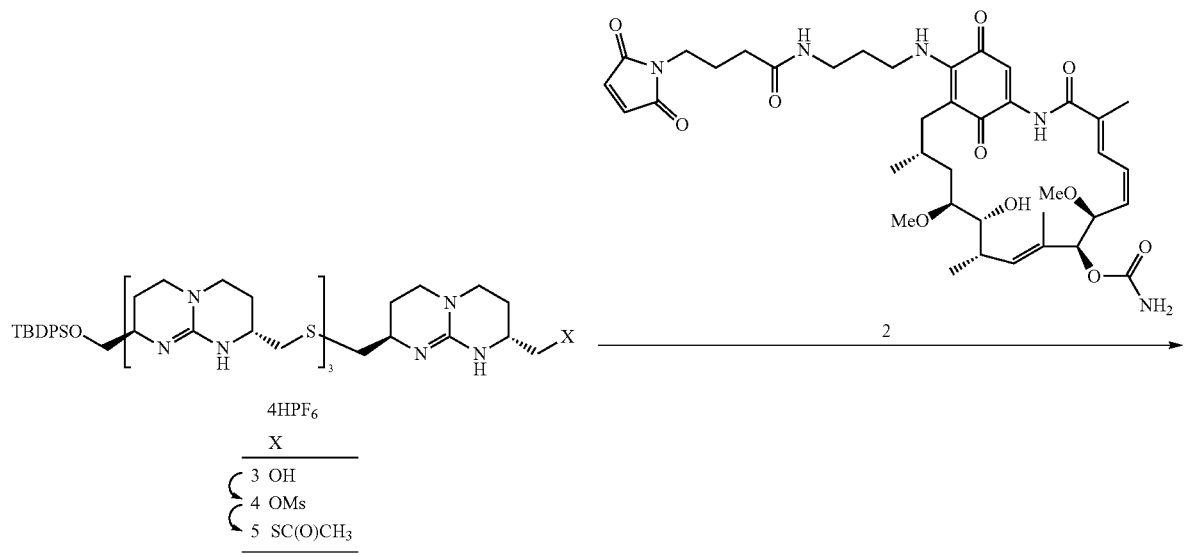

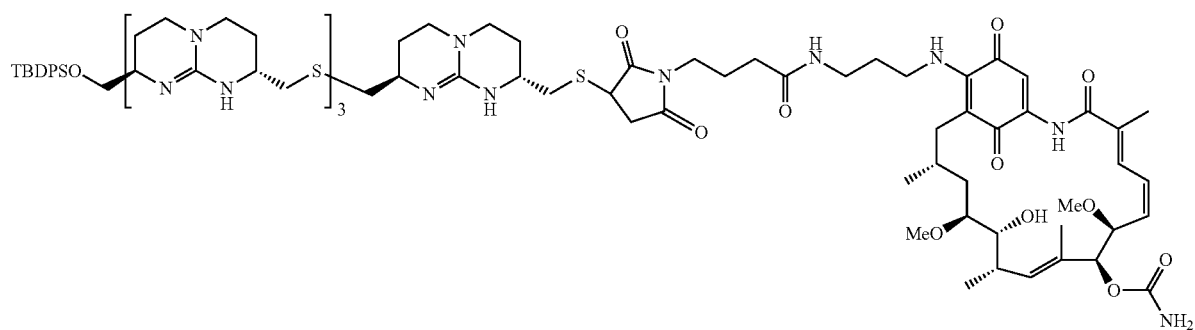

temperature, most of the volatiles were removed in vacuo. The residue was diluted with dichloromethane (30 mL) and washed with 0.1 M aq. NH$_4$PF$_6$ (20 mL). The aqueous phase was re-extracted with additional dichloromethane (30 mL). The combined organic phase was dried over Na$_2$SO$_4$, filtered and concentrated. Purification by column chromatography (2-5% MeOH in dichloromethane) afforded 4 as tetrahexafluorophosphate salt (452 mg, 97%, pale brown foam). $^1$H-NMR (600 MHz, acetone-d$_6$) δ 7.72-7.67 (m, 4H), 7.52-7.48 (m, 2H), 7.48-7.43 (m, 4H), 7.35-7.00 (br, salt protons), 4.46 (dd, 1H, J=4.2 Hz, 10.8 Hz), 4.28 (dd, 1H, J=7.2 Hz, 10.2 Hz), 4.00-3.95 (m, 1H), 3.85-3.68 (m, 9H), 3.60-3.47 (m, 16H), 3.18 (s, 3H), 3.04-2.95 (m, 6H), 2.76-2.68 (m, 6H), 2.28-2.14 (m, 8H), 2.05-1.89 (m, 8H), 1.06 (s, 9H).

Step 2. S-((2R,8R)-8-(((((2R,8R)-8-(((((2R,8R)-8-(((((2R,8R)-8-((tert-butyldiphenylsilyloxy)methyl)-2, 3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl) methyl ethanethioate, tetrakis hexafluorophosphate salt 5

A solution of the mesylate 4 (452 mg, 0.267 mmol) and potassium thioacetate (153 mg, 1.34 mmol) in tetrahydrofuran (THF, 8 mL)/H$_2$O (3 mL) was refluxed for 16 hours. After cooling to room temperature, the reaction mixture was diluted with dichloromethane (30 mL) and washed with 0.1 M aq. NH$_4$PF$_6$ (20 mL). The aqueous phase was re-extracted with additional dichloromethane (30 mL). The combined organic phase was washed with 0.1 M aq. NH$_4$PF$_6$ (20 mL), dried over Na$_2$SO$_4$, filtered and concentrated. Trituration from diethyl ether-hexanes (1:1) afforded 5 as a tetrahexafluorophosphate salt (420 mg, 94%, pale brown solid). $^1$H-NMR (400 MHz, acetone-d$_6$) δ 7.73-7.66 (m, 4H), 7.53-7.42 (m, 6H), 7.22-6.92 (br, salt protons), 3.85-3.65 (m, 10H), 3.62-3.46 (m, 16H), 3.16 (d, 2H, J=6.4 Hz), 3.04-2.86 (m, 6H), 2.77-2.67 (m, 6H), 2.37 (s, 3H), 2.29-2.14 (m, 8H), 2.04-1.88 (m, 8H), 1.06 (s, 9H); MS (EI) m/z 1087 (M+1), 1233 (M+HPF$_6$+1).

Step 3. (4E,6Z,8S,9S,10E,12S,13R,14S,16R)-19-(3-(4-(3-(((2R,8R)-8-(((((2R,8R)-8-(((((2R,8R)-8-(((((2R,8R)-8-((tert-butyldiphenylsilyloxy)methyl)-2,3,4,6, 7, 8-hexahydro-1H-pyrimido[1,2-a]pyrimidin-2-yl) methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a] pyrimidin-2-yl)methylthio)methyl)-2,3,4,6, 7, 8-hexahydro-1H-pyrimido[1,2-a]pyrimidin-2-yl) methylthio)-2,5-dioxopyrrolidin-1-yl)butanamido) propylamino)-13-hydroxy-8,14-dimethoxy-4, 10,12, 16-tetramethyl-3,20,22-trioxo-2-azabicyclo[16.3.1] docosa-1(21),4,6,10,18-pentaen-9-yl carbamate, tetrakis hexafluorophosphate salt 1

A solution of 5 (118 mg, 0.071 mmol) in degassed MeOH (4 mL) under N$_2$ at room temperature was treated with potassium tert-butoxide (0.21 mL, 0.21 mmol, 1 M in THF). After 30 minutes, the reaction mixture was neutralized with 1 N aq. HCl (ca. 0.1 mL) and treated with 0.1 N phosphate buffer (pH 6, 3 mL). To the buffered solution under N$_2$ at room temperature was added a solution of geldanamycin-maleimide 2 (synthesized as described in Mandler, et al. Bioconjug. Chem. 13:786-791 (2002), 65 mg, 0.085 mmol) in degassed MeOH (2 mL). After 2 hours, the reaction was concentrated to ca. 3 mL. The resulting reaction mixture was diluted with dichloromethane (20 mL) and washed with 0.1 M aq. NH$_4$PF$_6$ (30 mL). The aqueous phase was re-extracted with dichloromethane (20 mL). The combined organic phase was dried over Na$_2$SO$_4$, filtered and concentrated. Separation by prep-HPLC (5-50% acetonitrile in water, 0.1% TFA) followed by concentration afforded 1 as a trifluoroacetate (TFA) salt. The TFA salt was dissolved in dichloromethane (3 mL) and washed successively with 0.1 M aq. NH$_4$PF$_6$ (2 mL×5). Concentration followed by trituration from diethyl ether-hexanes (1:1) afforded 1 as tetrahexafluorophosphate salt (88 mg, 52%, purple solid). The purity of 1 was more than 99% by HPLC at 254 nm. The measured molecular mass of 1 ([M+3E1]$^{3+}$, m/z 604.9698) measured by HRMS was consistent with the theoretical mass (m/z 604.9736). $^1$H-NMR (400 MHz, CD$_3$CN) δ 9.25 (s, 1H), 7.70-7.60 (m, 4H), 7.53-7.40 (m, 6H), 7.30 (br s, 1H), 7.11 (d, 1H, J=8.4 Hz), 7.06 (s, 2H), 6.80-6.40 (br, salt protons), 6.74 (dt, 1H, J=18.8 Hz, J=6 Hz), 6.63 (t, 1H, J=11.2 Hz), 5.83 (t, 1H, J=10 Hz), 5.68 (d, 1H, J=9.6 Hz), 5.24 (br s, 2H), 5.08 (s, 1H), 4.43 (d, 1H, J=9.2 Hz), 3.98-3.86 (m, 1H), 3.86-3.78 (m, 1H), 3.75-3.68 (m, 1H), 3.67-3.60 (m, 1H), 3.60-3.42 (m, 14H), 3.42-3.23 (m, 21H), 3.22-3.10 (m, 3H), 3.20 (s, 3H), 3.03 (dd, 1H, J=14 Hz, 5 Hz), 2.92-2.52 (m, 7H), 2.52-2.40 (m, 9H), 2.40-2.30 (m, 1H), 2.25-2.00 (m, 10H), 1.97 (s, 3H), 1.86-1.70 (m, 14H), 1.71 (s, 3H), 1.05 (s, 9H), 0.95 (d, 3H, J=6.4 Hz), 0.92 (d, 3H, J=6.8 Hz); MS (EI) m/z 1812.5 (M+1).

Example 14: Synthesis of (4E,6Z,8S,9S,10E,12S, 13R,14S,16R)-19-(3-(4-(3-(((2R,8R)-8-((tert-butyl-diphenylsilyloxy)methyl)-2,3,4,6,7,8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, hexafluorophosphate salt (Gamitrinib-G1, I)

hexane/ethyl acetate to 100% ethyl acetate) and concentration afforded 1-2 as hexafluorophosphate salt (2.12 g, 95%, pale yellow solid). $^1$H-NMR (400 MHz, acetone-$d_6$) δ 7.72-7.65 (m, 4H), 7.52-7.41 (m, 6H), 6.98 (br, 2H), 3.85-3.73 (m, 3H), 3.73-3.64 (m, 1H), 3.61-3.46 (m, 4H), 3.15 (d, 2H, J=6.4 Hz), 2.36 (s, 3H), 2.23-2.10 (m, 2H), 2.08-1.91 (m, 2H) 1.06 (s, 9H).

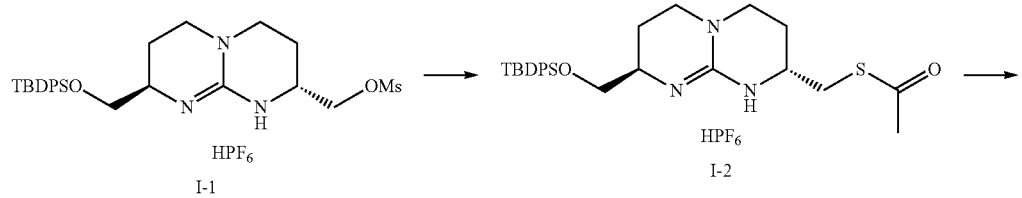

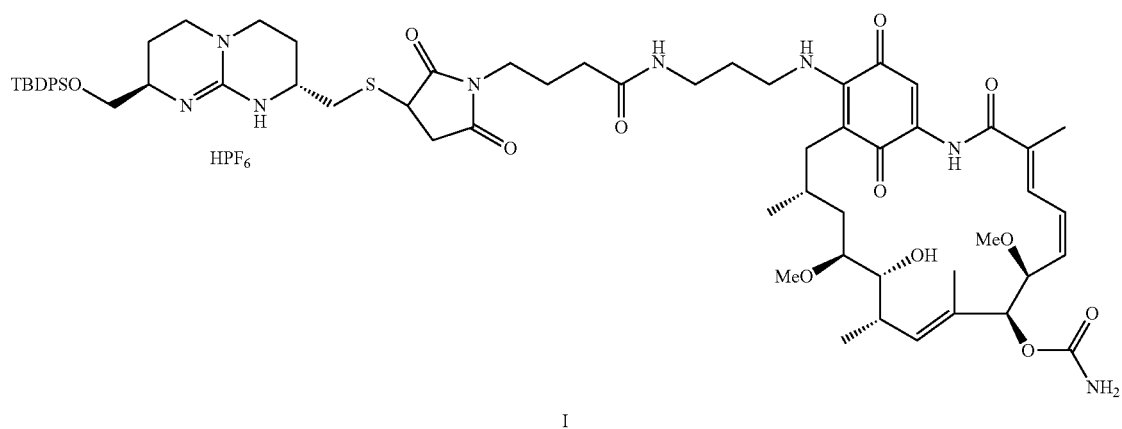

Step 1. S-((2R,8R)-8-((tert-butyldiphenylsilyloxy)methyl)-2,3,4,6, 7, 8-hexahydro-1H-pyrimido[1,2-a]pyrimidin-2-yl)methyl ethanethioate, hexafluorophosphate salt I-2

A stirred solution of I-1 (synthesized as described in Fernandez-Carneado et al., J. Am. Chem. Soc., 127:869-874 (2005), 2.30 g, 3.48 mmol) and potassium thioacetate (794 mg, 6.95 mmol) in THF (40 mL)/H$_2$O (16 mL) was refluxed for 16 hours. After cooling to room temperature, the reaction mixture was diluted with dichloromethane (100 mL) and washed with 0.1 M aq. NH$_4$PF$_6$ (50 mL). The aqueous phase was re-extracted with additional dichloromethane (50 mL). The combined organic phase was washed with 0.1 M aq. NH$_4$PF$_6$ (30 mL), dried over Na$_2$SO$_4$, filtered and concentrated. Purification by column chromatography (25%

Step 2. (4E,6Z,8S,9S,10E,12S,13R,14S,16R)-19-(3-(4-(3-(((2R,8R)-8-((tert-butyldiphenylsilyloxy)methyl)-2,3,4,6, 7, 8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, hexafluorophosphate salt I To a solution of 1-2 (100 mg, 0.156 mmol) in degassed MeOH (3 mL) under N$_2$ at room temperature was added potassium tert-butoxide (0.47 mL, 0.47 mmol, 1 M in THF). After 30 minutes, the reaction mixture was neutralized with 1 N aq. HCl (ca. 0.5 mL) and treated with 0.1 N phosphate buffer (pH=6, 2 mL). To the buffered solution under N$_2$ at room temperature was added a solution of geldanamycin-maleimide 2 (144 mg, 0.188 mmol) in degassed MeOH (1 mL). After 2 hours, the reaction was concentrated to ca. 2 mL. The resulting reaction mixture was diluted with dichloromethane (30 mL) and washed with 0.1 M aq. $NH_4PF_6$ (30 mL). The aqueous phase was re-extracted with dichloromethane (30 mL). The combined organic phase was dried over $Na_2SO_4$, filtered and concentrated. Purification by prep. HPLC (5-50% acetonitrile in water, 0.1% TFA) and concentration afforded I as TFA salt. The resulting TFA salt was dissolved in dichloromethane (3 mL) and washed with 0.1 M aq. $NH_4PF_6$ (2 mL×5). Concentration followed by trituration from diethyl ether afforded I as hexafluorophosphate salt (107 mg, 50%, purple solid). The purity of I was more than 98% by HPLC at 254 nm. The measured molecular mass of I ($[M+H]^+$, 1221.6073) measured by HRMS was consistent with the theoretical mass (m/z 1221.6090). $^1$H-NMR (600 MHz, acetone-$d_6$) δ 9.40 (d, 1H, J=5.4 Hz), 7.75-7.60 (m, 4H), 7.53-7.40 (m, 6H), 7.40-7.23 (m, 2H), 7.11 (s, 1H), 6.93-6.85 (m, 1H), 6.66 (t, 1H, J=11 Hz), 5.85 (t, 1H, J=10 Hz), 5.78 (d, 1H, J=9.6 Hz), 5.12 (s, 1H), 4.55 (d, 1H, J=9.6 Hz), 4.12-4.05 (br d, 1H), 4.06-3.98 (m, 1H), 3.98-3.93 (m, 1H), 3.85-3.45 (m, 13H), 3.39-3.15 (m, 5H), 3.32 (s, 3H), 3.20 (s, 3H), 3.05-2.95 (m, 1H), 2.87 (s, 3H), 2.77-2.68 (m, 1H), 2.64-2.58 (m, 1H), 2.53-2.39 (m, 2H), 2.30-2.13 (m, 4H), 2.05-1.91 (m, 2H), 2.01 (s, 3H), 1.88-1.76 (m, 4H), 1.75 (s, 3H), 1.75-1.67 (m, 2H), 1.06 (s, 9H), 1.00 (d, 3H), 0.91 (d, 3H) MS (EI) m/z 1221.58 (M+1).

Example 15: Synthesis of (4E,6Z,8S,9S,10E,12S,13R,14S,16R)-19-(3-(4-(3-(((2R,8R)-8-((((2R,8R)-8-((tert-butyldiphenylsilyloxy)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, bis hexafluorophosphate salt (Gamitrinib-G2, II)

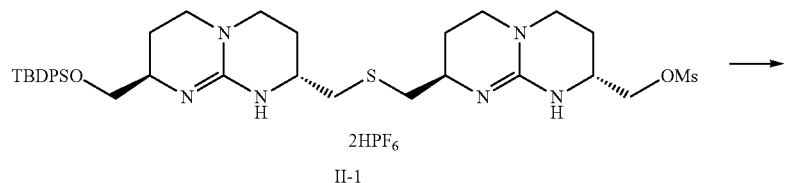

II-1

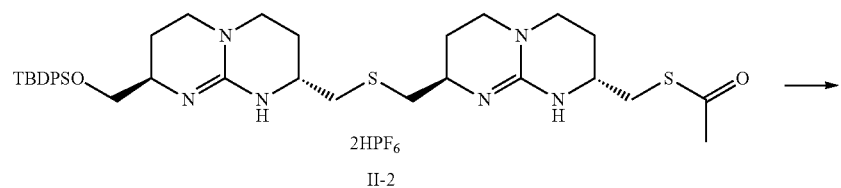

II-2

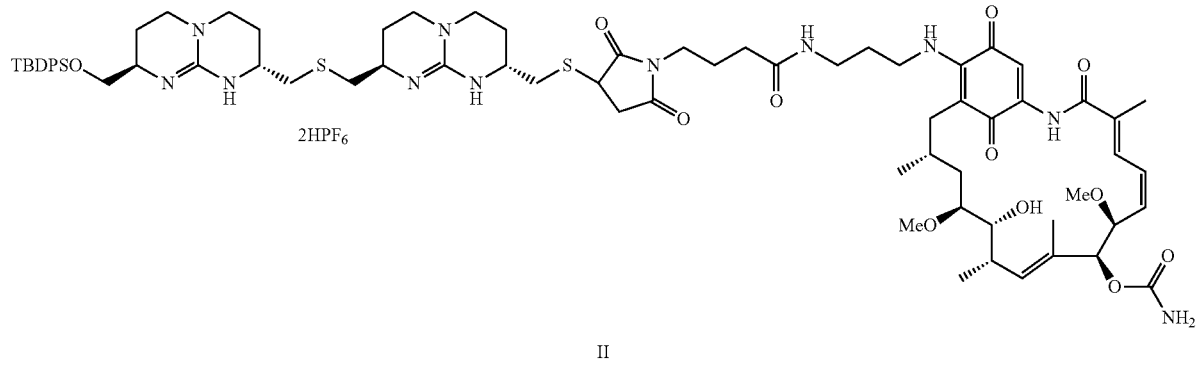

II

Step 1. S-((2R,8R)-8-((((2R,8R)-8-((tert-butyldiphe-nylsilyloxy)methyl)-2,3,4,6,7,8-hexahydro-1H-py-rimido[1,2-a]pyrimidin-2-yl)methylthio)methyl)-2,3,4,6,7,8-hexahydro-1H-pyrimido[1,2-a]pyrimidin-2-yl)methyl ethanethioate, bis hexafluorophosphate salt II-2

A stirred solution of II-1 (synthesized as described in Fernandez-Carneado et al., J. Am. Chem. Soc., 127:869-874 (2005), 1.71 g, 1.70 mmol) and potassium thioacetate (583 mg, 5.10 mmol) in THF (20 mL)/H$_2$O (8 mL) was refluxed for 16 hours. After cooling to room temperature, the reaction mixture was diluted with dichloromethane (100 mL) and washed with 0.1 M aq. NH$_4$PF$_6$ (50 mL). The aqueous phase was re-extracted with additional dichloromethane (50 mL). The combined organic phase was washed with 0.1 M aq. NH$_4$PF$_6$ (50 mL), dried over Na$_2$SO$_4$, filtered and concentrated. Purification by column chromatography (100% ethyl acetate→5% MeOH in dichloromethane) and concentration afforded 11-2 as a dihexafluorophosphate salt (1.45 g, 87%, pale brown solid). $^1$H-NMR (400 MHz, acetone-d$_6$) δ 7.73-7.67 (m, 4H), 7.53-7.42 (m, 6H), 7.27 (br d, 2H), 7.11 (br d, 2H), 3.85-3.63 (m, 6H), 3.62-3.48 (m, 8H), 3.61-3.46 (m, 4H), 3.14 (d, 2H, J=6 Hz), 2.99 (dd, 2H, J=14, 4.6 Hz), 2.73 (ddd, 2H, J=14, 9, 4.6 Hz), 2.36 (s, 3H), 2.28-2.12 (m, 4H), 2.05-1.89 (m, 4H) 1.06 (s, 9H).

Step 2. (4E,6Z,8S,9S,10E,12S,13R,14S,16R)-19-(3-(4-(3-(((2R,8R)-8-((((2R,8R)-8-((tert- butyldiphe-nylsilyloxy)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4, 10,12,16-tetramethyl-3,20, 22-trioxo-2-azabicyclo[16.3.1]docosa-1(21),4,6,10,18-pentaen-9-yl carbamate, bis hexafluorophosphate salt II To a solution of 11-2 (110 mg, 0.112 mmol) in degassed MeOH (4 mL) under N$_2$ at room temperature was added potassium tert-butoxide (0.34 mL, 0.34 mmol, 1 M in THF).

After 30 minutes, the reaction mixture was neutralized with 1 N aq. HCl (ca. 0.3 mL) and treated with 0.1 N phosphate buffer (pH 6, 0.5 mL). To the buffered solution under N$_2$ at room temperature was added a solution of geldanamycin-maleimide 2 (94 mg, 0.122 mmol) in degassed MeOH (2 mL). After 2 hours, the reaction was concentrated to ca. 2 mL. The resulting reaction mixture was diluted with dichloromethane (30 mL) and washed with 0.1 M aq. NH$_4$PF$_6$ (30 mL). The aqueous phase was re-extracted with dichloromethane (30 mL). The combined organic phase was dried over Na$_2$SO$_4$, filtered and concentrated. Purification by prep. HPLC (5-50% acetonitrile in water, 0.1% TFA) and concentration afforded II as TFA salt. The resulting TFA salt was dissolved in dichloromethane (3 mL) and washed with 0.1 M aq. NH$_4$PF$_6$ (2 mL×5). Concentration followed by trituration from diethyl ether afforded II as dihexafluorophosphate salt (55 mg, 29%, purple solid). The purity of II was more than 99% by HPLC at 254 nm. The measured molecular mass of II ([M+2H]$^{2+}$, m/z 709.8534) measured by HRMS was consistent with the theoretical mass (m/z 709.8577). $^1$H-NMR (600 MHz, CD$_3$CN) δ 9.26 (s, 1H), 7.70-7.65 (m, 4H), 7.52-7.43 (m, 6H), 7.13-7.08 (m, 1H), 7.06 (s, 1H), 6.87 (br, 1H), 6.78-6.68 (m, 1H), 6.64-6.55 (m, 2H), 6.46 (br, 1H), 5.83 (t, 1H, J=10 Hz), 5.72-5.65 (m, 1H), 5.21 (br, 2H), 5.07 (s, 1H), 4.46-4.42 (m, 1H), 3.82-3.78 (m, 1H), 3.73-3.69 (m, 1H), 3.66-3.62 (m, 1H), 3.62-3.41 (m, 9H), 3.41-3.25 (m, 11H), 3.29 (s, 3H), 3.22-3.03 (m, 3H), 3.20 (s, 3H), 2.93-2.71 (m, 3H), 2.70-2.58 (m, 2H), 2.56-2.39 (m, 3H), 2.38-2.32 (m, 1H), 2.25-2.03 (m, 5H), 1.98-1.95 (m, 6H), 1.85-1.70 (m, 8H), 1.71 (s, 3H), 1.05 (s, 9H), 0.97-0.93 (m, 3H), 0.92 (d, 3H) MS (EI) m/z 1418.51 (M+1).

Example 16: Synthesis of (4E,6Z,8S,9S,10E,12S, 13R,14S,16R)-19-(3-(4-(3-(((2R,8R)-8-((((2R,8R)-8-((((2R,8R)-8-((tert-butyldiphenylsilyloxy)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)methyl)-2,3,4,6,7,8-hexahydro-1H-pyrimido[1,2-a]pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, tris hexafluorophosphate salt (Gamitrinib-G3, III)

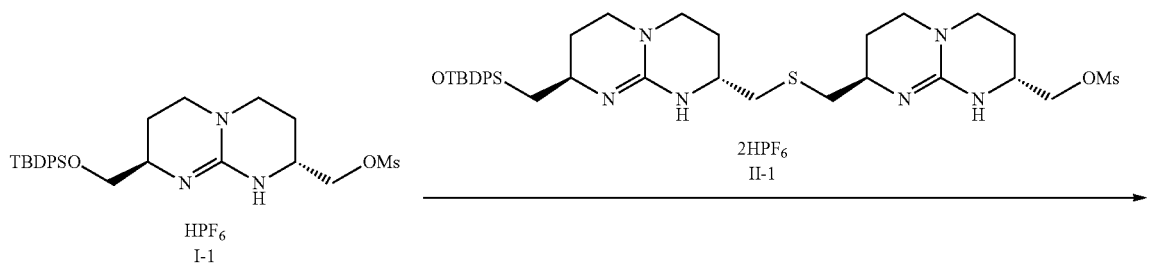

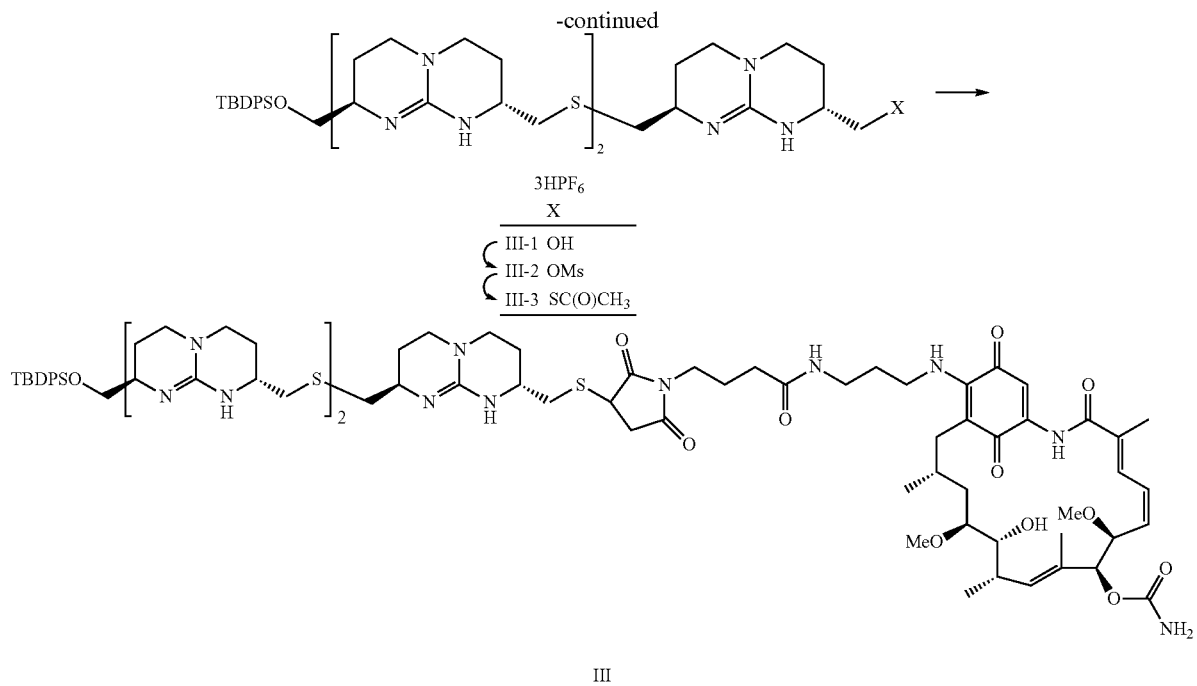

Step 1. ((2R,8R)-8-((((2R,8R)-8-((((2R,8R)-8-((tert-butyldiphenylsilyloxy)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methanol, tris hexafluorophosphate salt III-1

A stirred solution of the mesylate I-1 (545 mg, 0.82 mmol) and potassium thioacetate (188 mg, 1.65 mmol) in THF (10 mL)/$H_2O$ (4 mL) was refluxed for 16 hours. Methanesulfonic acid (0.27 mL, 4.12 mmol) was added and the reaction mixture was refluxed for 24 hours. After cooling to room temperature, organic and aqueous phases were separated in diethyl ether (50 mL) and water (50 mL). The aqueous phase was re-extracted with additional water (20 mL). The combined aqueous phases were washed with diethyl ether. Then the aqueous phases were neutralized with potassium bicarbonate (495 mg, 4.94 mmol) and the solvent was evaporated to dryness. To this resulting solid was added MeOH (100 mL), and the precipitate was removed by filtration. This procedure was repeated twice with MeOH/$CH_2Cl_2$ system (MeOH/$CH_2Cl_2$=50/50→5/95). Concentration afforded the crude yellow foam. To a solution of this product in MeOH (10 mL) were added cesium carbonate (322 mg, 0.99 mmol) and tributylphosphine (0.12 mL, 0.49 mmol) at room temperature. After being stirred for 40 minutes, a solution of the mesylate II-1 (697 mg, 0.69 mmol) in THF (10 mL) was added and the reaction mixture was stirred for 16 hours at room temperature. Then most of the volatiles were removed in vacuo. The residue was diluted with dichloromethane (50 mL) and washed with 0.1 M aq. $NH_4PF_6$ (30 mL). The aqueous phase was re-extracted with additional dichloromethane (30 mL). The combined organic phase was dried over $Na_2SO_4$, filtered and concentrated. Purification by column chromatography (MeOH/$CH_2Cl_2$: 2% to 5%) afforded III-1 (560 mg, 64%, white solid) as a trihexafluorophosphate salt. $^1$H-NMR (400 MHz, acetone-$d_6$) δ 7.74-7.70 (m, 4H), 7.54-7.44 (m, 6H), 4.28 (t, 1H, J=5.2 Hz), 3.84-3.60 (m, 8H), 3.60-3.44 (m, 14H), 3.07-2.97 (m, 4H), 2.75-2.58 (m, 4H), 2.27-2.14 (m, 5H), 2.14-1.74 (m, 7H), 1.06 (s, 9H).

Step 2. ((2R,8R)-8-((((2R,8R)-8-((((2R,8R)-8-((tert-butyldiphenylsilyloxy)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methanethiol, tris hexafluorophosphate salt III-2

A solution of alcohol III-1 (433 mg, 0.34 mmol) in THF (5 mL) was treated with N-methylmorpholine (0.19 mL, 1.70 mmol) and methanesulfonic anhydride (178 mg, 1.02 mmol) at room temperature under $N_2$. After stirred for 2 hours at room temperature, the reaction mixture was diluted with dichloromethane (30 mL) and washed with 0.1 M aq. $NH_4PF_6$ (20 mL). The aqueous phase was re-extracted with additional dichloromethane (30 mL). The combined organic phase was dried over $Na_2SO_4$, filtered and concentrated. Purification by column chromatography (MeOH/$CH_2Cl_2$: 2% to 5%) afforded III-2 as trihexafluorophosphate salt (359 mg, 78%, pale brown foam). $^1$H-NMR (400 MHz, acetone-$d_6$) δ 7.80-7.65 (m, 4H), 7.55-7.40 (m, 6H), 4.41 (dd, 1H, J=10.4 Hz, 4.4 Hz), 4.25 (dd, 1H, J=10.4 Hz, 7.6 Hz), 3.95-3.87 (m, 1H), 3.84-3.58 (m, 7H), 3.58-3.40 (m, 12H), 3.20 (s, 3H), 3.07-2.94 (m, 4H), 2.76-2.57 (m, 4H), 2.28-2.10 (m, 6H), 2.05-1.86 (m, 6H), 1.06 (s, 9H).

Step 3. S-((2R,8R)-8-((((2R,8R)-8-((tert-butyldiphenylsilyloxy)methyl)-2,3,4,6, 7, 8-hexahydro-1H-pyrimido[1,2-a]pyrimidin-2-yl) methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a]pyrimidin-2-yl)methyl ethanethioate, tris hexafluorophosphate salt III-3

A stirred solution of the mesylate III-2 (359 mg, 0.27 mmol) and potassium thioacetate (97 mg, 0.85 mmol) in THF (8 mL)/H$_2$O (3 mL) was refluxed for 16 hours. After cooling to room temperature, the reaction mixture was diluted with dichloromethane (50 mL) and washed with 0.1 M aq. NH$_4$PF$_6$ (30 mL). The aqueous phase was re-extracted with additional dichloromethane (30 mL). The combined organic phase was washed with 0.1 M aq. NH$_4$PF$_6$ (20 mL), dried over Na$_2$SO$_4$, filtered and concentrated. Trituration from diethyl ether-hexanes (1:1) afforded III-3 as trihexafluorophosphate salt (294 mg, 83%, pale yellow solid). $^1$H-NMR (600 MHz, acetone-d$_6$) δ 8.20-7.74 (br, salt protons), 7.74-7.68 (m, 4H), 7.53-7.44 (m, 6H), 3.86-3.75 (m, 3H), 3.73-3.56 (m, 5H), 3.56-3.44 (m, 12H), 3.21 (dd, 1H, J=13.8, 6 Hz), 3.08-2.95 (m, 5H), 2.80-2.61 (m, 4H), 2.37 (s, 3H), 2.24-2.10 (m, 6H), 2.00-1.82 (m, 6H) 1.06 (s, 9H).

Step 4. (4E,6Z,8S,9S,10E,12S,13R,14S,16R)-19-(3-(4-(3-(((2R,8R)-8-((((2R,8R)-8-((((2R,8R)-8-((tert-butyldiphenylsilyloxy)methyl)-2,3,4,6, 7, 8-hexahydro-1H-pyrimido[1,2-a]pyrimidin-2-yl) methylthio)methyl)-2,3,4,6, 7, 8-hexahydro-1H-pyrimido[1,2-a]pyrimidin-2-yl)methylthio)methyl)-2,3,4,6, 7, 8-hexahydro-1H-pyrimido[1,2-a] pyrimidin-2-yl)methylthio)-2,5-dioxopyrrolidin-1-yl)butanamido)propylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate, tris hexafluorophosphate salt III To a solution of III-1 (209 mg, 0.157 mmol) in degassed MeOH (4 mL) under N$_2$ at room temperature was added potassium tert-butoxide (0.47 mL, 0.47 mmol, 1 M in THF). After 30 minutes, the reaction mixture was neutralized with 1 N aq. HCl (ca. 0.1 mL) and treated with 0.1 N phosphate buffer (pH 6, 3 mL). To the buffered solution under N$_2$ at room temperature was added a solution of geldanamycin-maleimide 2 (133 mg, 0.173 mmol) in degassed MeOH (2 mL). After 2 hours, the reaction was concentrated to ca. 3 mL. The resulting reaction mixture was diluted with dichloromethane (20 mL) and washed with 0.1 M aq. NH$_4$PF$_6$ (30 mL). The aqueous phase was re-extracted with dichloromethane (20 mL). The combined organic phase was dried over Na$_2$SO$_4$, filtered and concentrated. Purification by prep. HPLC (5-50% acetonitrile in water, 0.1% TFA) and concentration afforded III as TFA salt. The resulting TFA salt was dissolved in dichloromethane (3 mL) and washed with 0.1 M aq. NH$_4$PF$_6$ (2 mL×5). Concentration followed by trituration from diethyl ether-hexanes (1:1) afforded III as trihexafluorophosphate salt (110 mg, 34%, purple solid). The purity of III was more than 96% by HPLC at 254 nm. The measured molecular mass of III ([M+3H]$^{3+}$, m/z 539.2695) measured by HRMS was consistent with the theoretical mass (m/z 539.2740). $^1$H-NMR (400 MHz, CD$_3$CN) δ 9.26 (s, 1H), 7.70-7.63 (m, 4H), 7.52-7.40 (m, 6H), 7.15-7.08 (br, 1H), 7.06 (s, 1H), 6.81-6.68 (m, 2H), 6.65-6.57 (m, 2H), 6.45-6.15 (br, 6H), 5.83 (t, 1H, J=10.2 Hz), 5.69 (d, 1H, J=7.2 Hz), 5.21 (br s, 2H), 5.08 (s, 1H), 4.44 (dd, 1H, J=9.6, 4.8 Hz), 3.83-3.78 (m, 1H), 3.73-3.70 (m, 1H), 3.66-3.61 (m, 1H), 3.61-3.42 (m, 10H), 3.42-3.25 (m, 18H), 3.22-3.14 (m, 3H), 3.20 (s, 3H), 2.85-2.71 (m, 7H), 2.71-2.41 (m, 7H), 2.38-2.32 (m, 1H), 2.25-2.18 (m, 1H), 2.18-2.04 (m, 8H), 1.97 (s, 3H), 1.85-1.70 (m, 10H), 1.72 (s, 3H), 1.06 (s, 9H), 1.01 (d, 3H), 0.95 (dd, 3H) MS (EI) m/z 1615.51 (M+1).

Example 17: Synthesis of (4E,6Z,8S,9S,10E,12S,13R,14S,16R)-19-(6-(triphenylphosphonio)hexylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate hexafluorophosphate (Gamitrinib-TPP, 9)

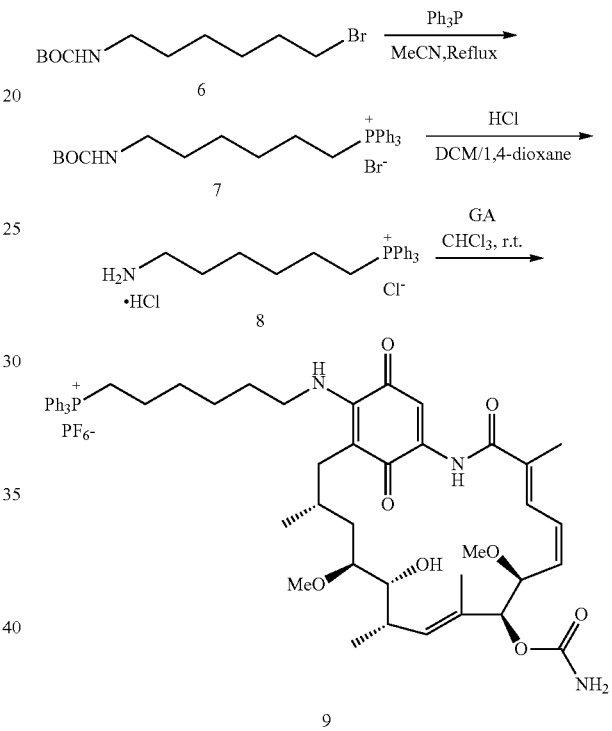

Step 1. tert-butyl 6-(triphenylphosphonium)hexylcarbamate, bromide salt 7

To a solution of 6 (synthesized as described in Egbertson, et al. J. Med. Chem., 37:2537-2551 (1994), 1.60 g, 5.71 mmol) in acetonitrile (10 mL) was added triphenylphosphine (1.57 g, 5.99 mmol) and the reaction was refluxed for 16 hours. After the reaction was cooled to room temperature, excess triphenylphosphine was removed by extraction with n-hexane (100 mL×3). Concentration and drying under vacuum gave the phosphonium salt 7 (3.09 g, 99%, white solid). $^1$H-NMR (600 MHz, DMSO-d$_6$) δ 7.89-7.84 (m, 3H), 7.80-7.71 (m, 12H), 6.72 (br t, 1H), 3.57-3.50 (m, 2H), 2.85-2.79 (m, 2H), 1.50-1.38 (m, 4H), 1.30-1.16 (m, 4H).

Step 2. 6-(triphenylphosphonium)hexan-1-amine chloride hydrochloride 8

A solution of the phosphonium salt 7 (1.5 g, 0.765 mmol) in dichloromethane (100 mL) was treated with HCl solution (4 N in 1,4-dioxane, 171 mL) at room temperature. After being stirred for 3 hours, the reaction was concentrated. Drying under vacuum afforded the amine 8 (1.31 g, 99%, white solid). The amine 8 was used without further purification. $^1$H-NMR (600 MHz, DMSO-d$_6$) δ 8.12 (br s, 3H), 7.94-7.88 (m, 3H), 7.86-7.75 (m, 12H), 3.70-3.60 (m, 2H), 2.75-2.68 (m, 2H), 1.58-1.44 (m, 6H), 1.38-1.30 (m, 2H).

Step 3. (4E,6Z,8S,9S,10E,12S,13R,14S,16R)-19-(6-(triphenylphosphonio)hexylamino)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate hexafluorophosphate 9

To a solution of geldanamycin (GA, 150 mg, 0.27 mmol) in chloroform (25 mL) under N$_2$ at room temperature was added amine 8 (390 mg, 0.81 mmol) and N,N-diisopropylethylamine (0.47 mL, 2.70 mmol). After being stirred for 3 hours, additional amine 8 (390 mg, 0.81 mmol) was added. After 10 hours, the reaction was concentrated and purified by column chromatography (2-10% methanol in dichloromethane). The resulting salt was dissolved in dichloromethane (3 mL) and washed with 0.1 M aq. NH$_4$PF$_6$ (2 mL×5). Concentration followed by trituration from diethyl ether afforded 9 as a hexafluorophosphate salt (173 mg, 62%, purple solid). The purity of 9 was more than 98% by HPLC at 254 nm. The measured molecular mass of 9 (M+, m/z 890.4559) measured by FIRMS was consistent with the theoretical mass (m/z 890.4509). $^1$H-NMR (600 MHz, acetone-d$_6$) δ 9.39 (s, 1H), 8.00-7.87 (m, 9H), 7.87-7.75 (m, 6H), 7.30 (d, 1H, J=11.4 Hz), 7.10 (s, 1H), 6.66 (t, 1H, J=11 Hz), 6.58 (br, 1H), 5.85 (t, 1H, J=10 Hz), 5.78 (d, 1H, J=9.6 Hz), 5.11 (s, 1H), 4.55 (d, 1H, J=9.6 Hz), 4.06 (d, 1H, J=6 Hz), 3.66-3.55 (m, 4H), 3.54-3.47 (m, 1H), 3.37-3.33 (m, 1H), 3.31 (s, 3H), 3.21 (s, 3H), 2.78-2.68 (m, 1H), 2.59 (dd, 1H, J=13.8, 4.2 Hz), 2.40 (dd, 1H, J=13.8, 9.6 Hz), 2.01 (s, 3H), 1.90-1.77 (m, 3H), 1.74 (s, 3H), 1.74-1.62 (m, 6H), 1.54-1.45 (m, 3H), 0.97 (d, 3H, J=7.2 Hz), 0.91 (d, 3H, J=7.2 Hz) MS (EI) m/z 890.08 (M+).

Example 18: Design and Chemical Synthesis of Mitochondria-Permeable GA

A maleimido GA derivative, 17-(3-(4-Maleimidobutyrcarboxamido) propylamino)-demethoxygeldanamycin (17-GMB-APA-GA) was purchased from Invivogen. The cell permeable helix III Antennapedia peptide (ANT) was synthesized with or without an amino-terminal FITC group, and an amide (CONH2)-capped Cys residue at the COOH-terminus with the amino acid sequence, RQIKIWFQN-RRMKWKKC (SEQ ID NO:40). The sulfhydryl group of the COOH-terminal Cys in ANT was reacted with the maleimido group of 17-GMB-APA-GA to generate thioether linkages. For the conjugation reaction, ANT and 17-GMB-APA-GA were dissolved in 50 mM Hepes, pH 7.0, and DMSO, respectively, at a final concentration of 10 mM, and mixed in a 1:1 ANT:17-GMB-APAGA ratio for 1 hours at 22° C. with gentle mixing. The resulting ANT-17-GMB-APA-GA conjugate was analyzed by mass spectrometry, and used for analysis of mitochondrial permeability transition and cell viability.

General Methods

Chemical Characterization.

$^1$H-NMR spectra were obtained on either Varian Inova 400NB (400 MHz) or Varian Inova 600 (600 MHz) spectrometers. Mass spectra were recorded on a HP1100 series LC/MS spectrometer. The progress of reaction was checked on TLC plates (Macherey-Nagel 0.25 mm silica gel 60 with fluorescent indicator UV$_{254}$), and the spots were visualized under UV light (254 nm) and/or charring after dipping the TLC plate into ninhydrin or Ce—Mo staining solution. Column chromatography was performed on silica gel (Merck 9385 silica gel 60). The final products were analyzed by HPLC (Waters alliance) equipped with YMC-Pack Pro C$_{18}$RS column (YMC) and detected at 254 nm. Chemical identity of synthesized compounds was confirmed by high resolution mass spectrometry (HRMS) using Waters Q-TOF Premier mass spectrometer with the [M+2H]$^{2+}$ ion or singly charged product ions from [Glu1]-fibrinopeptide B (CAS 103213-49-6) as the lock mass reference. Theoretical molecular masses were calculated using MassLynx™ software (Waters Corp.) and compared with the measured mass. All measured masses were within measurement error (5 amu) of the theoretical values and are consistent with the expected elemental compositions. All reagents and solvents (acetonitrile, methanol, diethyl ether and hexanes) were purchased as reagent grade, and used without further purifications. Tetrahydrofuran and dichloromethane were distilled from Na-benzophenone and CaH$_2$, respectively.

Cell Lines and Antibodies.

Cervical carcinoma HeLa, colorectal adenocarcinoma HCT116, breast adenocarcinoma MCF-7 and MDA-MB-231, lung adenocarcinoma H460 and H1975, prostate adenocarcinoma PC3 and DU145, epidermoid squamous cell carcinoma A431, and B-lymphoblastoid Raji, HL-60 and U937 cells were obtained from the American Tissue Culture Collection (ATCC, Manassas, Va.), and maintained in culture according to the supplier's specifications. Human chronic myelogeneous leukemia in blast crisis K562, monocytic leukemia THP-1, glioblastoma U87MG, cervical carcinoma HeLa, colorectal adenocarcinoma HCT116, breast adenocarcinoma MCF-7 (ER-positive) and MDA-MB-231 (Estrogen receptor-negative), lung adenocarcinoma H460 and H1975, prostate adenocarcinoma PC3 and DU145, epidermoid squamous cell carcinoma A431, and B-lymphoblastoid Raji, myeloblastic leukemia HL-60 and U937 cells were obtained from the American Tissue Culture Collection (ATCC, Manassas, Va.), and maintained in culture according to the supplier's specifications. The normal human cell types, HGF, foreskin fibroblast HFF, epithelial fibroblast WS-1, and intestinal epithelial INT were also obtained from ATCC. Bovine aortic endothelial cells and human umbilical vein endothelial cells were isolated, and maintained in culture according to published protocols 16 (Mesri et al., "Suppression of vascular endothelial growth factor-mediated endothelial cell protection by Survivin targeting," Am. J. Pathol., 158:1757-1765 (2001)). Bax$^{-/-}$ and p53$^{-/-}$ HCT116 cells were kindly provided by Dr. Bert Vogelstein (Johns Hopkins University). The following antibodies were used: cytochrome c (Clontech), Cox-IV (Clontech), Hsp90 (BD Biosciences), TRAP-1 (BD Biosciences), cyclophilin D (CypD, peptidylprolyl isomerase F, ppif, Calbiochem), Bcl-2 (BD Biosciences), Smac (ProSci), mt-Hsp70 (ABR), and β-actin (Sigma-Aldrich).

Peptides, Plasmids and Recombinant Protein Expression.

HPLC-purified cell permeable retro-inverso Shepherdin peptidomimetic (survivin sequence Lys79-Leu87) and its scrambled cell-permeable variant were synthesized as described (Plescia et al., Cancer Cell, 7:457-468, (2005)), and used in analysis of cell viability, cytochrome c release and mitochondrial membrane potential. FITC conjugated native Sheph, and cell-permeable Sheph-ANT, Scram, Scram-ANT were also synthesized as described (Plescia et al., 2005, supra). A Mammalian Gene Collection (MGC)

full-length clone of CypD (GenBank Acc. No. BC030707) was purchased from Invitrogen, and amplified by PCR using primers 5' AAAAAGAATTCCTGGCGCTGCGCTGCG-GCTC 3' (SEQ ID NO:31) and 5' AAAAACTCGAGCA-GATTAGCTCAACTGGCCACAGTC 3' (SEQ ID NO:32) or, alternatively, 5' AAAAAGAATTCGGCGGCATGT-GCAGCAAGGGCTCCGGCG 3' (SEQ ID NO:33) and 5' AAAAACTCGAGCAGATTAGCTCAACTGGCCACA-GTC 3' (SEQ ID NO:34).

An MGC full length clone of TRAP-1 (GenBank ACC. No. NM_004257 (protein is NP004248)) was purchased from Invitrogen and the full length clone used for transfection experiments and the transcript corresponding to the mature form of the protein starting at Ser60 were amplified using forward primers 5' AAAAAGGATCCGTACGA-CATGGCGCGCGA 3' (SEQ I.D NO:35) and 5'AAAAAGGATCCAGCACGCAGACCGCCGAGG 3' (SEQ ID NO:36), respectively, and a 3' reverse primer: 5' AAAAACTCGAGCTAGTGTCGCTCCAGGGCCTT 3' (SEQ ID NO:37). The PCR products were digested with EcoRI/XhoI (CypD) or BamHI/XhoI (TRAP-1), and ligated in pGEX-4T (Pharmacia) or pcDNA3.0 (Invitrogen) for prokaryotic or eukaryotic/in vitro translation expression, respectively. pGEX-CypD, pGEX-TRAP-1, or pGEX-Hsp90 cDNA was transformed into BL21-CodonPlus-RIL *E. Coli* strain (Stratagene).

A full length clone of mouse PiC (Solute carrier family 25 (mitochondrial carrier, phosphate carrier), member 3 (GenBank Acc. No. AL360268 (protein is CAI13838)) was purchased from Invitrogen. A PiC cDNA was amplified using primers 5' AAAAAGGATCCAGGAGGATGT-TCTCGTCCGTAGC 3' (SEQ ID NO:38) and 5' AAAAACTCGAGCTACTCAGTTAACCCAAGCTTCT-TCTTC 3' (SEQ ID NO:39) and PCR products were digested with BamHI/XhoI, and subcloned into pcDNA3 to generate pcDNA-PiC. Recombinant proteins were induced with 0.2 mM IPTG at 30° C. for 5 hours, and purified from bacterial extracts, as described (Fortugno et al., Proc. Natl. Acad. Sci. U.S.A. 100(24):13791-6, (2003)).

Protein concentration was determined with a Protein Assay reagent (Bio-Rad) using Bovine Serum Albumin (BSA) as standard.

Submitochondrial Fractionation.

Submitochondrial fractionation was performed by phosphate swelling-shrinking as described before with minor modifications (Bijur and Jope, J. Neurochem., 87:1427-1435, (2003); Hovius et al., Biochim. Biophys. Acta, 1021: 217-226, (1990)). Briefly, highly purified mitochondrial pellets isolated by sucrose step gradient as described above were suspended in swelling buffer (10 mM KH2PO4, pH 7.4 and protease inhibitor) and incubated for 20 minutes at 0° C. with gentle mixing. Swelled mitochondria were mixed with equal volume of shrinking buffer (10 mM KH2PO4, pH 7.4, 32% sucrose, 30% glycerol, 10 mM MgCl2 and protease inhibitor) and incubated for additional 20 minutes at 0° C. After centrifugation at 10,000×g for 10 minutes, the supernatant was collected as containing outer membrane and inner membrane mitochondrial fractions (OM & IMS). The pellets were washed with 1:1 mixture of swelling/shrinking buffer three times, suspended in swelling buffer, and sonicated to disrupt the inner membrane, which was collected as containing inner membrane and matrix mitochondrial fractions (IM & MA). OM & IMS and IM & MA were further fractionated by centrifugation at 150,000×g for 1 hour at 4° C. The pellets were collected as OM and IM fractions, respectively. Supernatants were further concentrated using Centricon 10K and Microcon 10K centrifugal filter devices (Millipore) and collected as IMS and MA fractions, respectively.

In other experiments, mitochondria isolated from HeLa cells or mouse brain (2 µg/µl, 15 µl) were suspended in SHE buffer (250 mM sucrose in HE buffer), diluted in 135 µl of SHE buffer or HE buffer (10 mM Hepes, 1 mM EDTA, pH 7.2), and incubated for 15 minutes at 0° C. with mechanical disruption of the mitochondrial outer membrane by repeated pipetting. Samples were incubated with 50 µg/ml proteinase K (Roche), for 10 minutes at 0° C., mixed with 1 mM PMSF, centrifuged at 10,000×g for 10 minutes, and analyzed by Western blotting. Alternatively, samples were treated with increasing concentrations of digitonin (0-0.4%) to permeabilize the mitochondrial membrane and repartition of mitochondrial proteins from pellets to supernatants was analyzed by Western blotting, as described (Dohi et al., J. Clin. Invest. 114(8):1117-27, (2004)).

Isolation of Mitochondria and 'Mitochondriotropic' Property of Drugs.

Mitochondria were isolated from HeLa cells, as described previously (Kang et al., Cell, 131:257-270 (2007)). Briefly, HeLa cells were harvested and washed with TD buffer (135 mM NaCl, 5 mM KCl, 25 mM Tris, pH 7.6). The cell pellet was suspended in CaRSB buffer (10 mM NaCl, 1.5 mM CaCl$_2$, 10 mM Tris, pH 7.5, protease inhibitor), and incubated for 5 minutes at 0° C. Swelled cells were homogenized in a Dounce grinder, and immediately mixed with 1.5 volume of MS buffer (210 mM mannitol, 70 mM sucrose, 5 mM Tris, pH 7.6, 5 mM EDTA). Nuclei and other cellular debris were removed by centrifugation at 600×g for 15 minutes. Samples were further incubated with 200 µM Gamitrinib or 17-AAG per 2600 µg mitochondria for 5 minutes at 0° C., and treated mitochondria were re-isolated by centrifugation at 6,000×g for 10 minutes. The mitochondrial pellet was suspended in MS buffer, and applied onto a 1 M/1.5 M sucrose step gradient in 10 mM Tris, 5 mM EDTA, pH 7.6, 2 mM DTT, plus protease inhibitors for 1.5 hours at 110,000×g. The mitochondrial bands were isolated, washed in MS buffer, and lysed in buffer containing 150 mM NaCl, 10 mM Tris, pH 7.4, 0.5% IGEPAL CA-630, 1 mM EDTA, plus protease inhibitors. Protein concentrations were determined using a Bio-Rad protein assay reagent with BSA as a standard. Absorbance on comparable protein concentrations was determined at 338 nm using a DU530 spectrophotometer (Beckman Coulter). Due to maximum absorption and comparable signals to 17AAG and Gamitrinibs, absorbance at 338 nm was used for drug detection.

Fluorescence Analysis of Isolated Mitochondria.

Individual mitochondrial subfractions (20 µg) incubated with FITC-conjugated Shepherdin were incubated in 3 ml of 20 mM Tris buffer, and fluorescence intensity (U, arbitrary units) was measured at 497 nm of excitation wavelength and 525 nm of emission wavelength using a CARY ECLIPSE Fluorescence Spectrophotometer (Varian Inc. CA, USA). In some experiments, MCF-7 cells were treated with 20 µM of FITC-Shepherdin or FITC-scrambled peptide for 30 minutes. Cells were harvested and mitochondria were fractionated using a Mitochondria Isolation kit from PIERCE. Protein concentration was determined using a Protein assay reagent (Bio-Rad), with BSA as a standard. Fifty µg of protein samples were mixed with 3 ml of 20 mM Tris buffer, pH 7.4, and fluorescence intensity was measured at 497/525 nm excitation/emission wavelength on a spectrophotometer (Varian Inc. CA, USA).

In Vitro Mitochondrial Import Assay.

Import of recombinant proteins in isolated mitochondrial fractions was carried out as described (Young et al., Cell, 112:41-50, (2003)) with minor modifications. Briefly, isolated mouse brain mitochondria were washed in MC buffer containing 250 mM sucrose, 80 mM potassium acetate, 20 mM HEPES-KOH, pH 7.5, 5 mM magnesium acetate, as described. In vitro transcribed and translated 35S-labeled proteins were diluted with one vol of MCS buffer (500 mM sucrose, 80 mM potassium acetate, 20 mM HEPES-KOH (pH 7.5), 5 mM magnesium acetate), and mixed in a total volume of 50 μl with purified mitochondria (30 μg) for 1 hour at 30° C. in the presence or absence of 1 μM valinomycin. Samples were cooled on ice and treated with 50 μg/ml proteinase K for 10 minutes at 0° C. The proteolytic digestion was stopped by addition of 1 mM PMSF, and mitochondria were re-isolated by centrifugation at 6,000×g for 10 minutes. Differential protein import into mitochondria was determined by autoradiography.

Immunoprecipitation, Pull Down Assays and Affinity Chromatography.

Isolated Raji mitochondria were lysed in buffer containing 150 mM NaCl, 10 mM Tris, pH 7.4, 1% Triton X-100, 0.5% IGEPAL CA-630 plus protease inhibitors (Roche) for 1 hour at 4° C. under constant agitation. After centrifugation at 13,000×g for 10 minutes at 4° C., the supernatant was precleared with Protein G-agarose beads (Calbiochem) for 3 hours at 4° C., and 200 μg of precleared protein extracts were incubated with an antibody to Hsp90 or TRAP-1 for 16 hours at 4° C. in the presence or absence of CsA (5 μM) or GA (10 μM). The precipitated immune complexes were washed in lysis buffer and bound proteins were separated by SDS gel electrophoresis, and analyzed by Western blotting. For pull down experiments, GSH-bead-bound GST-CypD, GST-TRAP-1, or GST-Hsp90 were blocked with H-buffer containing 20 mM Hepes, pH 7.7, 75 mM KCl, 0.1 mM EDTA, 2.5 mM MgCl2, 0.05% NP40, 1 mM DTT plus 1 mg/ml BSA. Blocked beads were incubated with purified recombinant proteins or 35S-labeled proteins in H-buffer for 16 hours at 4° C. in the presence of CsA or GA. At the end of the incubation, pelleted beads were washed in Hbuffer and bound proteins were separated by SDS gel electrophoresis, and analyzed by Western blotting or autoradiography. For in vivo capture assays, GST or GST-CypD was mixed with isolated Raji mitochondria in H-buffer for 16 hours at 4° C. in the presence of CsA (5 μM) or (10 μM) GA. Bound proteins were washed, and analyzed by Western blotting. In some experiments, Shepherdin or scrambled peptidomimetic (5 mg/ml) were coupled to Sepharose beads, and used to fractionate purified Raji mitochondria. After washes, bound material was eluted with 0.1 M glycine, pH 2.5, immediately neutralized, and analyzed by Western blotting.

Cytochrome c Release.

Tumor cell types were treated with controls or the various Hsp90 antagonists, and cytosolic extracts were harvested at increasing time intervals between 5-30 minutes and analyzed by Western blotting. For experiments in a cell-free system, purified mitochondria (20 μg) were suspended in 500 μl of SB buffer (0.2 M sucrose, 10 mM Tris-MOPS, pH 7.4, 5 mM succinate, 1 mM sodium phosphate, 10 μM EGTA-Tris, and 2 μM rotenone). Samples were treated with controls or the various Hsp90 antagonists for 20 minutes at 22° C. At the end of each incubation reaction, mitochondria and supernatants were separated by centrifugation at 6,000×g for 10 minutes, and analyzed by Western blotting.

Mitochondrial Membrane Potential.

Raji cells were treated with Shepherdin or control scrambled peptidomimetic (100 μM) or 17-AAG (5 μM), loaded with the mitochondrial membrane potential-sensitive fluorescent dye JC-1, and analyzed for changes in green/red fluorescence ratio by flow cytometry. For experiments in a cell-free system, purified mitochondria isolated from primary normal cells, various tumor cells types, or normal mouse organs were suspended in SB buffer. Samples (100 μg) were incubated with 0.1 μM tetramethylrhodamine methyl ester (TMRM) in SB buffer, treated with Shepherdin or control scrambled peptidomimetic (0.5-1.5 μM), 17-AAG (1.5 μM), or ANT-GA (1-1.5 μM) in the presence or absence of CsA (5 μM), and analyzed continuously at 549 nm excitation and 575 nm emission (Photon Technology International, Inc). For these experiments, TMRM-loaded mitochondria in SB buffer were allowed to reach stable fluorescence, which was set as fully polarized state (maximum membrane potential). The fluorescence intensity after treatment with 2 mM $CaCl_2$ was set as minimum membrane potential (fully depolarized state). Changes in fluorescence intensity after each treatment were plotted as a ratio between maximum and minimum membrane potential. In some experiments, increasing concentrations (10-100 μg) of TMRM-loaded mitochondria isolated from HeLa or MCF-7 cells were diluted in 3 ml of SB buffer, normalized to a total protein concentration of 500 μg with BSA, and analyzed for changes in membrane potential in response to control or the various Hsp90 antagonists.

Mitochondrial Function.

Normal or tumor mitochondria (100 μs) were loaded with 0.1 mM tetramethylrhodamine methyl ester (TMRM), incubated with Gamitrinibs or 17-AAG, with or without CsA, and analyzed continuously for changes in inner membrane potential at 549 nm excitation and 575 nm emission (Photon Technology International, Inc.). The fluorescence intensity after treatment with 2 mM $CaCl_2$ corresponded to a fully depolarized state. Alternatively, H460 cells were labeled with the fluorescent dye JC-1 (Molecular Probes), and analyzed for changes in red/green (F1-2/F1-1) fluorescence ratio after treatment with the various agents, by multiparametric flow cytometry. Cytochrome c content in pellets or supernatants of drug-treated isolated mitochondria was determined by Western blotting.

Analysis of Cell Death.

Modulation of cell viability was determined by MTT (Kang et al., "Regulation of tumor cell mitochondrial homeostasis by an organelle-specific Hsp90 chaperone network," Cell, 131:257-270 (2007)). For determination of apoptosis, cells were analyzed for caspase activity (DEV-Dase activity) and plasma membrane integrity (propidium iodide) using CaspaTag (Intergen, Burlington, Mass.), by multiparametric flow cytometry (Kang et al., "Regulation of tumor cell mitochondrial homeostasis by an organelle-specific Hsp90 chaperone network," Cell, 131:257-270 (2007)).

Analysis of Hsp90 Function.

For GA-bead competition experiments, SkBr3 breast cancer cells were lysed in TNESV lysis buffer (50 mM Tris-HCl, pH 7.4, 1% Nonidet P-40, 2 mM EDTA, 100 mM NaCl, 1 mM sodium orthovanadate, 1 mM phenylmethylsulfonyl fluoride, 20 μg of aprotinin and leupeptin per ml). After centrifugation to clarify the supernatant, lysates were incubated with 0, 0.5, 1, or 10 μM Gamitrinib, or 0, 0.05, 0.1, or 0.5 μM GA, on ice for 30 minutes. Lysates (equal protein) were then subjected to affinity purification of Hsp90 using GA-bead precipitation and blotted for Hsp90 as previously described (Marcu et al., "Novobiocin and related coumarins and depletion of heat shock protein 90-dependent signaling proteins," J Natl Cancer Inst, 92:242-248 (2000)). The levels of Hsp90 remaining in the lysates are determined by densitometric quantifications by scanning and image analysis of Hsp90 bands visualized by Western blotting. Data were representative of two independent experiments with identical results and indicated that Gamitrinib is as effective as GA in competing with GA-beads for Hsp90 binding.

In other experiments, chaperone-dependent GST-Chk1 reconstitution was determined as described previously (Arlander et al., "Chaperoning checkpoint kinase 1 (Chk1), an Hsp90 client, with purified chaperones," J Biol Chem, 281:2989-2998 (2006)). Briefly, each sample contained 0.7 µg of resin-bound GST-Chk1 (residues 1-265), 1 µg of purified human Hsp90α, and the following amounts of other purified chaperone proteins: 10 µg Hsp70, 2 µg Hdj1, 2 µg p50$^{cdc37}$, 0.06 units CK2, 2.5 µg p60$^{Hop}$. Optical densities due to Chk1-dependent phosphorylation of Cdc25 in the presence and absence of Gamitrinib or 17-AAG were determined and plotted as fold activation above the sample lacking added chaperone proteins. In some experiments, HeLa cells were treated with Gamitrinibs (G1-G4) or 17-AAG (5 µM) for 24 hours, and isolated extracts were analyzed for modulation of Akt or Hsp70 expression, by Western blotting Cellular Imaging.

For fluorescence labeling studies, HeLa cells were incubated with FITC-conjugated Shepherdin or cell permeable scrambled peptidomimetic in the presence of the mitochondrial marker, MitoTracker. Images were taken on an inverted microscope (Zeiss Axiovert 200) using a Perkin-Elmer CSU-10 spinning-disc confocal scanner. Z-sections were taken every 0.3 µm for the entire cell using a Hamamatsu ORCA camera, and presented as a projection using Metamorph 6.3r5 (Universal Imaging Corp.). For time lapse videomicroscopy, HeLa cells were maintained in 35 mm glass-bottom tissue-culture dishes (Mat-tek). Prior to imaging, cells were incubated with 400 nM CM-H2XRos (M7513, Molecular Probes) under growth conditions for 15 minutes. After washes, fresh culture medium was added, and cells were imaged in an environmental chamber (PDMI-2; Harvard Apparatus) in complete medium with CO2 exchange (0.5 liters/minute) at 37° C. Cells were imaged every 1 minute using a 100× phase contrast lens with a green interference filter on an inverted microscope (Olympus IX-70). Images were captured on a CoolSnap HQ CCD camera (Roper Scientific) and concatenated using Metamorph software (Universal Imaging Corp.). Cells were imaged in the absence of any reagent for the first 10 minutes of the time lapse, at which point Shepherdin or cell permeable scrambled peptidomimetic was added dropwise in between acquisitions. Phase-contrast images of mitochondria were verified by the presence of CM-H2XRos labeling. In some experiments, isolated mitochondria were equilibrated with ANT-GA, treated with 50 µg/ml proteinase K, and analyzed by fluorescence microscopy.

Electron Microscopy.

Isolated HeLa cell mitochondria were fixed in 3% formaldehyde and 0.1% glutaraldehyde (EM grade) for 10 minutes at 37° C., incubated in 50 mM NH4Cl in PBS, pH 7.4, for 60 minutes at 22° C. to aminidate free aldehydes, dehydrated through a gradual series of ethanol to 100%, and transferred into a mixture of 50:50 (v/v) resin (Lowicryl K4M):100% ethanol overnight at 22° C. Samples were transferred to aliquots of fresh resin (×3) and applied to filling embedding capsules for 24 hours at 60° C. Thin sections were cut using an ultramicrotome (Reichert-Jung Ultracut E), placed on gold support rids, blocked (Zymed) for 30 minutes at 22° C., and incubated with an antibody to the N-domain of Hsp90 or control non-binding IgG After addition of gold-conjugated secondary antibodies (1:20, Jackson ImmunoResearch Laboratories), samples were washed, exposed to OsO4 vapor for 1 hour at 22° C., post-stained with uranyl acetate and lead citrate, and analyzed on a Philips EM10 electron microscope at 80 kV, as described (Dohi et al., J. Clin. Invest. 114(8):1117-27, (2004)).

Analysis of Cell Viability and Apoptosis.

Normal or tumor cell types were treated with increasing concentrations of Hsp90 antagonists or their respective controls (Shepherdin, 0-150 µM; 17-AAG, 0-100 µM; ANT-GA, 0-100 µM) for 1-2.5 hours at 37° C., and analyzed for loss of cell viability by an MTT assay (Plescia et al., Cancer Cell, 7:457-468, (2005)). Alternatively, HeLa cells were treated with the CypD inhibitor, CsA (1 µM), or transfected with control non-targeted siRNA or SmartPool siRNA (Dharmacon) to CypD, incubated with Shepherdin or control scrambled peptidomimetic after 48 hours, and analyzed for cell viability by MTT. In other experiments, HeLa cells were transfected with control non-targeted siRNA or TRAP-1-directed siRNA (Dharmacon), incubated in the presence or absence of CsA (1 µM), and analyzed for cell viability by MTT after 48 hours. Changes in protein expression in the various experiments of siRNA targeting were assessed by Western blotting. For analysis of TRAP-1-directed cytoprotection, primary nontransformed human fibroblasts HFF and WS-1 were transfected with control pcDNA3 or TRAP-1 cDNA by lipofectamine for 24 hours, exposed to increasing concentrations (0-1 µM) of the cell death stimulus staurosporine (STS), and analyzed for cell viability after additional 24 hours incubation by MTT. For analysis of apoptosis, p53+/+ or p53−/−HCT116 cells were treated with control or ANT-GA (100 µM), and analyzed for DEVDase activity (CaspaTag) and propidium iodide staining by simultaneous multiparametric flow cytometry, as described (Dohi et al., J. Clin. Invest. 114(8):1117-27, (2004); Plescia et al., Cancer Cell, 7:457-468, (2005)).

Tissue Procurement and Immunohistochemistry.

Anonymous primary surgical specimens of human breast adenocarcinoma, pancreas adenocarcinoma, lung adenocarcinoma, colon adenocarcinoma, and their respective normal tissues were obtained without identifiers from the UMass Memorial Cancer Center Tissue Bank. Tissue specimens were fixed in buffered formalin, and embedded in paraffin. For tissue staining, sections were deparaffinized, rehydrated in water, and quenched for endogenous peroxidase. Epitope heat retrieval was carried out by steaming the slides in 10% sodium citrate for 60 minutes. Processed slides were rinsed in PBS, and stained with an antibody to TRAP-1 or control IgG using standard avidin-biotin-peroxidase technique (Histostain-w plus, Zymed Laboratories). Slides were incubated with DAB as a chromogen and counterstained with haematoxylin. Two independent cases per each histopathologic diagnosis, and respective normal tissues were analyzed with identical results.

Statistical Analysis.

Data were analyzed using the two-sided unpaired t test on a GraphPad software package for Windows (Prism 4.0). A p value of 0.05 was considered as statistically significant.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a subject having brain cancer, the method comprising administering to a subject having brain cancer a therapeutically effective amount of a composition comprising a compound consisting of a geldanamycin analogue covalently bonded to a linking moiety that is covalently bonded to (aryl)$_3$P, wherein the linking moiety consists of an alkylene with six carbon atoms and the geldanamycin analogue is selected from the group consisting of: 17-allylamino-demethoxygeldanamycin, 17-dimethylaminogeldanamycin, 17-(3-(4-Maleimidobutyrcarboxamido)propylamino)-demethoxygeldanamycin, 17-(dimethylaminoethylamino)-17-demethoxygeldanamycin, 17-[2-(Pyrrolidin-1-yl)ethyl]aminno-17-demethoxygeldanamycin, 17-(dimethylaminopropylamino)-17-demethoxygeldanamycin, and

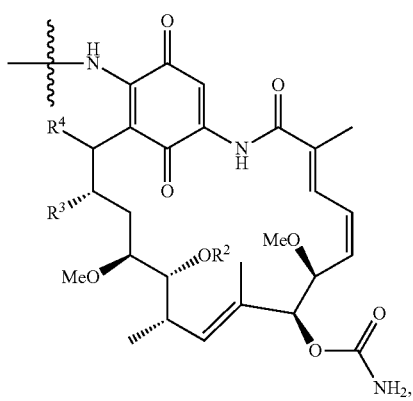

wherein: R$^2$ is H, alkyl, aryl, or arylalkyl;
R$^3$ is H, or alkyl, and R$^4$ is H, alkyl, alkenyl, aryl, arylalkyl, or OR$^d$, wherein R$^d$ is H, alkyl, or arylalkyl; or a pharmaceutically acceptable salt of the compound.

2. The method of claim 1, wherein the geldanamycin analogue is selected from the group consisting of 17-allylamino-demethoxygeldanamycin, 17-dimethylaminogeldanamycin, 17-(3-(4-Maleimidobutyrcarboxamido)propylamino)-demethoxygeldanamycin, 17-(dimethylaminoethylamino)-17-demethoxygeldanamycin, 17-[2-(Pyrrolidin-1-yl)ethyl]aminno-17-demethoxygeldanamycin, and 17-(dimethylaminopropylamino)-17-demethoxygeldanamycin.

3. The method of claim 2, wherein the geldanamycin analogue is 17-allylamino-demethoxygeldamycin (17-AAG).

4. The method of claim 2, wherein the geldanamycin analogue is 17-dimethylaminogeldanamycin.

5. The method of claim 1, wherein the geldanamycin analogue is:

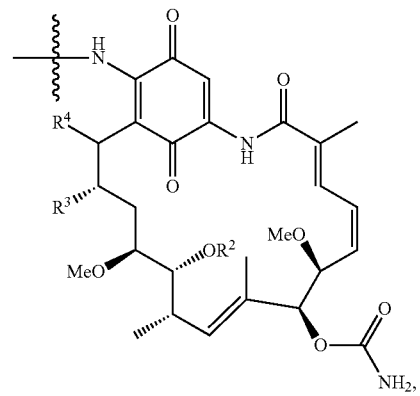

wherein:
R$^2$ is H, alkyl, aryl, or arylalkyl; R$^3$ is H, or alkyl; and R$^4$ is H, alkyl, alkenyl, aryl, arylalkyl, or OR$^d$, wherein R$^d$ is H, alkyl, or arylalkyl.

6. The method of claim 5, wherein R$^2$ is H or alkyl; R$^3$ is H or alkyl; and R$^4$ is H or OR$^d$, wherein R$^d$ is H or alkyl.

7. The method of claim 5, wherein R$^2$ is H; R$^3$ is methyl; and R$^4$ is H.

8. The method of claim 1, wherein the compound is in the form of a pharmaceutically acceptable salt.

9. The method of claim 1, wherein the (aryl)$_3$P is (phenyl)$_3$P.

10. The method of claim 1, wherein the compound consists of:

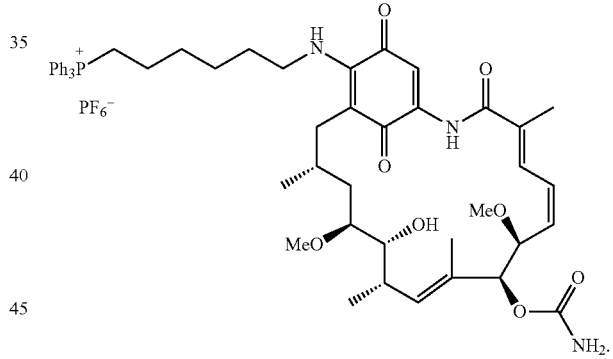

11. The method of claim 1, wherein the brain cancer is glioblastoma.

12. A method for treating a subject having brain cancer, the method comprising:
identifying a subject having brain cancer; and
administering to the subject a therapeutically effective amount of a composition comprising a compound consisting of a geldanamycin, analogue covalently bonded to a linking moiety that is covalently bonded to (aryl)$_3$P, wherein the linking moiety consists of an alkylene with six carbon atoms and the geldanamycin analogue is selected from the group consisting of: 17-allylamino-demethoxygeldanamycin, 17-dimethylaminogeldanamycin, 17-(3-(4-Maleimidobutyrcarboxamido) propylamino)-demethoxygeldanamycin, 17-(dimethylaminoethylamino)-17-demethoxygeldanamycin, 17-[2-(Pyrrolidin-1-yl)ethyl]aminno-17-demethoxygeldanamycin, 17-(dimethylaminopropylamino)-17-demethoxygeldanamycin, and

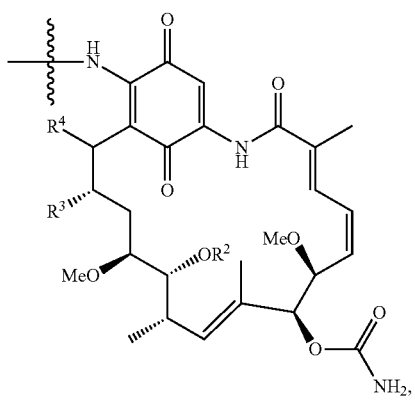

wherein: R² is H, alkyl, aryl, or arylalkyl; R³ is H, or alkyl; and R⁴ is H, alkyl, alkenyl, aryl, arylalkyl, or OR$^d$, wherein R$^d$ is H, alkyl, or arylalkyl; or a pharmaceutically acceptable salt of the compound.

13. The method of claim 12, wherein the geldanamycin analogue is selected from the group consisting of: 17-allylamino-demethoxygeldanamycin, 17-dimethylaminogeldanamycin, 17-(3-(4-Maleimidobutyrcarboxamido)propylamino)-demethoxygeldanamycin, 17-(dimethylaminoethylamino)-17-demethoxygeldanamycin, 17-[2-(Pyrrolidin-1-yl)ethyl]aminno-17-demethoxygeldanamycin, and 17-(dimethylaminopropylamino)-17-demethoxygeldanamycin.

14. The method of claim 13, wherein the geldanamycin analogue is 17-allylamino-demethoxygeldamycin (17-AAG).

15. The method of claim 13, wherein the geldanamycin analogue is 17-dimethylaminogeldanamycin.

16. The method of claim 12, wherein the geldanamycin analogue is:

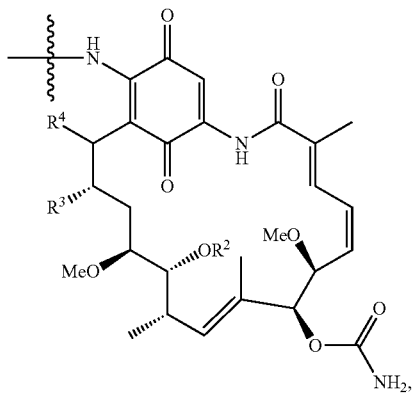

wherein;
R² is H, alkyl, aryl, or arylalkyl; R³ is H, or alkyl; and
R⁴ is H, alkyl, alkenyl, aryl, arylalkyl, or OR$^d$, wherein R$^d$ is H, alkyl, or arylalkyl.

17. The method of claim 16, wherein R² is H or alkyl; R³ is H or alkyl; and R⁴ is H or OR$^d$, wherein R$^d$ is H or alkyl.

18. The method of claim 16, wherein R² is H; R³ is methyl; and R⁴ is H.

19. The method of claim 12, wherein the compound is in the form of a pharmaceutically acceptable salt.

20. The method of claim 12, wherein the (aryl)₃P is (phenyl)₃P.

21. The method of claim 12, wherein the compound consists of:

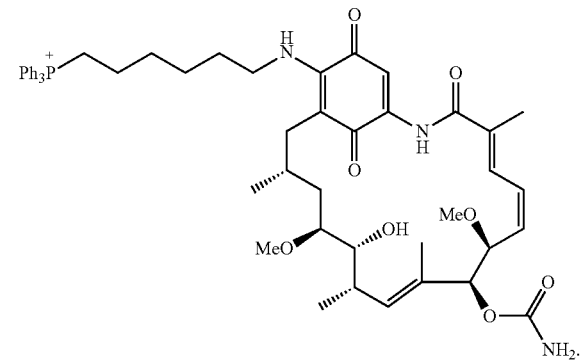

22. The method of claim 12, wherein the brain cancer is glioblastoma.

* * * * *

UNITED STATES PATENT AND TRADEMARK OFFICE
CERTIFICATE OF CORRECTION

PATENT NO. : 9,987,294 B2
APPLICATION NO. : 15/070657
DATED : June 5, 2018
INVENTOR(S) : Dario C. Altieri and Byoung Heon Kang Page 1 of 1

It is certified that error appears in the above-identified patent and that said Letters Patent is hereby corrected as shown below:

On the Title Page

Column 1 (Notice), Line 3, after "0 days." delete "days.".

In the Claims

Claim 1
Column 103, Line 15, delete "aminno-" and insert --amino--.
Column 103, Line 47, delete "alkyl," and insert --alkyl;--.

Claim 2
Column 103, Line 52, delete "of" and insert --of:--.
Column 103, Line 57, delete "aminno-" and insert --amino--.

Claim 3
Column 103, Line 61, delete "-demethoxygeldamycin" and insert --demethoxygeldanamycin--.

Claim 12
Column 104, Line 56, delete "geldanamycin," and insert --geldanamycin--.
Column 104, Line 65, delete "aminno-" and insert --amino--.

Claim 13
Column 105, Line 28, delete "aminno-" and insert --amino--.

Claim 14
Column 105, Line 31, delete "demethoxygeldamycin" and insert --demethoxygeldanamycin--.

Claim 16
Column 106, Line 1, delete "wherein;" and insert --wherein:--.

Signed and Sealed this
Seventh Day of August, 2018

Andrei Iancu
*Director of the United States Patent and Trademark Office*